US009034859B2

(12) United States Patent
Ren

(10) Patent No.: US 9,034,859 B2
(45) Date of Patent: May 19, 2015

(54) SULFATED OXYSTEROL AND OXYSTEROL SULFATION BY HYDROXYSTEROL SULFOTRANSFERASE PROMOTE LIPID HOMEOSTASIS AND LIVER PROLIFERATION

(75) Inventor: Shunlin Ren, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 13/441,241

(22) Filed: Apr. 6, 2012

(65) Prior Publication Data

US 2012/0264816 A1 Oct. 18, 2012

Related U.S. Application Data

(60) Provisional application No. 61/472,293, filed on Apr. 6, 2011, provisional application No. 61/604,711, filed on Feb. 29, 2012.

(51) Int. Cl.

| A61K 31/575 | (2006.01) |
| A61P 3/06 | (2006.01) |
| A61P 1/16 | (2006.01) |
| C07J 31/00 | (2006.01) |
| A01K 67/027 | (2006.01) |
| C12N 9/10 | (2006.01) |
| A61K 48/00 | (2006.01) |

(52) U.S. Cl.
CPC ............. *A61K 31/575* (2013.01); *A01K 67/027* (2013.01); *A61K 48/005* (2013.01); *C12N 9/13* (2013.01); *A01K 2207/25* (2013.01); *A01K 2227/105* (2013.01); *A01K 2267/0362* (2013.01); *C12N 2799/022* (2013.01); *Y10S 514/893* (2013.01)

(58) Field of Classification Search
CPC ............. C07J 9/00; A61K 31/575; C12N 9/13
See application file for complete search history.

(56) References Cited

U.S. PATENT DOCUMENTS

| 3,822,254 | A | 7/1974 | Partridge et al. |
| 3,836,527 | A | 9/1974 | Irmscher et al. |
| 3,928,397 | A | 12/1975 | Ikekawa et al. |
| 4,202,891 | A | 5/1980 | Schroepfer et al. |
| 4,225,524 | A | 9/1980 | Ochi et al. |
| 4,264,512 | A | 4/1981 | Okamura et al. |
| 4,427,668 | A | 1/1984 | Javitt |
| 6,645,953 | B2 | 11/2003 | Gronvald et al. |
| 7,524,493 | B2 * | 4/2009 | Flugelman et al. ........... 424/93.3 |
| 8,399,441 | B2 * | 3/2013 | Ren et al. ...................... 514/182 |
| 2003/0153541 | A1 | 8/2003 | Dudley et al. |
| 2004/0048838 | A1 | 3/2004 | Gronvald et al. |
| 2004/0152681 | A1 | 8/2004 | Liao et al. |
| 2005/0101573 | A1 | 5/2005 | Faarup et al. |
| 2006/0025393 | A1 | 2/2006 | Liao et al. |
| 2007/0197484 | A1 | 8/2007 | Song et al. |
| 2010/0093687 | A1 | 4/2010 | Song et al. |
| 2011/0160174 | A1 | 6/2011 | Song et al. |

FOREIGN PATENT DOCUMENTS

| EP | 0857173 B1 | 11/2003 | |
| WO | 9325568 A2 | 12/1993 | |
| WO | 9403177 A2 | 2/1994 | |
| WO | 9700884 A1 | 1/1997 | |
| WO | 9958549 A1 | 11/1999 | |
| WO | 0066611 A1 | 11/2000 | |
| WO | 0115676 A2 | 3/2001 | |
| WO | 02062302 A2 | 8/2002 | |
| WO | 02090375 A2 | 11/2002 | |
| WO | 03039480 A2 | 5/2003 | |
| WO | WO 2006/047022 * | 5/2006 | ............. A61K 31/56 |
| WO | 2008/078099 A1 | 7/2008 | |
| WO | 2011077245 A2 | 6/2011 | |

OTHER PUBLICATIONS

Yongjie Ma et al., 25-Hydroxycholesterol-3-Sulfate (25HC3S) Regulates Macrophage Lipid Metabolism via the LXR/SREBP-1 Signaling Pathway. Am J Physiol Endocrinol Metab. Dec. 2008; 295(6): E1369-E1379.*
Xu et al., Regulation of hepatocyte lipid metabolism and inflammatory response by 25-hydroxycholesterol and 25-hydroxycholesterol-3-sulfate.Lipids. Sep. 2010;45(9):821-32.*
Wenling Chen et al. Enzymatic Reduction of Oxysterols Impairs LXR Signaling in Cultured Cells and the Livers of Mice. Cell Metab. Jan. 2007 ; 5(1): 73-79.*
Giuseppe Lo Sasso et al., Down-regulation of the LXR transcriptome provides the requisite cholesterol levels to proliferating hepatocytes. Hepatology vol. 51, Issue 4, pp. 1334-1344, Apr. 2010, Article first published online: Nov. 13, 2009.*
Xin Zhang et al., Effects of 25-Hydroxycholesterol Sulfation on Liver Regeneration in Normal and Partial Hepatectomy (PHX) Mouse Models. May 2011, Gastroenterology vol. 140, Issue 5, Supplement 1, p. S-967.*
Qianming Bai et al., Sulfation of 25-hydroxycholesterol by SULT2B1b decreases cellular lipids via the LXR/SREBP-1c signaling pathway in human aortic endothelial cells. Atherosclerosis. Feb. 2011 ; 214(2): 350-356.*
Markus et al., Efficacy of Liver Transplantation in Patients with Primary Biliary Cirrhosis. N Engl J Med 1989; 320:1709-1713.*
Agarwal et al., CTLA-4 gene polymorphism confers susceptibility to primary biliary cirrhosis. Journal of Hepatology vol. 32, Issue 4, Apr. 2000, pp. 538-541.*

(Continued)

*Primary Examiner* — Scott Long
*Assistant Examiner* — Arthur S Leonard
(74) *Attorney, Agent, or Firm* — Whitham Curtis Christofferson & Cook, PC

(57) ABSTRACT

Methods and compositions for the prevention and treatment of liver damage or disease in a subject in need thereof are provided. The methods involve providing the sulfated oxysterol 25-hydroxycholesterol-3-sulfate (25HC3S) to the subject e.g. by 1) administering 25HC3S to the subject; or 2) overexpressing, in the subject, the hydroxysterol sulfotransferase enzyme SULT2B1b, which catalyzes the sulfation of 25-hydroxycholesterol (25HC) to form 25HC3S.

11 Claims, 40 Drawing Sheets

(56) References Cited

OTHER PUBLICATIONS

Duvnjak et al., Pathogenesis and management issues for non-alcoholic fatty liver disease. World journal of gastroenterology, 13 (34). pp. 4539-4550. 2007.*

Abildayeva et al., "24(S)-Hydroxycholesterol Participates in a Liver X Receptor-controlled Pathway in Astrocytes That Regulates Apolipoprotein E-Mediated Cholesterol Efflux", The Journal of Biological Chemistry, May 5, 2006, pp. 12799-12808, vol. 281, No. 18, American Society for Biochemistry and Molecular Biology, Inc.

Adams et al., "Cholesterol and 25-Hydroxycholesterol Inhibit Activation of SREPBs by Different Mechanisms, Both Involving SCAP and Insigs", The Journal of Biological Chemistry, Dec. 10, 2004, pp. 52772-52780, vol. 279, No. 50, American Society for Biochemistry and Molecular Biology, Inc.

Axelson; Larsson, "27-Hydroxylated Low Density Lipoprotein (LDL) Cholesterol Can Be Converted to 7[alpha],27-Dihydroxy-4-cholesten-3-one (Cytosterone) before Suppressing Cholesterol Production in Human Fibroblast", The Journal of Biological Chemistry, May 31, 1996, pp. 12724-12736, vol. 271, No. 22, The American Society for Biochemistry and Molecular Biology, Inc.

Bai et al., "Oxysterol sulfation by cytosolic sulfotransferase suppresses liver X receptor/sterol regulatory element binding protein-1c signaling pathway and reduces serum and hepatic lipids in mouse models of nonalcoholic fatty liver disease", Metabolism, 2012, pp. 836-845, vol. 61, Elsevier.

Bai et al., "Sulfation of 25-hydroxycholesterol by SULT2B1b decreases cellular lipids via the LXR/SREBP-1c signaling pathway in human aortic endothelial cells", Atherosclerosis, Feb. 2011, pp. 350-356, vol. 214, No. 2, Elsevier.

Bjoerkem, "Are side-chain oxidized oxysterois regulators also in vivo?", The Journal Lipid Research, Apr. 2009, pp. S213-S218, vol. 50, American Society for Biochemistry and Molecular Biology, Inc.

Cha; Kim, "Sulfated oxysterol 25HC3S as a therapeutic target of non-alcoholic fatty liver disease", Metabolism, 2012, pp. 1055-1057, vol. 61, Elsevier.

Chen et al., "Enzymatic Reduction of Oxysterols Impairs LXR Signaling in Cultered Cells and the Livers of Mice", Cell Metab., Jan. 2007, pp. 73-79, vol. 5, No. 1, Elsevier.

Cook et al., "24-Hydroxycholesterol Sulfation by Human Sytosolic Sulfotransferases: Formation of Monosulfates and Disulfates, Molecular Modeling, Sulfatase Sensitivity, and Inhibition of Liver X Receptor Activation", Drug Metabolism and Disposition, 2009, pp. 2069-2078, vol. 37, No. 10, The American Society for Pharmacology and Experimental Therapeutics.

Corsini et al., "Effects of 26-Aminocholesterol, 27-Hydroxycholesterol, and 25-Hydroxycholesterol on Proliferation and Cholesterol Homeostasis in Arterial Myocytes", Arteriosclerosis, Thrombosis, and Vascular Biology, 1995, pp. 420-428, vol. 15, American Heart Association.

Englund et al., "25-hydroxycholesterol induces lipopolysaccharide-tolerance and decreases a lipopolysaccharide-induced TNF-[gamma] secretion inmacrophages", Atherosclerosis, 2001, pp. 61-71, vol. 158, Elsevier.

Fuda et al., "Mutational Analysis of Human Hydroxysteroid Sulfotransferase SULT2B1 Isoforms Reveals That Exon 1B of the SULT2B1 Gene Produces Cholesterol Sulfotransferase, whereas Exon 1A Yields Pregnenolone Sulfotransferase", The Journal of Biological Chemistry, Sep. 27, 2002, pp. 36161-36166, vol. 277, No. 39, American Society for Biochemistry and Molecular Biology, Inc.

Fuda et al., "Oxysterols are substrates for cholesterol sulfotransferase", The Journal of Lipid Research, Mar. 2007, pp. 1343-1352, vol. 48, American Society for Biochemistry and Molecular Biology, Inc.

Geese; Raftogianis, "Biochemical Characterization and Tissue Distribution of Human SULT2B1", Biochemical and Biophysical Research Communications, 2001, pp. 280-289, vol. 288, Academic Press.

Gill et al., "Sterol regulators of cholesterol homeostasis and beyond: The oxysterol hypothesis revisited and revised", Progress in Lipid Research, 2008, pp. 391-404, vol. 47, Elsevier.

He et al., "Identification and immunohistochemical localization of Sulfotransferase 2B1b (SULT2B1b) in human lung", Biochimica et Biophysica Acta, Apr. 12, 2005, pp. 119-126, vol. 1724, Elsevier.

Higashi et al., "Expression of Cholesterol Sulfotransferase (SULT2B1b) in Human Skin and Primary Cultures of Human Epidermal Keratinocytes", The Journal of Investigative Dermatology, 2004, pp. 1207-1212, vol. 122, The Society for Investigative Dermatology.

Hylemon et al., "Identification of a Novel Regulatory Nuclear Oxysterol", Abstract, 56rd Annual Meeting of the American Association for the Study of Liver Diseased, Nov. 11-15, 2005.

Janout et al., "An Upside Down View of Cholesterol's Condensing Effect: Does Surface Occupancy Play a Role?", Langmuir, Apr. 20, 2010, pp. 5316-5318, vol. 26, No. 8.

Janowksi et al., "Structural requirements of ligands for the oxysterol liver X receptors LXR[alpha] and LXR[beta]", Proc. Natl. Acad. Sci. USA, Jan. 1999, pp. 266-271, vol. 96.

Javitt et al., "Cholesterol and Hydroxycholesterol Sulfotransferases: Identification, Distinction from Dehydroepiandrosterone Sulfotransferase, and Differential Tissue Expression", Endocrinology, 2001, pp. 2978-2984, vol. 142, No. 7, The Endocrine Society.

Ji et al., "Human Hydroxysteroid Sulfotransferase SULT2B1 Pharmacogenomics: Gene Sequence Variation and Functional Genomics", The Journal of Pharmacology and Experimental Therapeutics, 2007, pp. 529-540, vol. 322, No. 2, The American Society for Pharmacology and Experimental Therapeutics.

Kase et al., "Liver X receptor antagonist reduces lipid formation and increases glucose metabolism in myotubes from lean, obese and type 2 diabetic individuals", Diabetologia, 2007, pp. 2171-2180, vol. 50, Springer-Verlag.

Lappano et al., "The Cholesterol Metabolite 25-Hydroxycholesterol Activates Estrogen Receptor a-Mediated Si in Cancer Cells and in Cardiomyocytes", PLoS One, Jan. 31, 2011, pp. e16631-e16631, vol. 6, No. 1.

Lehmann et al., "Activation of the Nuclear Receptor LXR by Oxysterols Defines a New Hormone Response Pathway", The Journal of Biological Chemistry, Feb. 7, 1997, pp. 3137-3140, vol. 272, No. 6.

Li et al., "Biosynthesis of the regulatory oxysterol, 5-cholesten-3[beta],25-diol 3-sulfate, in hepatocytes", Journal of Lipid Research, Sep. 21, 2007, pp. 2587-2596, vol. 48.

Li et al., "Enzyme activity assay for cholesterol 27-hydroxylase in mitochondria", Journal of Lipid Research, Apr. 12, 2006, pp. 1507-1412, vol. 47.

Lo Sasso et al., "Down-Regulation of the LXR Transcriptome Provides the Requisite Cholesterol Levels to Proliferating Hepatocytes", Hepatology, 2010, pp. 1334-1344, vol. 51.

Ma et al., "25-Hydroxycholesterol-3-sulfate regulates macrophage lipid metabolism via the LXR/SREBP-1 signaling pathway", Am J Physiol Endocrinol Metab, Oct. 14, 2008, pp. E1369-E1379, vol. 295.

McDonald; Russel, "25-Hydroxycholesterol: a new life in immunology", Journal of Leukocyte Biology, Dec. 2010, pp. 1071-1072, vol. 88, Society for Leukocyte Biology.

Meloche; Falany, "Expression and characterization of the human 3[beta]-hydroxysteroid sulfotransferases (SULT2B1a and SULT2B1b)", Journal of Steroid Biochemistry & Molecular Biology, 2001, pp. 261-269, vol. 77, Elsevier.

Nelson et al., "The Oxysterol, 27-Hydroxycholesterol, Links Cholesterol Metabolism to Bone Homeostasis Through Its Actions on the Estrogen and Liver X Receptors", Endocrinology, Sep. 20, 2011, pp. 1-15, vol. 152, No. 12, The Endocrine Society.

Ogawa et al., "A facile synthesis of C-24 and C-25 oxysterols by in situ generated ethyl(trifluoromethyl)dioxirane", Steroids, 2009, pp. 81-87, vol. 74, Elsevier.

Okamura et al., "Studies on Vitamin D and Its Analogs. VIII. 3-Deoxy-1[alpha],25-Dihydroxyvitamin D3, A Potent New Analog of 1[alpha],25-(OH)2-D3.", Biochemical and Biophysical Research Communications, 1975, pp. 24-30, vol. 65, No. 1, Academic Press, Inc.

Okamura et al., "Studies on Vitamin D (Calciferol) and Its Analogues. 13. 3-Deoxy-3[alpha]-methyl-1[alpha]-hydroxyvitamin D3, 3-Deoxy-3[alpha]-methyl-1[alpha],25-dihydroxyvitamin D3, and

(56) References Cited

OTHER PUBLICATIONS

1[alpha]-Hydroxy-3-epivitamin Dr. Analogues with Conformationally Biased A Rings", Journal of Organic Chemistry, 1978, pp. 574-580, vol. 43, No. 4, American Chemical Society.

Pandak et al., "Regulation of Oxysterol 7[alpha]-Hydroxylase (CYP7B1) in Primary Cultures of Rat Hepatocytes", Hepatology, 2002, pp. 1400-1408, vol. 35, No. 6, American Association for the Study of Liver Diseases.

Pandak et al., "Transport of Cholesterol into Mitochondria is Rate-limiting for Bile Acid Synthesis via the Alternative Pathway in Primary Rat Hepatocytes", The Journal of Biological Chemistry, Oct. 3, 2002, pp. 48158-48164, vol. 277, No. 50.

Peet et al., "Cholesterol and Bile Acid Metabolism Are Impaired in Mice Lacking the Nuclear Oxysterol Receptor LXR[alpha]", Cell, May 29, 1998, pp. 693-704, vol. 93, Cell Press.

Polyzos, et al. "Sulfated oxysterols as candidates for the treatment of nonalcoholic fatty liver disease", Metabolism, 2012, pp. 755-758, vol. 61, Elsevier.

Ren et al., "25-hydroxycholesterol and 25-hydroxycholesterol 3-sulfate reciprocally regulate lipid metabolism and inflammation in hepatocytes and macrophages", Abstract, The Liver Meeting, the 60th Annual Meeting of the American Association for the Study of Liver Diseases, Oct. 30-Nov. 3, 2009.

Ren et al., "Discovery of a Novel Oxysterol, 5-Cholesten-3beta, 25-Diol 3-Sulfonate, in Nuclei and Mitochondria Following Overexpression of the Gene Encoding StarD1", Bile Acids: Biological Actions and Clinical Relevance, 2007, pp. 20-35, Kluwer Academic Publishers.

Ren et al., "Discovery of a Novel Oxysterol, 5-Cholesten-3beta, 25-Diol 3-Sulfonate, in Nuclei and Mitochondria Following Overexpression of the Gene Encoding StarD1", Abstract, International Bile Acid Meeting, XIII Falk Liver Week, Falk Symposia 155, Oct. 6-11, 2006.

Ren et al., "Discovery of a Novel Regulatory Pathway for Maintenance of Intracellular Cholesterol Homeostasis", Abstract, DDW Annual Meeting 2007, May 19-25, 2007.

Ren et al. "Identification of a novel sulfonated oxysterol, 5-cholesten-3[beta],25-diol 3-sulfonate, in hepatocyte nuclei and mitochondria", Journal of Lipid Research, Feb. 27, 2006, pp. 1081-1090, vol. 47, American Society for Biochemistry and Molecular Biology, Inc.

Ren et al., "Overexpression of Cholesterol Transporter StAR Increases in Vivo Rates of Bile Acid Synthesis in the Rat and Mouse", Liver Biology and Pathobiology, Aug. 20, 2004, pp. 910-917, vol. 40, No. 4.

Ren et al., "Regulation of Hepatocyte Lipid Metabolism by 25-Hydroxycholesterol-3-Sulfate (25HC3S) is Mediated Via the LXR/SREBP-1 Signaling Pathway", Abstract, DDW Annual Meeting 2008, May 17-23, 2008.

Ren et al., "Sulfated oxysterol, 25HC3S, is a potent regulator of lipid metabolism in human hepatocytes", Biochemical and Biophysical Research Communications, Jul. 6, 2007, pp. 802-808, vol. 360, Elsevier.

Shimizu et al., "Conservation of the Hydroxysteroid Sulfotransferase SULT2B1 Gene Structure in the Mouse: Pre-and Postnatal Expression, Kinetic Analysis of Isoforms, and Comparison with Prototypical SULT2A1", Endocrinology, Apr. 2003, pp. 1186-1193, vol. 144, No. 4, The Endocrine Society.

Ikegami et al, "Increased serum liver X receptor ligand oxysterols in patients with non-alcoholic fatty liver disease", J Gastroenterol, May 9, 2010, pp. 1257-1266, vol. 47, Springer.

Liu et al., "Nuclear Transport Modulation Reduces Hypercholesterolemia, Atherosclerosis, and Fatty Liver", Journal of the American Heart Association, Apr. 5, 2013, American Heart Association, Dallas, TX, pp. 1-17.

Song et al., "Auto-oxidized cholesterol sulfates are antagonistic ligands of liver X receptors: implications for the development and treatment of atherosclerosis", Steroids, 2001, pp. 473-479, vol. 66, Elsevier.

Strott; Higashi, "Cholesterol sulfate in human physiology: what's it all about?", Journal of Lipid Research, 2003, pp. 1268-1278, vol. 44.

Treuter, "New wrestling rules of anti-inflammatory transrepression by oxysterol receptor LXR revealed", Cell Research, 2011, pp. 711-714, vol. 21.

Williams et al., "Effects of cholesterol sulfate on lipid metabolism in cultured human keratinocytes and fibroblasts", Journal of Lipid Research, 1987, pp. 955-967, vol. 28.

Wojcicka et al., "Liver X receptors (LXRs). Part I: Structure, function, regulation of activity, and role in lipid metabolism", Postepy Hig Med Dosw., Dec. 3, 2007, pp. 736-759, vol. 61.

Xu et al., "25-Hydroxycholesterol (25HC) and 25HC-3-Sulfate (25HC3S) Mediate Nuclear Orphan Receptors in Opposite Direction in Hepatocytes", Abstract, XX International Bile Acid Meeting, Falk Symposia 165, Jun. 13-14, 2008.

Xu et al., "25-Hydroxycholesterol-3-sulfate (25HC3S) Attenuates Hepatocyte Intracellular Lipid Levels and Inflammatory Response via LXR/SREBPs and I[kappa]B[alpha]/NF-[kappa]B Pathways", Abstract, DDW Annual Meeting 2008, May 3, 2010.

Xu et al., "25-Hydroxycholesterol-3-sulfate attenuates inflammatory response via PPAR [gamma] signaling in human THP-1 macrophages", Am J Physiol Endocrinol Metab, Jan. 24, 2012, pp. E788-E799, vol. 302.

Xu et al., "25-Hydroxycholesterol-3-Sulfate Decreases Hepatic Steatosis and Inflammation in Mouse Models of Nonalcoholic Fatty Liver Disease by Down-Regulating Sterol Regulatory Element Binding Protein-1c", Abstract, DDW Annual Meeting 2011, May 7-10, 2011.

Xu et al., "Induction of I[kappa]B[alpha] Expression as a Mechanism Contributing to the Anti-inflammatory Response by 25-Hydroxycholesterol-3-Sulfate (25HC3S) in Primary Rat Hepatocytes and THP-1 Macrophages", Abstract, DDW Annual Meeting 2011, May 7-10, 2011.

Xu et al., "Regulation of Hepatocyte Lipid Metabolism and Inflammatory Response by 25-Hydroxycholesterol and 25-Hydroxycholesterol-3-sulfate", Lipids, 2010, pp. 821-832, vol. 45, AOCS. Including Online Supplemental Materials.

Zhang et al., "Cholesterol metabolite, 5-cholesten-3[beta]-25-diol-3-sulfate, promotes hepatic proliferation in mice", Journal of Steroid Biochemistry and Molecular Biology, 2012, pp. 262-270, vol. 132, Elsevier.

Zhang et al., "Cytosolic sulfotransferase 2B1b promotes hepatocyte proliferation gene expression in vivo and in vitro", Am J Physiol Gastrointest Liver Physiol, Jun. 7, 2012, pp. G344-G355, vol. 303.

Zhang et al., "Effects of 25-hydroxycholesterol sulfation on liver regeneration in normal and partial hepatectomy (PHX) mouse models.", Abstract, DDW Annual Meeting 2011, May 7-10, 2011.

Zuercher et al., "Discovery of Tertiary Sulfonamides as Potent Liver X Receptor Antagonists", J. Med. Chem., 2010, pp. 3412-3416, vol. 53, No. 8, American Chemical Society.

Pezacki et al. "Transcriptional profiling of the effects of 25-hydroxycholesterol on human hepatocyte metabolism and the antiviral state it conveys against the hepatitis C virus", BMC Chemical Biology, Jan. 16, 2009, vol. 9, No. 2, BioMed Central Ltd.

Accad et al., "Cholesterol homeostasis: A role for oxysterols", Current Biology, 1998, p. R601-R604, vol. 8.

Beltowski, "Liver X Receptors (LXR) as Therapeutic Targets in Dyslipidemia", Cardiovascular Therapy, 2008, pp. 279-316, vol. 26.

Cha et al., "The Carbohydrate-Response Element-Binding Protein is a Target Gen of LXR", Journal of Biological Chemistry, Jan. 5, 2007, pp. 743-751, vol. 282, No. 1.

Janowski et al., "An oxysterol signalling pathway mediated by the nuclear receptor LXR", Letters to Nature, Oct. 24, 1996, pp. 728-731, vol. 383.

Landis et al., "Oxysterol Activators of Liver X Receptor and 9-cis-Retinoic Acid Promote Sequential Steps in the Synthesis and Secretion of Tumor Necrosis Factor-alpha from Human Monocytes", Journal of Biological Chemistry, Feb. 15, 2002, pp. 4713-4721, vol. 277, No. 7.

Millatt et al., "Liver X receptors and the control of cholesterol homeostasis: potential therapeutic targets for the treatment of atherosclerosis", Biochimica Et Biophysica Actia, 2003, pp. 107-118, No. 1631.

(56) References Cited

OTHER PUBLICATIONS

Peet et al., "The LXRs: a new class of oxysterol receptors", Current Opinions in Genetics and Development, 1998, pp. 571-575, vol. 8.

Grefhorst et al., "Stimulation of Lipogenesis by Pharmacological Activation of the Liver X Receptor Leads to Production of Large, Triglyceride-rich Very Low Density Lipoprotein Particles", Lipids and Lipoproteins, Sep. 13, 2002, pp. 34182-34190, vol. 277, No. 37.

Kay; Fausto, "Liver regeneration: prospects for therapy based on new technologies", Molecular Medicine Today, Mar. 1997, pp. 108-115.

Trousson et al., "25-hydroxycholesterol provokes oligodendrocyte cell line apoptosis and stimulates the secreted phospholipase A2 type IIA via LXR beta and PXR", Journal of Neurochemistry, 2009, pp. 945-958, vol. 109.

Chen et al., "Influenza A virus infection activities cholesterol sulfotransferase (SULT2B1b) in the lung of female C57BL16 mice", Biol. Chem., Oct. 2011, pp. 869-876, vol. 392.

Babaev et al., "Macrophage Expression of Peroxisome Proliferator-Activated Receptor-[alpha] Reduces Atherosclerosis in Low-Density Lipoprotein Receptor-Deficient Mice", Circulation, 2007, pp. 1404-1412, vol. 116.

Xu et el., "5-Cholesten3[beta],25-Diol 3-Sulfate Decreases Lipid Accumulation in Diet-Induced Nonalcoholic Fatty Liver Disease Mouse Model", Molecular Pharmacology, Mar. 2013, 648-658, vol. 83.

Ren et al., "Sulfation of 25-hydroxycholesterol regulates lipid metabolism, inflammatory responses, and cell proliferation", Am J Physiol Endocrinol Metab, Dec. 3, 2013, pp. E123-E130, vol. 306.

\* cited by examiner

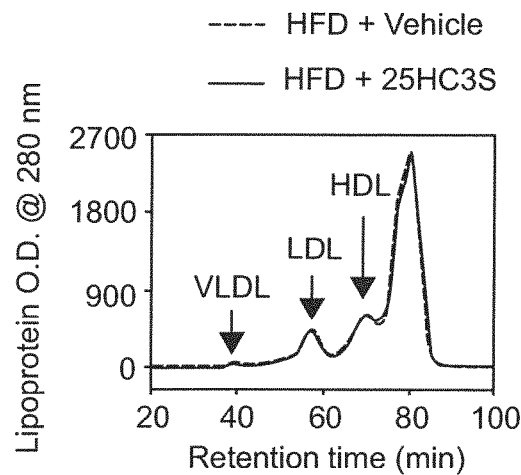
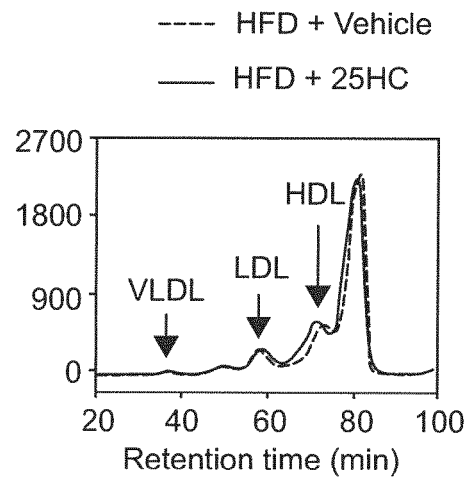
Figure 1A
Figure 1B
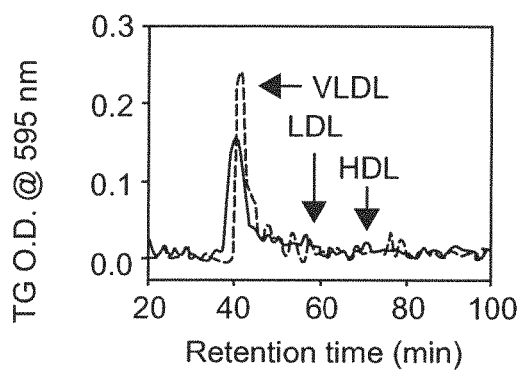
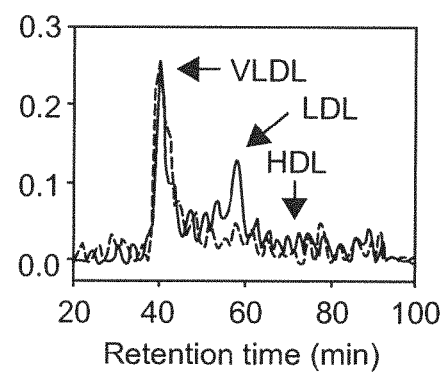
Figure 1C
Figure 1D
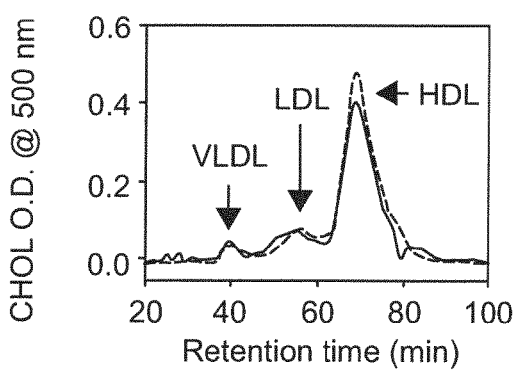
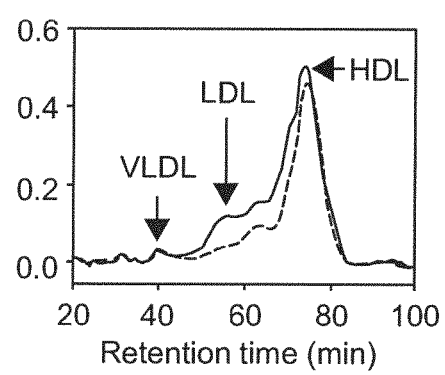
Figure 1E
Figure 1F

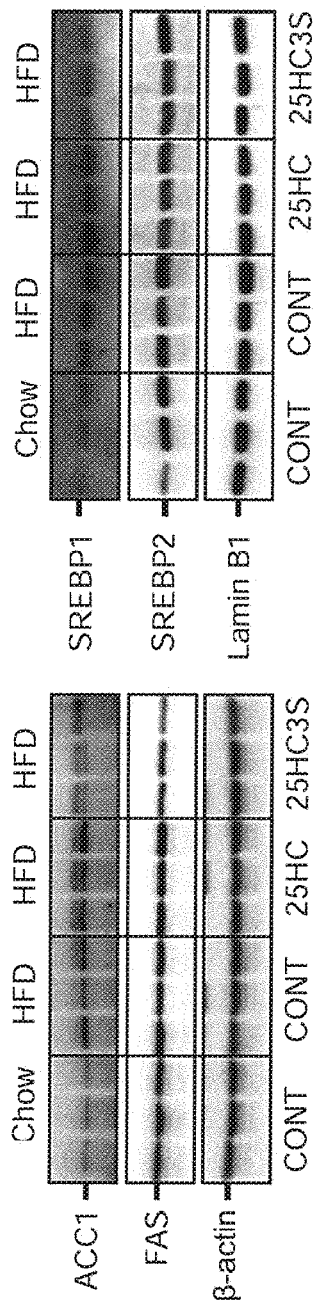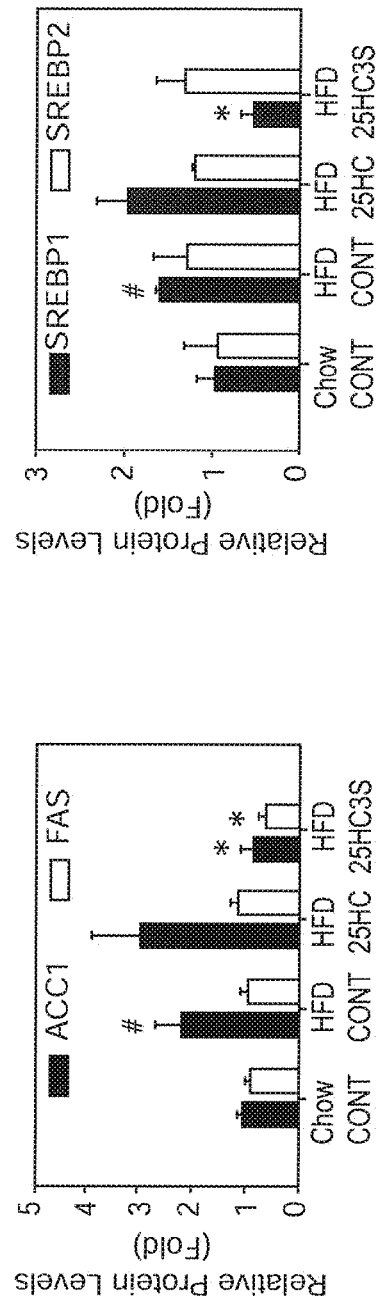
Figure 3A
Figure 3B
Figure 3C
Figure 3D

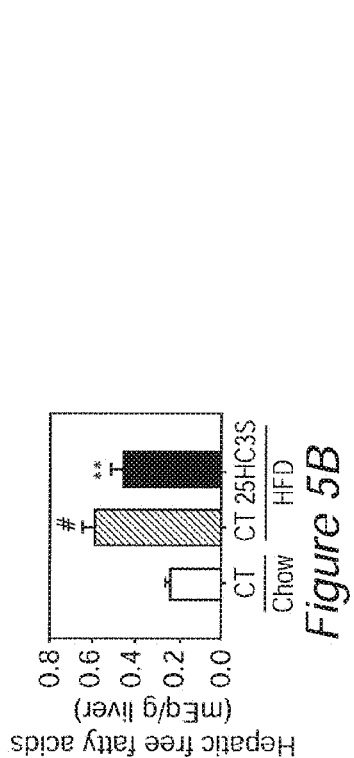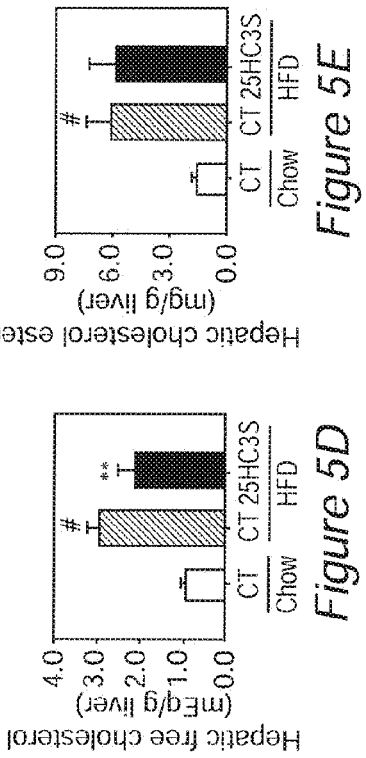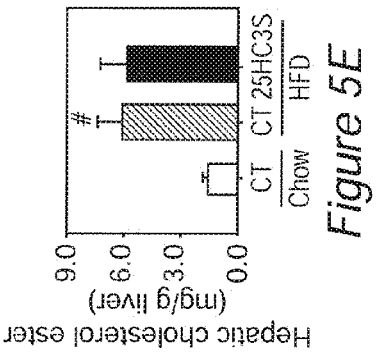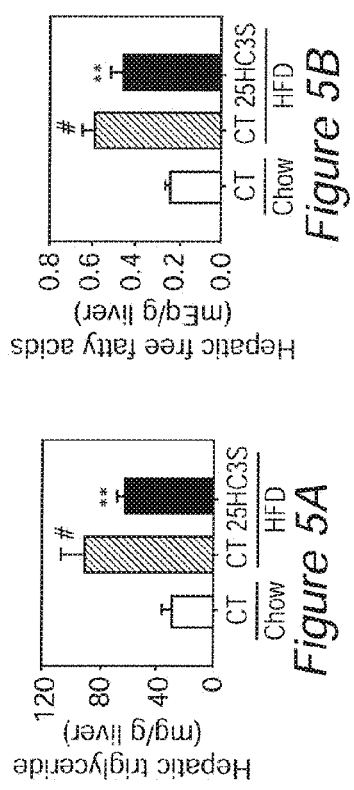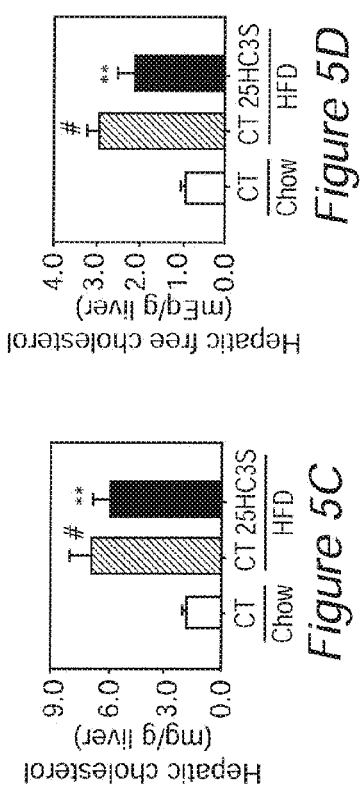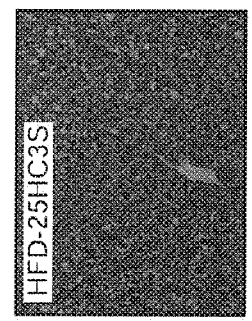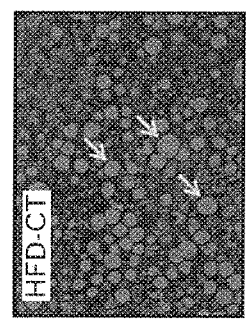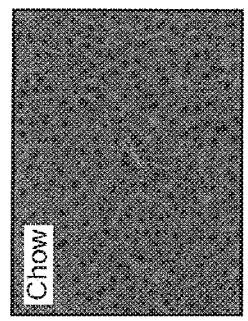

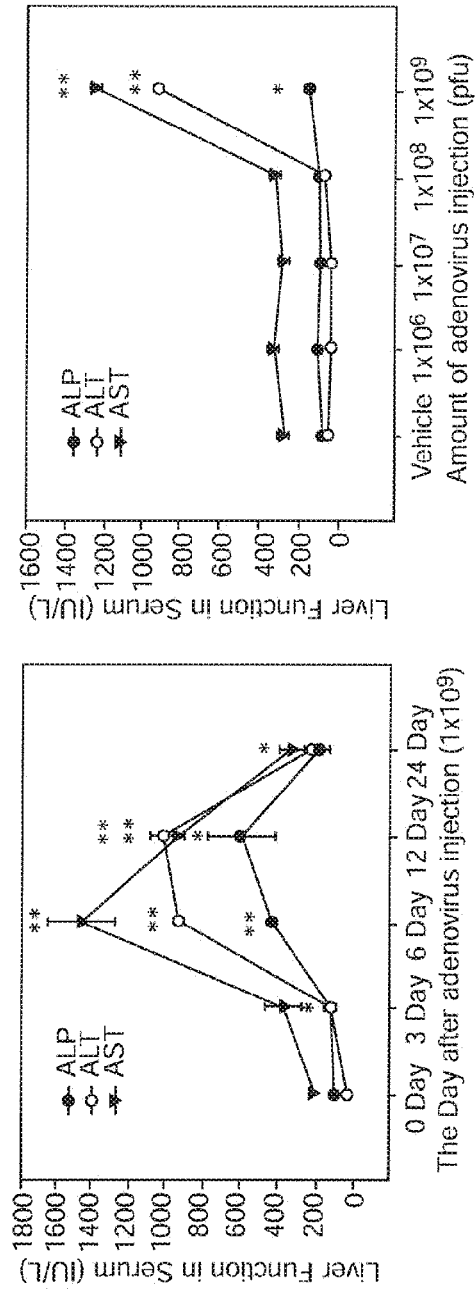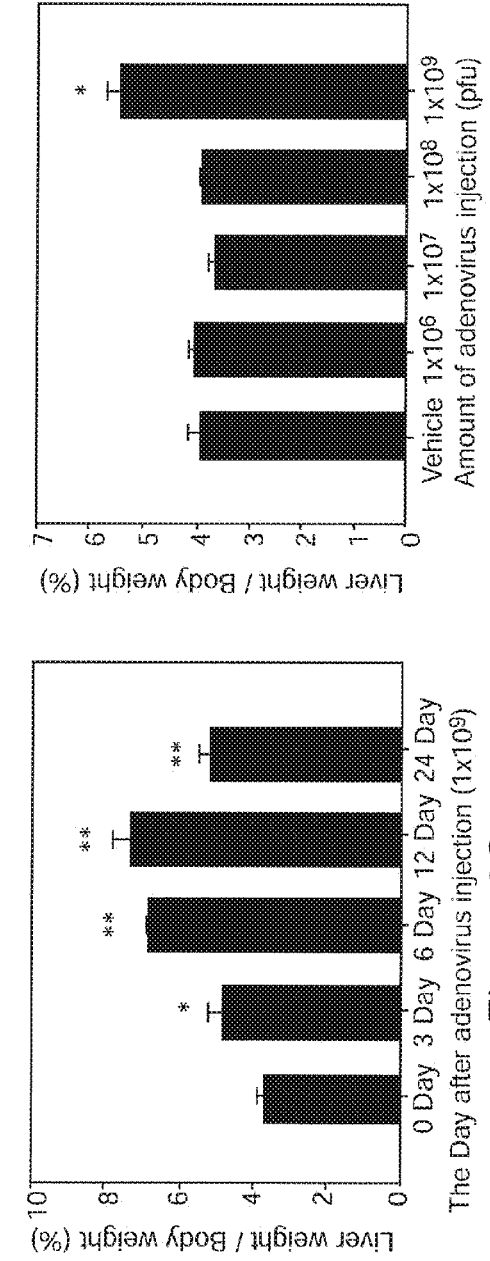
Figure 6A
Figure 6B
Figure 6C
Figure 6D

Relative Hepatic protein Expression in C57BL/6 Mice or LDLR-/- Mice after infection with β-Gal control or SULT2B1b virus

| | Wide Type_HCD | | Wide Type_HCD + 25HC | | LDLR-/-Mouse_HFD | |
|---|---|---|---|---|---|---|
| | Control | SULT | Control | SULT | Control | SULT |
| Nuclear protein | | | | | | |
| LXRalpha | 1.0 ± 0.32 | 0.54 ± 0.19 | 1.0 ± 0.20 | 0.68 ± 0.06 * | 1.0 ± 0.15 | 0.51 ± 0.13 ** |
| SREBP-1 Mature | 1.0 ± 0.23 | 0.35 ± 0.07 * | 1.0 ± 0.38 | 0.28 ± 0.11 * | 1.0 ± 0.15 | 0.55 ± 0.07 ** |
| SREBP-2 Mature | 1.0 ± 0.16 | 0.86 ± 0.03 | 1.0 ± 0.14 | 0.81 ± 0.17 | 1.0 ± 0.16 | 0.65 ± 0.07 * |
| Cytosol | | | | | | |
| ACC-1 | 1.0 ± 0.34 | 0.54 ± 0.13 * | 1.0 ± 0.20 | 0.40 ± 0.03 * | 1.0 ± 0.35 | 0.81 ± 0.03 |
| FAS | 1.0 ± 0.11 | 0.49 ± 0.02 ** | 1.0 ± 0.18 | 0.58 ± 0.14 * | 1.0 ± 0.08 | 0.54 ± 0.17 ** |
| SREBP-1 Precursor | 1.0 ± 0.15 | 0.81 ± 0.01 * | 1.0 ± 0.21 | 0.50 ± 0.07 ** | 1.0 ± 0.09 | 0.82 ± 0.10 * |
| SULT2B1b | 1.0 ± 0.10 | 3.04 ± 0.45 ** | 1.0 ± 0.07 | 8.78 ± 2.43 ** | 1.0 ± 0.08 | 2.53 ± 0.78 * |

Values are mean SD; * $P < 0.05$, ** $P < 0.01$ vs Control

*Figure 11B*

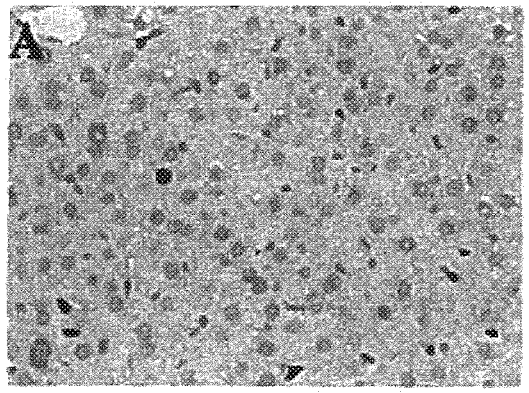
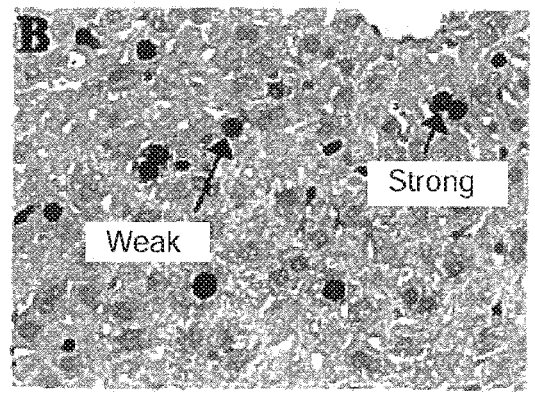
Figure 14A            Figure 14B
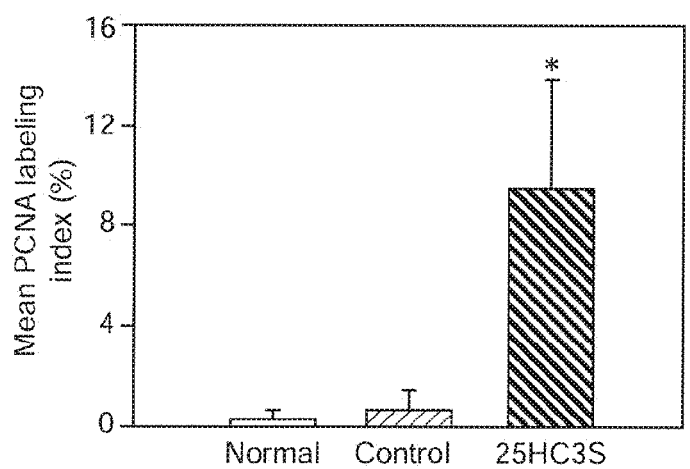
Figure 14C

Days following Infection

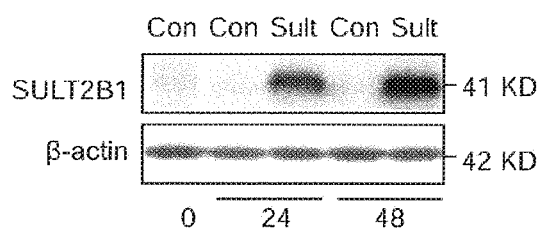
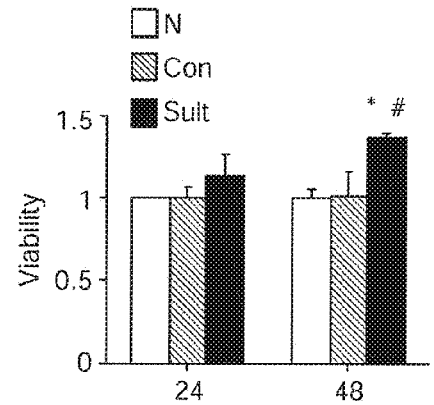
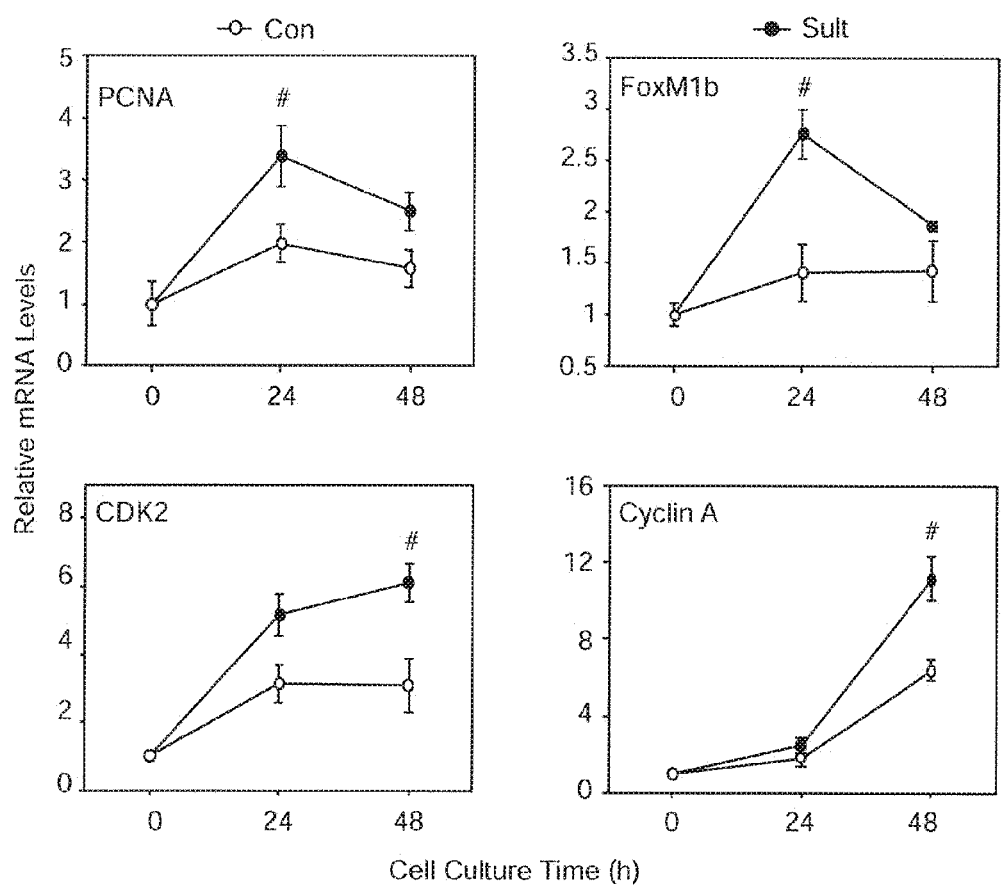
Figure 25A
Figure 25B
Figure 25C

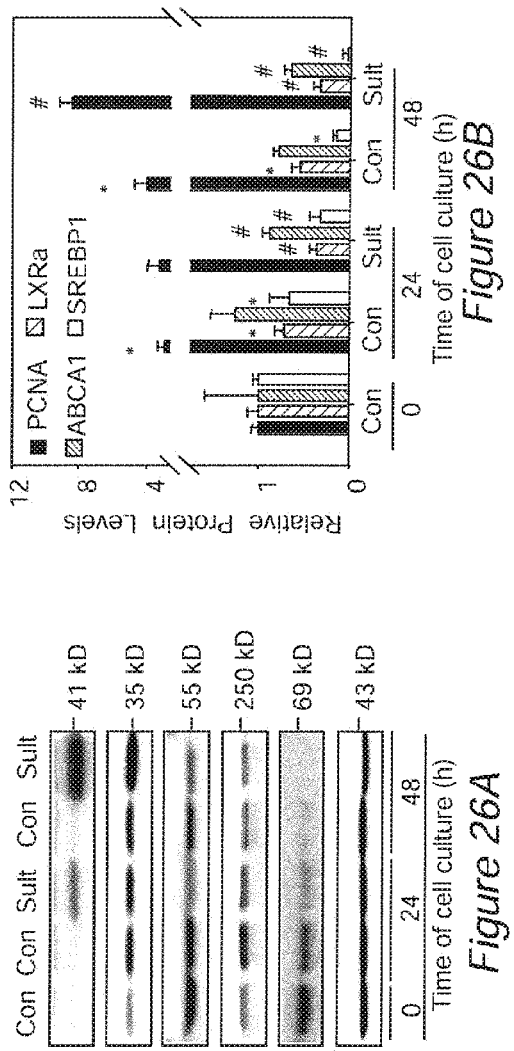
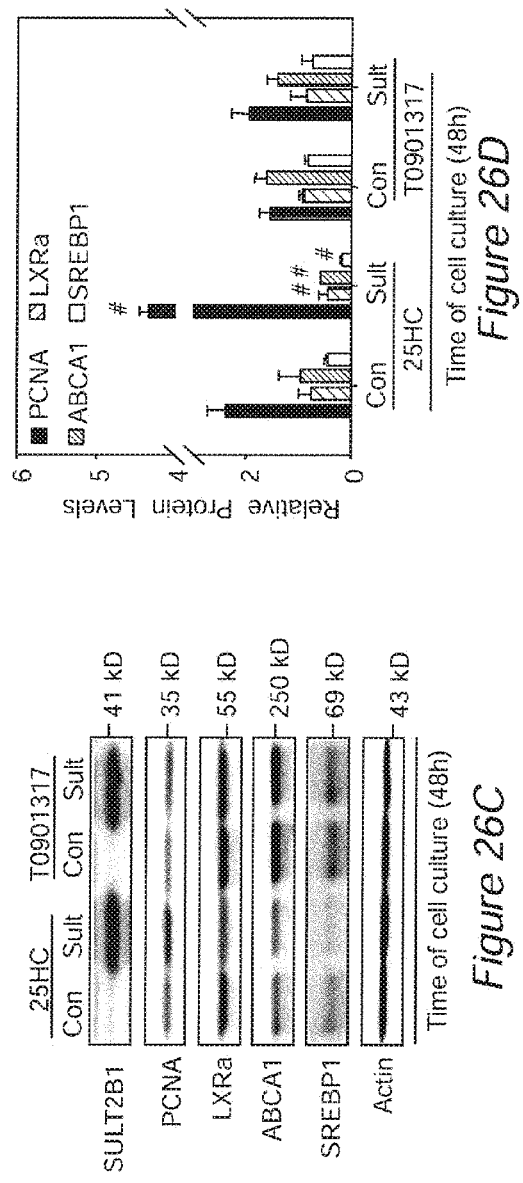
Figure 26A
Figure 26B
Figure 26C
Figure 26D

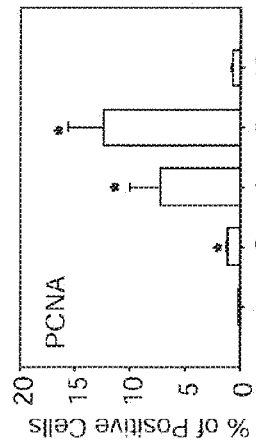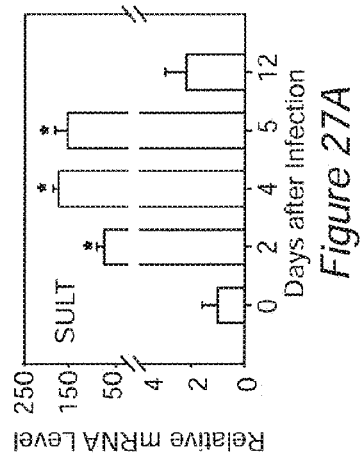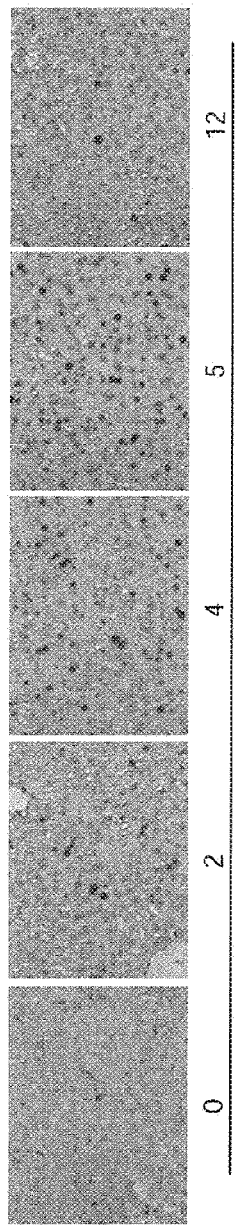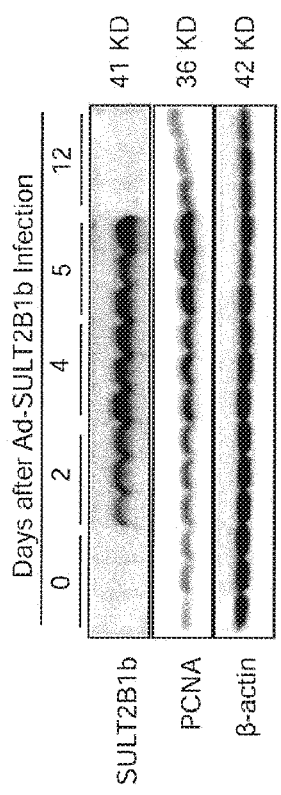
Figure 27A
Figure 27B
Figure 27C
Figure 27D

SULFATED OXYSTEROL AND OXYSTEROL SULFATION BY HYDROXYSTEROL SULFOTRANSFERASE PROMOTE LIPID HOMEOSTASIS AND LIVER PROLIFERATION

The present application claims priority under 35 U.S.C. §119(e) of U.S. Provisional Application No. 61/472,293, filed Apr. 6, 2011, and U.S. Provisional Application No. 61/604,711, filed Feb. 29, 2012, the complete disclosures of both of which are expressly incorporated by reference herein in their entirety. The present application also expressly incorporates by reference herein the entire disclosure of U.S. Application Nos. 20070275939, filed Apr. 24, 2007, and 20100273761, filed Feb. 19, 2010

This invention was made with government support under contract number R01 HL078898 awarded by the National Institutes of Health. The government has certain rights in the invention.

BACKGROUND OF THE INVENTION

Field of the Invention

The invention generally relates to the prevention and treatment of liver disease or damage. In particular, the invention provides methods of providing the sulfated oxysterol 25-hydroxycholesterol-3-sulfate (25HC3S) to a subject in order to prevent or treat liver disease or damage such as nonalcoholic fatty liver disease (NAFLD), to facilitate recovery after hepatectomy surgery and to promote lipid homeostasis.

Background of the Invention

The liver is a vital organ present in vertebrates and some other animals. This organ plays a major role in metabolism and has a number of functions in the body, including glycogen storage, decomposition of red blood cells, plasma protein synthesis, hormone production, the maintenance of lipid homeostasis, detoxification, and production of biochemicals necessary for digestion. As a result of the wide-ranging and vital functions of this organ, subjects with liver disease or damage can experience drastic and debilitating health consequences. Although liver dialysis can be used in the short term, there is currently no way to compensate for the long term absence of liver function.

Damage to the liver can occur due to and/or be associated with a variety of factors such as exposure to various toxins, excessive consumption of alcohol, obesity, high fat diets, viral infections, hereditary factors, cancer, the long-term use of certain medications, trauma as the result of an accident or combat, etc. One particular liver disease that is currently of major concern is nonalcoholic fatty liver diseases (NAFLD). NAFLD is characterized by the accumulation of lipids (e.g. triglycerides) in liver tissue. This syndrome is associated with obesity and is currently estimated to affect almost one-quarter of the general United States population. The spectrum of NAFLD ranges from simple nonprogressive steatosis to progressive steatohepatitis (NASH) that is characterized by inflammation and results in liver cirrhosis and hepatocellular carcinoma. Lowering triglyceride levels and anti-inflammatory responses are important elements of successful NAFLD prevention and therapy. However, this option is unlikely to be adopted by many individuals in the developed world. A large number of medical treatments for NAFLD have been studied and, while many appear to improve biochemical markers such as alanine transaminase levels, most have not been shown to reverse histological abnormalities or reduce clinical endpoints.

Currently, the only long-term option for treating severe liver damage is liver transplantation, which may involve receipt of an entire organ from a deceased donor, or receipt of a lobe or liver tissue donated by a live donor. While transplantation can be successful, especially in view of the compensatory growth capabilities of liver tissue, the procedure is drastic, requiring major surgery and subsequent monitoring and treatment to avoid rejection.

There is obviously a need in the art to develop techniques to prevent or treat liver damage such as that which results from NAFLD, or from other causes, and to promote lipid homeostasis.

SUMMARY OF THE INVENTION

The present invention provides methods and compositions for use in the prevention and/or treatment of liver disease and damage in subjects in need thereof. The methods involve increasing the level of the cholesterol metabolite, 25-hydroxycholesterol-3-sulfate (5HC3S) in the subject. In some embodiments, 25HC3S is increased (elevated) by direct administration of the compound to the subject. In other embodiments, 25HC3S is increased indirectly by overexpression, in the subject, of the hydroxysterol sulfotransferase enzyme SULT2B1b, which catalyzes the sulfation of the endogenous substrate 25-hydroxycholesterol (25HC) to form 25HC3S. This second embodiment may optionally also comprise administering exogenous 25HC substrate to the subject.

As described above, the liver is responsible for the maintenance of lipid homeostasis in the body, and the active agents that are administered as described herein appear to act principally on the liver. As such, the compounds may be used to both prevent and treat disease and damage of the liver per se (e.g. NAFLD), and to prevent and treat diseases associated with excessively high levels of circulating lipids, i.e. prevent or treat hyperlipidemia and associated disorders such as artherosclerosis.

In one or more aspects, the invention involves a method for promoting liver cell proliferation or liver tissue regeneration in a subject, comprising: elevating a level of 25-hydroxycholesterol-3-sulfate (25HC3S) in a subject in need of at least one of liver cell proliferation and liver tissue regeneration in order to promote proliferation of liver cells or regeneration of liver tissue in said subject. In one embodiment, elevating a level of 25HC3S is performed by administration of exogenous 25HC3S to said subject. In one embodiment, 25HC3S is administered in an amount ranging from 0.1 mg/kg to 100 mg/kg, based on body mass of said subject. In another embodiment, 25HC3S is administered in an amount ranging from 1 mg/kg to 10 mg/kg, based on body mass of said subject. In other embodiments, administration comprises at least one of oral administration, enteric administration, sublingual administration, transdermal administration, intravenous administration, peritoneal administration, parenteral administration, administration by injection, subcutaneous injection, and intramuscular injection. In another embodiment, elevating a level of 25HC3S is performed by providing hydroxycholesterol sulfotransferase 2B1b (SULT2B1b) and 25-hydroxycholesterol (25HC) to said subject. In yet other embodiments, elevating a level of 25HC3S is performed by promoting overexpression of SULT2B1b in said subject and providing 25HC to said subject. In some embodiments, elevating is performed before, during or after liver surgery in said subject. In one embodiment, the liver surgery comprises liver transplant surgery. In other embodiments, the subject has at least one of cirrhosis, liver injury, and hepatitis. In yet other embodiments, elevating is performed using a viral vector comprising a nucleic acid sequence coding for SULT2B1b.

The invention further involves a method for promoting liver regeneration, comprising: administering to a subject a nucleic acid sequence coding for SULT2B1b, wherein said administering is performed such that said nucleic acid sequence is selectively expressed in liver cells in said subject. In one embodiment, administering is performed before, during or after liver surgery in said subject. In another embodiment, the liver surgery comprises liver transplant surgery. In yet other embodiments, the subject has at least one of cirrhosis, liver injury, and hepatitis. In some embodiments of the invention, administering is performed using a viral vector.

The invention also involves a method for treating or preventing hyperlipidemia or fatty liver disease or malady resulting from hyperlipidemia or fatty liver disease, comprising: providing a subject with a sufficient amount of a sulfotransferase to elevate endogenous levels of 25HC3S in said subject, wherein said elevated endogenous levels of 25HC3S are sufficient to decrease lipid synthesis in said subject so as to reduce serum and hepatic lipid levels in said subject, or to reduce one or more regulators of lipid metabolism in said subject. In one embodiment, the sulfotransferase is SULT2B1b. In some embodiments, providing is performed by administering said subject a nucleic acid sequence coding for SULT2B1b, wherein said administering is performed such that said nucleic acid sequence is expressed in liver cells in said subject. In other embodiments, the method also comprises administering 25HC to said subject. In yet other embodiments, administering is performed using a viral vector. In some embodiments, the hyperlipidemia is selected from hypercholestolemia and hypertrigyceridemia. In some embodiments, the fatty liver disease is non-alcoholic fatty liver disease. In other embodiments, the malady comprises at least one malady selected from atherosclerosis, stroke, gall stones, diabetes, inflammatory bowel disease, and non-alcoholic steatohepatitis. In some embodiments, administering is performed such that said nucleic acid sequence is selectively expressed in at least one of liver tissue, lung tissue, and aorta tissue in said subject.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The present invention is further described in the description of invention that follows, in reference to the noted plurality of non-limiting drawings, wherein:

FIG. 1A-F. Effects of 25HC3S and 25HC on the serum lipoprotein profile in HFD-fed mice. Eight-week-old C57BL/6J female mice were fed a high fat diet (HFD) for 10 weeks, treated with either 25HC3S, 25HC or vehicle twice and fasted over night, n=15-17. Serum lipoprotein profiles were separated by HPLC with a Superose 6 column (A and B), and each fraction was collected for the measuring of concentration of triglyceride (TG) (Panels C and D) and cholesterol (CHOL) (E and F). The data represent one of three separate experiments.

FIG. 3A-D. The effects of 25HC3S and 25HC on gene expressions in lipid metabolism in liver tissues. Animals were treated as described in FIG. 1. Specific protein levels in cytoplasmic and nuclear extracts were determined by Western blot analysis. A and C, protein levels of ACC1 and FAS normalized to β-actin; B and D, protein levels of SREBP1 and SREBP2 normalized to Lamin B1. All the values are expressed as mean±SD. The symbol # represents $p<0.05$ versus chow diet-fed vehicle-treated mice liver; * $p<0.05$ versus HFD-fed vehicle-treated mice liver; (n=3).

FIG. 5A-F. A long-term treatment with 25HC3S decreases lipid accumulation in liver tissue in mouse NAFLD models. Animals were treated as described in FIG. 4. Hepatic triglyceride (A); free fatty acid (B); total cholesterol (C); free cholesterol (D); and cholesterol ester (E) were measured. Each individual level was normalized by liver weight. All the values are expressed as mean±SD. # $p<0.001$ versus chow-fed vehicle-treated mice. * $p<0.05$ and ** $p<0.01$ versus HFD-fed vehicle-treated mice liver. In morphology studies (F), liver sections from chow diet fed (chow), high fat diet fed (HFD) and high fat diet fed with 25HC3S treated (HFD-25HC3S) mice were stained by H&E staining. Arrows indicate unstained lipid inclusions.

FIG. 6A-D. Effect of adenovirus infection on liver toxicity. C57BL/6 mice, 12w, were infected with Adenovirus through tail vein injection. Each group contains 3 mice. FIGS. 6A and B show the liver-specific cytosolic enzyme activities of alkaline phosphatase (ALP), alanine transaminase (ALT), and aspartate transaminase (AST) in serum of mice, and the ratio of liver weight to body weight 3, 6, 12, and 24 days after adenovirus injection ($1\times10^8$ pfu). FIGS. 6C and D show the ALP, ALT, and AST activities in the serum and the ratio of liver to body weight 6 days after injection with different amount adenovirus (0, $1\times10^6$, $1\times10^7$, $1\times10^8$, $1\times10^9$ pfu/mouse). * $P<0.05$, ** $P<0.01$ vs. 0 day or vehicle.

FIG. 14 A-C. Effect of exogenous 25HC3S on PCNA labeling index in mouse liver tissues. A, B and C show representative photomicrographs from PCNA-stained liver sections of normal mouse group (A), vehicle (PBS 10% ethanol, 48 h) group (B), and 25HC3S (5 mg/kg, 48 h) group; (C) PCNA labeling index obtained from liver sections of each group. The results are shown as mean±S.D. (n=3-5/group) * P<0.05 vs. Normal mouse group.

FIG. 25 A-C. Effect of SULT2B1b overexpression on proliferation in PRH. PRH at a confluency of 100% were infected with Ad-Control or Ad-SULT2B1b for 24 and 48 hours as indicated. (A) SULT2B1b protein level was determined via western blot analysis. (B) Relative hepatocyte viabilities were measured by cell survival assay. The OD value of cells cultured in normal (N) was arbitrarily assigned as 100%; (C) RTqPCR analysis of cell cycle regulatory gene mRNA levels, including CDK2, FoxM1b, cyclin A and PCNA. Data are the mean±S.D. of three determinations. *P<0.05 vs. N, #P<0.05 vs. Con.

FIG. 26A-D. Effect of SULT2B1b on proliferation via LXR signaling pathway in PRH. PRH at a confluency of 100% were infected with Ad-Control or Ad-SULT2B1b for 24 and 48 hours as indicated. (A and B) Western analysis of SULT2B1b, PCNA, LXRa, ABCA1 and SREBP1 protein levels; (C and D) 24 hours after infection, cells were treated with 25HC (3 µM) or T0901317 (1.5 µM) for another 24 hours, the protein levels of SULT2B1b, PCNA, LXR and its target genes ABCA1 and SREBP1 were analyzed by western blot. The data of western blot represent one of three separate experiments. Data are the mean±S.D. of three determinations. *P<0.05 vs. 0 hour, #P<0.05 vs. Con.

FIG. 27A-D. Effect of SULT2B1b overexpression on proliferating cell nuclear antigen (PCNA) in mouse liver Mice were infected with Ad-SULT2B1b (1×10[8] pfu) as indicated. Each group contained 3-5 mice. A: Relative mRNA level of SULT2B1b expression was measured by RTqPCR. B: Percentage number of PCNA-positive cells obtained from liver sections at the indicated time-points. C: Immunohistochemistry analysis of PCNA expression on liver sections (20× optical field) in mice with SULT2B1b infection. D: Western blot analysis of SULT2B1b and PCNA expression at protein levels. * Represents P<0.05 vs. time-point 0.

DETAILED DESCRIPTION

Figure 2:
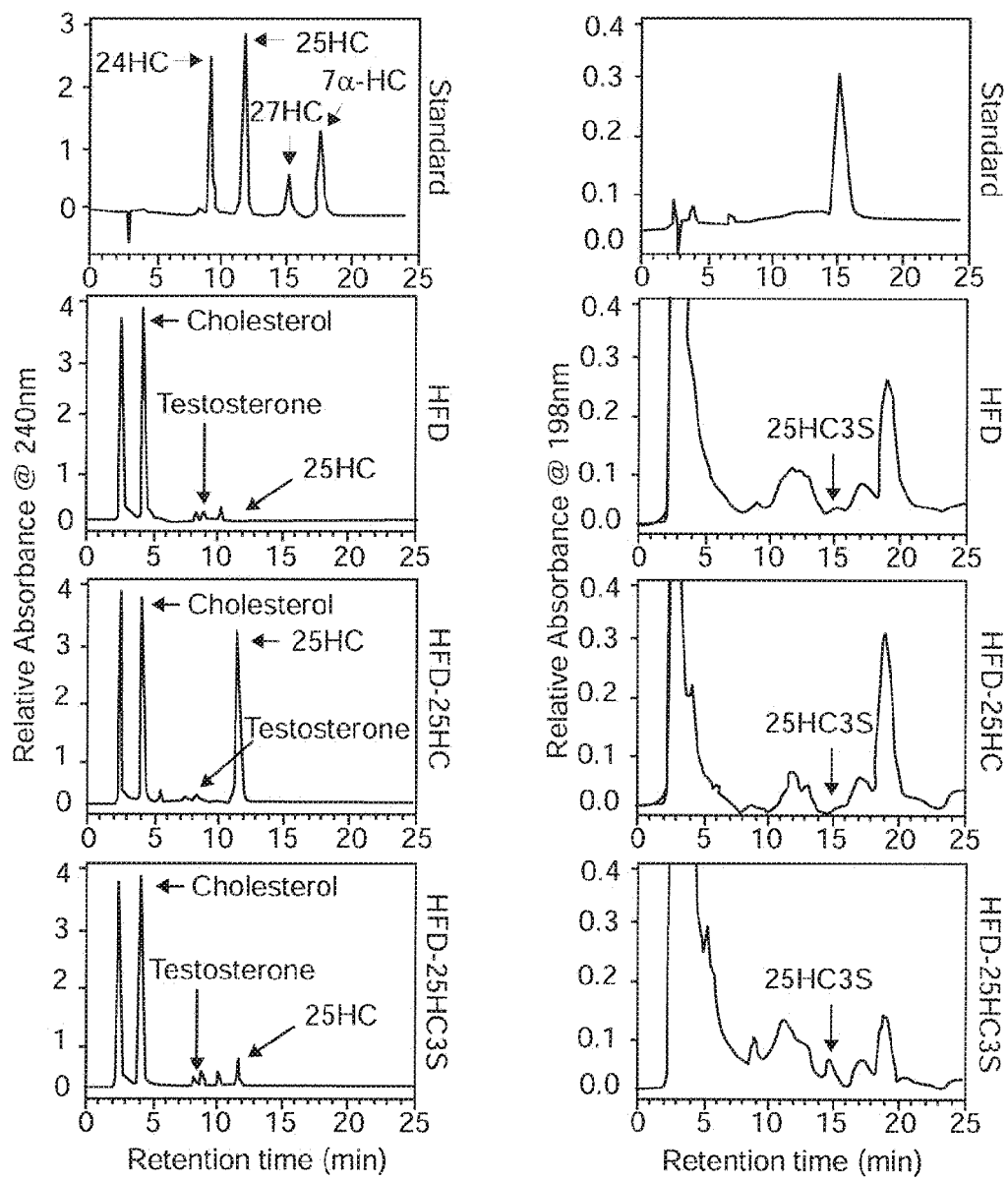
FIG. 2. HPLC Analysis of 25HC3S and 25HC levels in the treated mice liver tissues. Animals were treated as described in FIG. 1. Total neutral lipids were extracted with chloroform/methanol mixture and analyzed by HPLC. 24-hydroxycholesterol (24HC), 25-hydroxycholesterol (25HC), 27-hydroxycholesterol (27HC) and 7α-hydroxycholesterol (7α-HC) were used as standard controls; and testosterone in the chloroform phase was used as an internal control. Oxysterols in the chloroform phase from vehicle-treated, 25HC-treated, and 25HC3S-treated mouse liver were determined (Left panel). Chemical synthesis of 25HC3S was used as standard control in water/methanol phase. 25HC3S in water/methanol phase from vehicle-treated, 25HC-treated and 25HC3S-treated mice liver were determined (Right panel). The data represent one of three separate experiments.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

The present invention provides methods for preventing and/or treating liver damage or disease, and compositions for use in the methods. According to the invention, the sulfated oxysterol 25HC3S is provided to a subject who is experiencing or who is likely to experience a liver malady. Two basic methodologies for providing 25HC3S are encompassed. In one embodiment, the sulfated oxysterol compound 25HC3S is administered to the subject. In a second embodiment, a nucleic acid encoding the hydroxysterol sulfotransferase enzyme SULT2B1b is administered to the subject in a manner that results in overexpression of SULT2B1b in the subject. Overexpressed SULT2B1b catalyzes sulfation of the naturally occurring endogenous substrate 25HC within the subject, converting it to 25HC3S, thereby increasing the concentration of 25HC3S in the subject. Optionally, exogenous 25HC substrate may be administered to the subject in conjunction with administration of the nucleic acid. The invention may also encompass a treatment method in which both 25HC3S and a nucleic acid encoding SULT2B1b (with or without 25HC are administered.

The present invention also provides methods for preventing and/or treating lipidemia and/or diseases or damage associated with or caused by lipidemia. Without being bound by theory, the efficacy of the active agents described herein (e.g. 25HC3S, or agents which produce 25HC3S) re lowering lipids in serum and elsewhere appears to be related to the ability of the agents to influence liver function in a positive manner, augmenting the liver's ability to maintain proper lipid homeostasis.

By "25-hydroxycholesterol-3-sulfate (25HC3S)" we mean a compound of the structure:

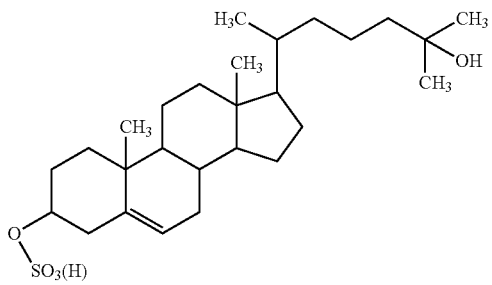

25HC3S is described in detail, for example, in published U.S. patent application US-1020-0273761 (Ren et al.), the complete contents of which is herein incorporated by reference in entirety.

The beneficial effects exerted by administration of the active agents described herein may include an increase in liver tissue re-growth or regeneration, and/or in an increase in total numbers of liver cells, and/or an increase in activity of liver cells, the increase either 1) occurring at a faster rate than would occur in the absence of the treatment; or 2) resulting in the production of more, or more physiologically active, liver cells than would occur in the absence of the increased amounts of 25HC3S. Alternatively, and/or in addition, the beneficial effect may be a decrease in lipid levels e.g. in serum, in liver cells, etc. of the subject Regardless of the parameter that is measured to detect the beneficial effect, the effect is typically an increase/decrease of at least about 10, 15, 20, 25, 30, 35, 40, 45, 50, 55, 60, 65, 70, 75, 80, 85, 90, 95 or even 100%, compared to a suitable control, e.g. a subject to whom the active agents described herein have not been administered. For example, the beneficial effect may be an increase in total liver weight or an increase is liver function of from about 10 to about 90%, compared to a control; or a decrease in total serum lipids of from about 10 to about 90%. In some embodiments, the increase or decrease is in the range of at least about 25 to 55%, or about 30 to 50%, or about 30 to about 45%.

In some embodiments, the invention encompasses a method of increasing a level of 25HC3S in a subject by providing the subject with the compound 25HC3S. In other embodiments, the invention encompasses a method of increasing a level of 25HC3S in a subject by providing the subject with the 25HC3S precursor 25HC. In yet other embodiments, the invention encompasses a method of increasing a level of 25HC3S in a subject by providing the subject with a translatable (expressable) nucleic acid sequence which encodes a SULT2B1b protein. Without being bound by theory, it is believed that administration of such a nucleic acid results in expression of the SULT2B1b in cells of the subject (e.g. liver cells), which in turn results in sulfation of 25HC to form 25HC3S in clinically relevant amounts, i.e. amounts of 25HC3S which have a beneficial effect on liver cells or tissue of the recipient. Optionally, and in addition, the SULT2B1b substrate 25HC may be administered to the subject with or in conjunction with the nucleic acid, e.g. in order to augment the amount of substrate available for sulfation by SULT2B1b.

The amino acid sequences of suitable SULT2B1b proteins and exemplary nucleic acids which encode them are readily accessible to those of skill in the art. For example, *Homo sapiens* SULT2B1b is available as GenBank No. NM-017465. An exemplary nucleic acid sequence encoding SULT2B1b is described, for example, in issued U.S. Pat. No. 7,820,805 (Thomae, et al.), the complete contents of which is hereby incorporated by reference. Further, those of skill in the art will recognize that the entire enzyme need not be translated. Rather, functional portions thereof (e.g. sections or portions of the enzyme which retain the ability to sulfate 25HC) may be utilized. In addition, chimeric proteins which include SULT2B1b or SULT2B1b activity may also be employed.

In some embodiments, what is administered is "naked" DNA encoding a SULT2B1b protein. However, in most embodiments, what is administered is a vector which comprises nucleic acid sequences which encode a SULTB1b protein, or an active form of the protein. Suitable vectors for use in the invention include but are not limited to various plasmids, cosmids, viral- and bacterial-based vectors, etc. Typically, the vector is a viral-based vector. A number of suitable viral based vectors are known in the art and have been used to successfully transfect mammalian cells. Among those are adenovirus, adenovirus-associated virus (AAV), papovaviruses, vacciniavirus, the insect-infecting baculovirus, and lentivirus, etc. The nucleic acid sequence that is utilized is typically operationally linked to at least one promoter sequence which drives expression of the enzyme. Addition sequences such as leader sequences may, enhancer sequences, etc. may also be included in such constructs. The constructs may selectively express SULT2B1b, e.g. in liver tissue, lung tissue, aorta tissue, etc. In some embodiments, selective expression may be due to the use of promoters that are selective for expression in particular types of cells or tissue. Techniques and guidelines for such gene therapy are described, for example, in "Present and future of adeno associated virus based gene therapy approaches." Recent Pat Endocr Metab Immune Drug Discov. 2012 January; 6(1), 47-66. "Gene Delivery System: A Developing Arena of Study for the New Era of Medicine" Recent Pat DNA Gene Seq. 2010 January 2 [Epub ahead of print]. "Nanoparticles in Gene Therapy Principles, Prospects, and Challenges". Prog Mol Biol Transl Sci. 2011; 104:509-62.

In the embodiment which involves administration of both a nucleic acid encoding SULT2B1b plus the substrate or precursor 25HC, these two entities (which may both be referred to as "active agents" herein) are administered "in conjunction with" one another, by which we mean that they may be administered, for example, in a single composition, or as separate compositions but at the same time or nearly the same time (e.g. within minutes or hours or one another). Alternatively, the two may be administered in conjunction with each other if they are administered in any coordinated manner, e.g. the nucleic may be administered first and, several hours or a few days later, the substrate may be administered; or the substrate may be administered first in order to "prime" or "load" the subject's system in readiness for substrate catalysis of the expressed enzyme several hours or days later, etc. The details and precise timing or scheduling is generally determined by skilled medical personnel on a case by case basis, with precedent being provided by data obtained from clinical trials.

Liver disorders that may be treated by the methods and compositions of the invention include but are not limited to: hepatitis, inflammation of the liver, caused mainly by various viruses but also by some poisons (e.g. alcohol); autoimmunity (autoimmune hepatitis) or hereditary conditions; nonalcoholic fatty liver disease, a spectrum in disease, associated with obesity and characterized by an abundance of fat in the liver, which may lead to hepatitis, i.e. steatohepatitis and/or cirrhosis; cirrhosis, i.e. the formation of fibrous scar tissue in the liver due to replacing dead liver cells (the death of liver cells can be caused, e.g. by viral hepatitis, alcoholism or contact with other liver-toxic chemicals); haemochromatosis, a hereditary disease causing the accumulation of iron in the body, eventually leading to liver damage; cancer of the liver (e.g. primary hepatocellular carcinoma or cholangiocarcinoma and metastatic cancers, usually from other parts of the gastrointestinal tract); Wilson's disease, a hereditary disease which causes the body to retain copper; primary sclerosing cholangitis, an inflammatory disease of the bile duct, likely autoimmune in nature; primary biliary cirrhosis, an autoimmune disease of small bile ducts; Budd-Chiari syndrome (obstruction of the hepatic vein); Gilbert's syndrome, a genetic disorder of bilirubin metabolism, found in about 5% of the population; glycogen storage disease type II; as well as various pediatric liver diseases, e.g. including biliary atresia, alpha-1 antitrypsin deficiency, alagille syndrome, and progressive familial intrahepatic cholestasis, etc. In addition, liver damage from trauma may also be treated, e.g. damage caused by accidents, gunshot wounds, etc. Further, liver damage caused by certain medications may be prevented or treated, for example, drugs such as the antiarrhythmic agent amiodarone, various antiviral drugs (e.g. nucleoside analogues), aspirin (rarely as part of Reye's syndrome in children), corticosteroids, methotrexate, tamoxifen, tetracycline, etc. are known to cause liver damage.

In one embodiment, the methods are performed before, during or after liver surgery in a subject. For example, the liver surgery may be liver transplant surgery and the subject that is treated may be a donor or a recipient; or the liver surgery may be surgery that removes disease or damaged liver tissue, or that removes cancerous tumors, etc.

In some embodiments, the disease or condition that is prevented or treated is or is caused by hyperlipidemia. By "hyperlipidemia" we mean the condition of abnormally elevated levels of any or all lipids and/or lipoproteins in the blood. Hyperlipidemia includes both primary and secondary subtypes, with primary hyperlipidemia usually being due to genetic causes (such as a mutation in a receptor protein), and secondary hyperlipidemia arising from other underlying causes such as diabetes. Lipids and lipid composites that may be elevated in a subject and lowered by the treatments described herein include but are not limited to chylomicrons, very low-density lipoproteins, intermediate-density lipoproteins, low-density lipoproteins (LDLs) and high-density lipoproteins (HDLs). In particular, elevated cholesterol (hypercholesteremia) and triglycerides (hypertriglyceridemia) are known to be risk factors for blood vessel and cardiovascular disease due to their influence on atherosclerosis. Lipid elevation may also predispose a subject to other conditions such as acute pancreatitis. The methods of the invention thus may also be used in the treatment or prophylaxis of conditions that are or are associated with elevated lipids, that include, for example, but are not limited to hyperlipidemia, hypercholesterolemia, hypertriglyceridemia, fatty liver (hepatic steatosis), and metabolic syndrome cardiovascular diseases, coronary heart disease, atherosclerosis, acute pancreatitis, various metabolic disorders, such as insulin resistance syndrome, diabetes, polycystic ovary syndrome, fatty liver disease, cachexia, obesity, atherosclerosis, arteriosclerosis, stroke, gall stones, inflammatory bowel disease, and the like. In addition, various conditions associated with hyperlipidemia include those described in issued U.S. Pat. No. 8,003,795 (Liu, et al) and U.S. Pat. No. 8,044,243 (Sharma, et al), the complete contents of both of which are herein incorporated be reference in entirety.

Methods of treatment include administering to a subject in need thereof a therapeutically effective amount of at least one compound, active agent or composition described herein. The compounds and/or active agents may include one or more of 25HC, 25HC3S and/or nucleic acids encoding SULT2B1b or an enzymatically active form thereof. The nucleic acids may be housed in a vector as described herein. The compounds of the invention can be used in the treatment or prophylaxis of a disease state or malady characterized by liver disease or damage, or associated with elevated plasma and/oror hepatic cholesterol or triglycerides. Generally, prophylactic or prophylaxis relates to a reduction in the likelihood of the patient developing a disorder such as cirrhosis, hyperlipidemia, hypercholesterolemia, hypertriglyceridemia, fatty liver, or metabolic syndrome or proceeding to a diagnosis state for the disorder. For example, the compounds of the invention can be used prophylactically as a measure designed to preserve health and prevent the spread or maturation of disease in a patient. It is also appreciated that the various modes of treatment or prevention of a disease such as liver disease, hyperlipidemia, hypercholesterolemia, hypertriglyceridemia, fatty liver, metabolic syndrome, etc. can mean "substantial" treatment or prevention, which includes total but also less than total treatment or prevention, and in which some biologically or medically relevant result is achieved. Furthermore, treatment or treating as well as alleviating can refer to therapeutic treatment and prophylactic or preventative measures in which the object is to prevent, slow down (lessen) a disease state, condition or malady. For example, a subject can be successfully treated for hypercholesterolemia if, after receiving through administration an effective or therapeutic amount of one or more active agents described herein, the subject shows observable and/or measurable reduction in or absence of one or more signs and symptoms of the particular disease such as, but not limited to, improved liver function, increased weight of liver tissue, increased number of liver cells, reduced plasma total cholesterol, reduced plasma LDL-cholesterol, increased hepatic expression of LDL receptor (LDLR), reduced plasma triglycerides, reduced morbidity and mortality, or improvement in quality of life issues.

The methods of the invention may also include a step of identifying a subject that is in need of the treatments described herein, e.g. a subject who has symptoms of or is at risk of developing one of the diseases or conditions described herein. Such a subject may be identified using any of the many testing or diagnostic methods that are known, for example, by measuring/detecting raised triglycerides (e.g. triglyceride levels >150 mg/dL [1.7 mmol/L]), or by measuring/detecting reduced HDL cholesterol (e.g. <40 mg/dL [1.03 mmol/L] in males, and <50 mg/dL [1.29 mmol/L] in females), by measuring/detecting raised blood pressure (e.g. systolic BP>130 or diastolic BP>85 mm Hg), or by measuring/detecting raised fasting plasma glucose (FPG) (e.g. FPG>100 mg/dl [5.6 mmol/L]), or by measuring/detecting body mass index (BMI) (e.g. a BMI>30 kg/m$^2$); or by measuring liver function e.g. by determining various enzymes, etc. that are indicators of liver function, examples of which include but are not limited to test for albumin, alanine transaminase, aspartate transaminase, alkaline phosphatase, bilirubin, 5' nucleotidase (5'NTD)5', lactate dehydrogenase, tests for coagulation and serum glucose, etc. A subject who is positive for one or more of these indicators may be a candidate for receipt of the treatments described herein. Those of skill in the art will recognize that a medical professional will typically make a diagnosis based on a constellation or collection of symptoms that are present in an individual patient.

The present invention provides compositions for use in promoting liver healing and regeneration, in lowering lipid levels, and/or in suppressing inflammatory responses e.g. lipid levels in blood or serum. In one embodiment, the compositions include substantially purified 25HC3S as described herein, and a pharmacologically suitable (physiologically compatible) carrier. In another embodiment, the compositions include substantially purified vector containing nucleic acid sequences that encode a SULT2B1b protein, or active form thereof and a pharmacologically suitable (physiologically compatible) carrier. In one embodiment, the compositions include substantially purified 25HC as described herein, and a pharmacologically suitable (physiologically compatible) carrier. The preparation of compositions suitable for administration for both embodiments is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active agent in the formulations may vary. However, in general, the amount in the formulations will be from about 1-99%.

The compounds of the present invention may be obtained from various sources. For example, 25HC is readily commercially available, e.g. from Research Plus, Inc. (Baynone, N.J.) or may be synthesized as described, for example by Ogawa (Steroids: 74 (2009) 81-87. 25HC3S may be synthesized, for example, as described herein (see Example 1), or as described in published United States patent applications 20070275939 and 20100273761 (Ren), the complete contents of both of which are hereby incorporated by reference in entirety.

The 25HC3S and/or 25HC compositions (preparations) of the present invention may be administered by any of the many suitable means which are well known to those of skill in the art, including but not limited to by injection (e.g. either systemically or via targeted injection into or into the vicinity of the liver), intravenously, inhalation, orally, intravaginally, intranasally, by ingestion of a food product containing the active agent, topically, by direct application to liver tissue after resection but before closing the surgical wound, etc. In preferred embodiments, the mode of administration is by injection or intravenously. In addition, the compositions may be administered in conjunction with other treatment modalities such as substances that boost the immune system, various chemotherapeutic agents, antibiotic agents, growth factors, and the like. The amount of 25HC3S to be administered may vary depending on characteristics of the subject to whom it is administered (for example, the species, gender, age, genetic makeup, general health, etc.), as well as the disease or condition that is being treated. However, the amount will generally be in the range of from about 0.1 mg/kg to about 100 mg/kg, based on body mass of the subject. In some embodiments, the amount ranges from about 1 mg/kg to about 10 mg/kg, based on body mass of the subject.

Similarly, the compositions which comprise a nucleic acid bearing vector may be administered by any of the many suitable means which are well known to those of skill in the art, including but not limited to by injection, orally, intranasally, transcutaneously, intravenously, intraperitoneally, subcutaneously, intramuscularly, by inhalation, etc. In addition, these compositions may also be administered alone or in combination with other medicaments as described above for 25HC3S compositions. If the vector is a viral vector, the dosage employed may generally be about $10^3$ to $10^{11}$ viable organisms, preferably about $10^3$ to $10^9$ viable virus particles (or pfu), as described (Shata et al., Vaccine 20:623-629 (2001); Shata and Hone, J. Virol. 75:9665-9670 (2001)).

Subjects to whom the compositions of the invention are administered are generally mammals. In some embodiments, the mammal is a human. In other embodiments, the subject is a non-human mammal, e.g. a companion pet, or other non-human animal that could benefit from the therapy.

The present invention will be further illustrated by way of the following Examples. These examples are non-limiting and do not restrict the scope of the invention. Unless stated otherwise, all percentages, parts, etc. presented in the examples are by weight.

EXAMPLES

The Examples provided below described the relationships among 25HC, 25HC3S SULT2B1b and other moieties that are active in the liver. The Examples also provide experimental evidence of the in vivo efficacy of the methods, as follows: I) the reduction/reversal of diet-induced serum and hepatic lipid accumulation in a mouse model of NAFLD is described in Examples 1 and 2. In Example 1, the reduction results from the administration of 25HC3S; in Example 2, the reduction results from the overexpression of SULT2B1b. II) the promotion of hepatic proliferation in a mouse model is described in Examples 3 and 4. In Example 3, proliferation results from the administration of 25HC3S; in Example 4, proliferation results from the overexpression of SULT2B1b. Example 5 describes the promotion of liver regeneration after partial hepatectomy as a result of overexpression of SULT2B1b.

The following abbreviations are used in the Examples: 25HC, 25-hydroxycholesterol; 27HC, 27-hydroxycholesterol; 25HC3S, 25-hydroxycholesterol-3-sulfate, also known as 5-cholesten-3β, 25-diol 3-sulfate; ABCA(G): ATP-binding cassette, sub-family A(G); ACC1: acetyl-CoA carboxylase 1; ACOX1: acyl-CoA oxidase 1; Ad-Control, adenovirus encoding β-Gal; Ad-SULT2B1b, adenovirus encoding SULT2B1b; AP, alkaline phosphatase; ALT, alanine transaminase; AST, aspartate transaminase; CDC25, cell division cycle 25; CDC25b, cell division cycle 25b; CDKs, cyclin-dependent kinases; cDNA, Complementary DNA; CPT1: carnitine palmitoyltransferase 1; CYP7A1, cholesterol-7α-hydroxylase; CYP27A1: mitochondrial cholesterol 27-hydroxylase; FABP1: fatty acid binding protein; FAS: fatty acid synthase; FATP: fatty acid transport protein; FoxM1b, Forkhead Box m1b; G6 Pase: glucose-6-phosphatase; GCK: glucokinase; GPAM: glycerol-3-phosphate acyltransferase HCD: high cholesterol diet; HFD: high fat diet; HMGR: 3-hydroxy-3-methylglutaryl-coenzyme a reductase; % IC/g, percentage of injected counts per gram of tissue; IL: interleukin; IκBα: nuclear factor of kappa light polypeptide gene enhancer in B-cells inhibitor, alpha; i.p., intraperitonealy; i.v., intravenously; LDLR: low-density lipoprotein receptor; LXR, liver X receptor; MCAD: acyl-CoA dehydrogenase; MMP, matrix metalloproteinase; MOI, multiple of infection; mRNA, messenger RNA; MTTP: microsomal triglyceride transfer protein; NAFLD: nonalcoholic fatty liver disease; NASH: nonaclcoholic steatohepatitis; NFκB: nuclear factor of kappa light polypeptide gene enhancer in B-cells; PCK1: phosphoenolpyruvate carboxykinase 1; PCNA, proliferating cell nuclear antigen; Pk1r: pyruvate kinase; PLTP: phospholipid transfer protein; PPAR: peroxisome proliferator-activated receptor; PRH, primary rat hepatocytes; RT-PCR, Reverse-transcription polymerase chain reaction; RTqPCR, quantitative real-time PCR; SCD: stearoyl-CoA desaturase; SRB1: scavenger receptor class B, member 1; SREBP, sterol regulatory element binding protein; StarD1: steroidogenic acute regulatory protein, D1; SULT2B1b: sulfotransferase family, cytosolic, 2B, member 1b; siRNA, small interference RNA; TNFα tumor necrosis factor, alpha.

Example 1

Reversal of Diet-Induced Serum and Hepatic Lipid Accumulation by 5-cholesten-3β,25-diol 3-sulfate in Mouse Models of Nonalcoholic Fatty Liver Disease (NAFLD)

In mammals, sterol regulatory element-binding protein-1c (SREBP-1c) preferentially controls lipogenic gene expression; and regulates fatty acid and triglyceride homeostasis. Its role in fatty acid biosynthesis and the development of fatty liver disease is well documented.

Oxysterols act at multiple points in cholesterol homeostasis and lipid metabolism. The oxysterol receptor, LXR, is sterol regulated transcription factor of lipid metabolism. Activation of LXR stimulates the expression of cholesterol efflux and clearance through ABCA1 and ABCG5/8, but it also up-regulates the expression of SREBP-1c, which in turn regulates at least 32 genes involved in lipid biosynthesis and transport. Therefore, activation of LXR by synthetic ligands could reduce serum cholesterol levels to protect against atherosclerosis, but it also leads to hepatic steatosis and hypertriglyceridemia due to the induction of fatty acid and triglyceride synthesis through activation of SREBP-1c. Hepatocytes have a limited capacity to store fatty acids in the form of triglycerides. Once the capacity is exceeded, cell damage occurs. Excess amounts of intracellular free fatty acids trigger the production of reactive oxygen species (ROS), causing lipotoxicity and activation of inflammatory signaling pathways, which ultimately lead to apoptosis. Thus, a compound that specifically inhibits the SREBP-1c pathway without activating LXR should be a good target for NAFLD therapy.

The oxysterol, 5-cholesten-3β,25-diol 3-sulfate (25HC3S), which accumulates in hepatocyte nuclei following overexpression of the mitochondrial cholesterol delivery protein, StarD1, has been identified. This oxysterol is synthesized by sterol sulfotransferase SULT2B1b from 25-hydroxycholesterol (25HC) by oxysterol sulfation. Overexpression of SULT2B1b inactivates the response of LXRα to 25HC, and inhibits LXR target gene expressions, including SREBP-1c and ABCA1. However, over-expression of SULT2B1b or addition of exogenous 25HC3S decreases both SREBP-1 and SREBP-2 expression; blocks the SREBP-1c processing; represses the expression of key enzymes, including acetyl-CoA carboxylase-1 (ACC-1), fatty acid synthase (FAS) and 3-hydroxy-3-methylglutaryl-CoA reductase (HMGR), involved in lipid metabolism, subsequently decreasing neutral lipid and cholesterol levels. 25HC3S thus may act as a LXR antagonist and as a cholesterol satiety signal; suppressing fatty acid and triglyceride synthetic pathway via inhibition of LXR/SREBP signaling. Moreover, 25HC3S increases IκBα expression; blocks TNFα-induced IκBα degradation; and decreases nuclear NFκB levels. In contrast, 25HC acts in an opposite manner: inducing IκBα. degradation and nuclear NFκB accumulations. These results indicate that oxysterol sulfation is also involved in inflammatory responses and may represent a link between inflammatory pathways and the regulation of lipid homeostasis.

In the present study, we show that acute treatment with 25HC3S substantially decreases serum triglyceride and cholesterol levels, and long term treatment decreases lipid levels in liver tissues via LXR-SREBP-1c signaling pathway in mouse NAFLD models. These findings provide strong evidence that the oxysterol sulfation product, 25HC3S, is a potent regulator involved in lipid metabolism.

Materials and Methods

Chemical synthesis of 5-cholesten-3β, 25-diol 3-sulfate

A mixture of 25-hydroxycholesterol (6.5 mg, 0.016 mmol) was dissolved in dry pyridine (300 μl) and triethylamine-sulfur trioxide (3.5 mg, 0.019 mmol) was stirred at room temperature for 2 hours. The solvents were evaporated at 40° C. under nitrogen stream, and to the resulting syrup was added 100 ml of alkalined $CH_3OH$, pH 8.0. After the pellets were dissolved completely and filtered, the products were purified by HPLC using a C18 column with a gradient elution system. A binary system of solvent A (20% $CH_3CN$ in $H_2O$, v/v) and solvent B (20% $CH_3CN$ in $CH_3OH$, v/v) was used, beginning at 50% A and 50% B with an initial flow rate of 1 ml/min for 10 min, increasing to 100% B and increasing the flow rate linearly to 2 ml/min over a 30 min period, and followed by an additional isocratic period of 20 min. The total duration was 60 min. 25HC3S was obtained as its sodium salt (4.7 mg, 57%) and a white powder, and the structure characterized by MS and nuclear magnetic resonance (NMR) spectroscopy analysis (not shown).

Animal Studies

Animal studies were approved by Institutional Animal Care and Use Committee of McGuire Veterans Affairs Medical Center and were conducted in accordance with the Declaration of Helsinki, the Guide for the Care and Use of Laboratory Animals, and all applicable regulations. To examine the effect of 25HC3S on diet-induced lipid accumulation in sera and liver, 8-week-old female C57BL/6J mice (Charles River, Wilmington, Mass.) were randomly assigned to three groups: the first control group was fed a chow diet; the high fat diet (HFD) group was fed a HFD (Harlan Teklad, Madison, Wis.) containing 42% kcal from fat, 43% kcal from carbohydrate, 15% kcal from protein and 0.2% cholesterol; and the high cholesterol diet (HCD) group was fed a 2% cholesterol diet with 18% kcal from fat, 58% kcal from carbohydrate and 24% kcal from protein for 10 weeks, respectively. All mice were housed under identical conditions in an aseptic facility and given free access to water and food. At the end of each period, the mice were intraperitoneally injected with vehicle solution (ethanol/PBS; Vehicle), 25HC (25 mg/kg), or 25HC3S (25 mg/kg) for 2 times and fasted over night for acute treatment (n=15-17 for each group) or once every three days for 6 weeks (n=16 for each group) and fasted 5 hrs for long-term treatment; and blood samples were collected. Serum triglyceride, total cholesterol, high density lipoprotein-cholesterol, glucose, alkaline phosphatase (ALK), alanine aminotransferase (ALT), and aspartate aminotransferase (AST) were measured using standard enzymatic techniques in the clinical laboratory at McGuire Veterans Affairs Medical Center. Lipoprotein profiles in sera were analyzed by HPLC as following described.

HPLC Analysis Of Serum Lipoprotein Profiles

Mouse serum (100 µl) was injected on a Pharmacia Superose 6 HR 10/30 FPLC column and eluted with 0.2 ml/min 154 mM NaCl pH 8.0, 0.1 mM EDTA, wavelength 280 nm. Fractions were collected for 1.2 min each. The cholesterol assay was performed using 180 µl of each fraction plus 20 µl of a 10× solution of Wako Total Cholesterol E Reagent (Wako Chemicals USA, Richmond, Va.) in a 96 well plate, incubated at 37° C. and read at 595 nm. The triglyceride assay was performed using 2 µl of each fraction plus 200 µl of Infinity™ Triglycerides Reagent (Fisher Scientific, Pittsburgh, Pa.) in a 96 well plate, incubated at 37° C. for 5 minutes and read at 500 nm.

Histomorphology Analysis

For each mouse, three specimens from different regions of the liver were collected and fixed in 4% paraformaldehyde in 0.1 M phosphate buffer at room temperature overnight. The regions of the specimens were standardized for all mice. The paraffin-embedded tissue sections (4 µm) were stained with hematoxylin and eosin.

Quantification of Hepatic Lipids

Liver tissues were homogenized, and lipids were extracted with a mixture of chloroform and methanol (2:1), and filtered. The extracts, 0.2 ml, were evaporated to dryness and dissolved in 100 µl of isopropanol containing 10% of triton X-100 for cholesterol assay (Wako Chemicals USA, Richmond, Va.), the NEFA solution (0.5 g of EDTA-Na2, 2 g of Triton X-100, 0.76 ml of 1N NaOH, and 0.5 g of sodium azide/1, pH 6.5) for free fatty acid assay (Wako Chemicals USA, Richmond, Va.), or isopropanol only for triglyceride assay (Fisher Scientific, Pittsburgh, Pa.). All of the assays were performed according to the manufacturer's instructions, respectively. Each lipid concentration was normalized to liver weight.

Western Blot Analysis of Special Protein in Cytoplasmic and Nuclear Extraction

Liver tissues were homogenized, and cytoplasmic and nuclear fractions were extracted with NE-PER Nuclear and Cytoplasmic Extraction Kit (Fisher Scientific, Pittsburgh, Pa.). The expression levels of ACC1, FAS, SREBP-1 and SREBP-2 were detected with specific antibodies, where β-actin was used as loading controls for cytoplasmic fractions, and Lamin B1 was used as loading controls for nuclear fractions. Each positive band was quantified by Advanced Image Data Analyzer (Aida, Straubenhardt, Germany).

Quantitative Real-Time Polymerase Chain Reaction (q-RT-PCR) Analysis

Total RNA was isolated with SV Total RNA Isolation Kit (Promega, Madison, Wis.), which included DNase treatment. Total RNA, 2 µg, was used for the first-strand cDNA synthesis as recommended by the manufacturer (Invitrogen, Carlsbad, Calif.). Real-time RT-PCR was performed using SYBR Green as indicator on ABI 7500 Fast Real-Time PCR System (Applied Biosystems, Foster City, Calif.). All primer/probe sets for real-time PCR were TaqMan gene expression assays (Applied Biosystems, Foster City, Calif.). Amplifications of β-actin and GAPDH were used as internal controls. Relative messenger RNA (mRNA) expression was quantified with the comparative cycle threshold (Ct) method and was expressed as $2^{-\Delta\Delta Ct}$. Suitable primers were utilized.

Analysis of Hepatic Oxysterols and Oxysterol Sulfates by HPLC

Mouse liver samples (400 mg) were digested by 2 mg/ml of proteinase K in PBS (1 ml) at 50° C. for 12 hours. To the digests, 40 ml of chloroform:methanol=2:1 (v/v) was added and sonicated for 30 min. After being filtered the insoluble matter, 6 ml of water and 100 µl of 1 M-$K_2CO_3$ were added, shaken, and allowed to stand for about 3 hours for phase separation.

The water/methanol phase, which mainly contains sulfated oxysterols, was evaporated under $N_2$. The residues were re-suspended in 20% methanol by sonication and passed through a Sep-Pak tC18 cartridge (Waters, Milford, Mass.). After the cartridge was washed with 20% methanol, the sulfated oxysterol fractions were eluted with 60% methanol and taken to dryness under $N_2$ stream below 40° C. The extracts were then solvolyzed in a mixture of acetone (1 ml), methanol (9 ml), and conc. HCl (20 µl) at 39° C. for overnight. After neutralized by 5% KOH in methanol, 30 µl of testosterone in chloroform solution (50 µg/ml) was added, and evaporated to dryness. The residues were re-suspended in 8 ml of hexane. The mixture was loaded onto a Waters Sep-Pak silica cartridge (400 mg) that had been washed with 2% isopropanol in hexane. The purified oxysterols fractions were eluted with 8 ml of isopropanol:hexane (1:9, v/v) and evaporated under $N_2$.

The chloroform phase, which mainly contains non-sulfated oxysterols, was added 30 µl of testosterone in chloroform solution (50 µg/ml) and evaporated under $N_2$ below 40° C. The residue was re-suspended in 8 ml of hexane and passed through a Waters Sep-Pak silica cartridge to purify the oxysterol fraction as described above.

The oxysterol samples thus obtained from each phase, methanol/water phase and chloroform phase were derivatized to the corresponding 3-Keto-$\Delta^4$ form with cholesterol oxidase essentially according to the reported method (27), and were analyzed by Water Alliance series 2695 HPLC module fitted with 2487 Dual λ absorbance detector (Waters, Milford, Mass.). The separation was carried out on an Ultraspere silica column (5 µm, 4.6 mm id×250 mm; Beckman, Urbana, Ill.) and hexane:isopropanol:acetic acid=965:25:10 (by volume) as an eluent at a flow rate of 1.3 ml/min. The column temperature was kept constant at 30° C. and the enones were monitored at the absorption at 240 nm.

Statistical Analysis

All results were expressed as mean±standard deviation (SD). Western blot results were repeated at least three times. Statistical analysis was performed with the Student t test. The p<0.05 values were considered statistically significant.

Results

25HC3S Administration Reduces Serum Lipid Levels in Mice Fed a HFD and HCD.

To investigate the effects of 25HC3S on hyperlipidemia and hepatic steatosis in vivo, 8-week-old C57BL/6J female mice were fed a HFD to establish a NAFLD model. After 10 weeks of feeding, we treated these mice with 25HC3S, 25HC or vehicle twice in 14 hrs as acute treatment, and fasted the animals overnight. Caloric intake and weight gain were similar in all treated groups. As expected, in HFD group, compared to the vehicle treatment, the acute treatment with 25HC3S significantly decreased plasma triglyceride and cholesterol levels induced by HFD (Table 1). Plasma triglyceride levels were reduced compared to those seen in healthy chow diet-fed mice (Table 1). In contrast, 25HC significantly increased plasma cholesterol levels and did not change plasma triglyceride levels (Table 1). The fasting serum glucose level was compared with those in chow-fed mice (Table 1). Interestingly, 25HC significantly decreased fasting glucose levels which were elevated by HFD, whereas 25HC3S had no effect. These results were further confirmed in the HCD group where plasma triglyceride levels were significantly decreased by the acute treatment with 25HC3S (Table 1).

Liver function analysis showed that HFD raised serum ALT and AST levels. 25HC treatment significantly increased the levels further (Table 1). In contrast, there was no significant difference between 25HC3S-treated and vehicle-treated mice (Table 1). These results indicate 25HC induces liver inflammation, leading a rise of liver injury, whereas 25HC3S does not.

A high-performance liquid chromatography (HPLC) analysis of serum lipoprotein profiles showed that 25HC3S treatment did not change LDL, VLDL, and HDL protein levels (FIG. 1A) but markedly decreased triglyceride contents in VLDL fractions and slightly decreased cholesterol contents in HDL fractions (FIGS. 1C, E). In contrast, 25HC treatment significantly increased triglyceride contents in LDL fractions and cholesterol contents in LDL and HDL fractions (FIGS. 1D, F), consistent with Table 1. These results indicate that administration of 25HC3S lowers serum lipid levels by decreasing lipid biosynthesis. In contrast, administration of 25HC in mice significantly increases serum LDL particles by increasing lipid synthesis and blocking LDL uptake, subsequently increasing cholesterol and triglyceride accumulation in serum.

Analysis of 25HC3S or 25HC in Liver Tissues

To study the effects of 25HC3S or 25HC on hepatic lipid metabolism in HFD-fed mice, the concentration of 25HC3S or 25HC in the liver tissues from treated mice was determined by HPLC analysis. The results indicated that 25HC3S or 25HC treatment significantly increased the levels of these compounds in liver (FIG. 2). It was observed that a small peak of 25HC presented in 25HC3S-treated mice liver (FIG. 2) may indicate a small part of 25HC3S was degraded to 25HC by STS, which is expressed in the liver.

Hepatic mRNA Expression in the 25HC3S- or 25HC-Treated Mice

To compare the regulation of lipogenic gene expression in response to 25HC3S or 25HC treatment in liver, we determined the mRNA levels by real time RT-PCR as shown in Table. 2. 25HC3S treatment significantly decreased the mRNA levels of genes involved in fatty acid biosynthesis. Compared to vehicle-treated mice liver, 25HC3S reduced the mRNA levels of LXRα, SREBP-1c, ACCT and FAS by 20%, 45%, 45%, and 70%, respectively. In addition, 25HC3S significantly suppressed ABCA1 expression, which may explain the lower level of plasma HDL cholesterol (Table 1 and FIG. 1). In contrast, 25HC basically had the opposite effects: increasing fatty acid synthesis and decreasing fatty acid oxidation (Table 2). 25HC increased the mRNA levels of SREBP-1c, ACC1, and FAS by 170%, 160% and 150%, respectively; decreased the mRNA levels of PPARα, ACOX1 and SCD decreased by 40%, 55% and 40%, respectively (Table 2). In addition, 25HC increased SRB1 expression, which could cause an increase in oxidized LDL (oxLDL) uptake and inflammatory responses. These results may explain the higher levels of serum ALT and AST (Table 1). Interestingly, both 25HC and 25HC3S repressed CYP7α1 expression, which is the rate-limiting enzyme in bile acid synthesis, indicating that 25HC feeds back to inhibit the

TABLE 1

Serum Parameters of Mice Fed a HFD or HCD with or without 25HC or 25HC3S

| | Triglycerides (mg/dL) | Cholesterol (mg/dL) | HDL-C (mg/dL) | Glucose (mg/dL) | ALK (IU/L) | ALT (IU/L) | AST (IU/L) |
|---|---|---|---|---|---|---|---|
| Chow diet | 39 ± 5 | 57 ± 5 | 51 ± 5 | 196 ± 32 | 93 ± 15 | 32 ± 5 | 175 ± 11 |
| HFD | 53 ± 11*** | 106 ± 16*** | 90 ± 16*** | 245 ± 53* | 95 ± 41 | 46 ± 10** | 219 ± 50* |
| HFD + 25HC | 49 ± 13 | 144 ± 24## | 119 ± 21## | 188 ± 26## | 55 ± 12## | 56 ± 14# | 294 ± 57## |
| HFD + 25HC3S | 34 ± 9## | 87 ± 24# | 72 ± 26# | 245 ± 50 | 76 ± 21 | 47 ± 6 | 222 ± 54 |
| HCD | 57 ± 17** | 91 ± 12*** | 86 ± 10*** | 250 ± 38** | 94 ± 14 | 47 ± 7*** | 234 ± 46 |
| HCD + 25HC3S | 43 ± 8† | 86 ± 7 | 77 ± 7† | 249 ± 39 | 89 ± 19 | 44 ± 5 | 227 ± 48 |

C57BL/6J female mice were on each diet for 10 weeks and treated with 25HC or 25HC3S twice and fasted overnight. alues are mean ± SD; n = 15-17;
*p < 0.05,
**p < 0.01,
***p < 0.001,
p < 0.05,
p < 0.01,
p < 0.001 compared with HFD-fed vehicle-treated mice.
†p < 0.05 compared with HCD-fed vehicle-treated mice.

transcriptional level of CYP7α1. In addition, 25HC decreased the mRNA levels of glucokinase (GCK), pyruvate kinase (Pklr), and glucose 6-phosphatase (G6Pase), but not phosphoenolpyruvate carboxykinase 1 (PCK1) (Table 2), indicating that the decrease in serum glucose levels is due to the repression of hepatic glycolysis and gluconeogenesis (Table 1). It is interesting that 25HC increased SULT2B1b expression by 3-fold. This is in contrast to in vitro data where 25HC3S suppressed SULT2B1b mRNA level but 25HC has no effect. The present results show that 25HC increases SULT2B1b expression but 25HC3S has no effect. The mechanism is unknown.

TABLE 2

Relative Hepatic mRNA Expression in the Mice Fed a HFD with 25HC or 25HC3S

|  | HFD | HFD + 25HC | HFD + 25HC3S |
|---|---|---|---|
| Fatty acid biosynthesis |  |  |  |
| SREBP-1c | 1.02 ± 0.10 | 1.69 ± 0.75* | 0.56 ± 0.13** |
| ACC1 | 1.06 ± 0.27 | 1.58 ± 0.64* | 0.56 ± 0.12** |
| FAS | 1.07 ± 0.22 | 1.45 ± 0.18* | 0.33 ± 0.21** |
| LXRα | 1.03 ± 0.13 | 0.98 ± 0.09 | 0.79 ± 0.10* |
| FABP1 | 0.99 ± 0.23 | 0.48 ± 0.15** | 1.14 ± 0.45 |
| FATP | 1.10 ± 0.39 | 0.67 ± 0.12* | 1.05 ± 0.29 |
| Fatty acid oxidation |  |  |  |
| PPARα | 0.96 ± 0.27 | 0.59 ± 0.09* | 0.93 ± 0.35 |
| ACOX1 | 0.99 ± 0.23 | 0.45 ± 0.17** | 0.82 ± 0.16 |
| SCD | 0.93 ± 0.23 | 0.59 ± 0.13** | 0.93 ± 0.27 |
| MCAD | 1.04 ± 0.29 | 0.75 ± 0.12 | 1.36 ± 0.31* |
| CPT1 | 0.99 ± 0.24 | 0.94 ± 0.16 | 1.05 ± 0.19 |
| Triglyceride metabolism |  |  |  |
| GPAM | 1.09 ± 0.25 | 1.12 ± 0.27 | 1.16 ± 0.08 |
| MTTP | 1.18 ± 0.36 | 1.04 ± 0.14 | 1.31 ± 0.20 |
| PLTP | 1.01 ± 0.18 | 0.81 ± 0.36 | 0.97 ± 0.55 |
| Lipid uptake |  |  |  |
| SRB1 | 1.04 ± 0.12 | 1.52 ± 0.31** | 1.30 ± 0.22* |
| CD36 | 1.00 ± 0.27 | 0.71 ± 0.24* | 0.93 ± 0.36 |
| LDLR | 0.99 ± 0.06 | 1.38 ± 0.50* | 1.07 ± 0.09 |
| Cholesterol efflux |  |  |  |
| ABCA1 | 1.00 ± 0.18 | 1.08 ± 0.24 | 0.71 ± 0.12* |
| ABCG1 | 1.07 ± 0.50 | 1.38 ± 0.78 | 1.14 ± 0.76 |
| Bile acid metabolism |  |  |  |
| CYP7α | 1.08 ± 0.30 | 0.19 ± 0.18** | 0.60 ± 0.18** |
| CYP27α | 1.00 ± 0.12 | 1.00 ± 0.12 | 1.06 ± 0.23 |
| Glucose metabolism |  |  |  |
| G6Pase | 0.98 ± 0.34 | 0.25 ± 0.13** | 1.36 ± 0.77 |
| PCK1 | 0.98 ± 0.04 | 1.47 ± 0.37** | 1.02 ± 0.25 |
| GCK | 1.01 ± 0.01 | 0.57 ± 0.16** | 1.10 ± 0.68 |
| Pklr | 1.10 ± 0.17 | 0.77 ± 0.13** | 0.61 ± 0.18* |
| Others |  |  |  |
| SULT2B1b | 1.00 ± 0.35 | 3.33 ± 0.89** | 1.29 ± 0.34 |

Animals were treated as described in FIG. 1. All values are expressed as the means ± SD; n = 5-6;
*p < 0.05,
**p < 0.01 compared with HFD mice.

25HC3S Administration Decreases Nuclear SREBP-1 Protein Levels and Cytoplasimic FAS and ACC1 Expression in Liver.

SREBP-1c is responsible for up-regulation of fatty acids and triglyceride biosynthesis by binding to SREBP-1 response elements in response genes and increasing expression of the rate-limiting enzymes including FAS and ACC1. To determine if 25HC3S inactivated the SREBP-1c pathway, nuclear SREBP-1 protein level in liver was determined by Western blot analysis. Interestingly, HFD feeding markedly increased nuclear SREBP-1 mature form and induced its target gene ACC1 expression (FIG. 3A-D). 25HC3S significantly suppressed nuclear SREBP-1c, cytoplasmic ACC1 and FAS protein levels by 70%, 50% and 40%, respectively (FIG. 3A-D), which is consistent with mRNA levels as shown in (Table 2). In contrast, 25HC increased nuclear SREBP-1, cytoplasmic ACC1 and FAS protein levels (FIG. 3A-D), which could be induced by LXR activation. These results suggest that 25HC3S treatment suppresses lipogenesis by inhibition of SREBP-1c pathway.

Effects of Long-Term Treatment of 25HC3S on Lipid Homeostasis in HFD Fed Mice

Figure 4C:
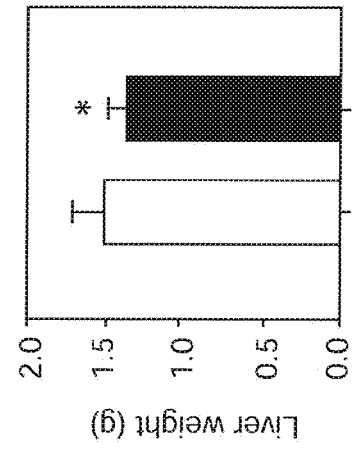
FIG. 4A-F. The effects of long term-treatment with 25HC3S on mouse body mass and food intake. C57BL/6J female mice were fed with HFD, separated to two groups, and treated with either 25HC3S or vehicle once every three days for 6 weeks. During these 6 weeks, the total food intake (A) and the body weight were monitored (B). After 5 hours fasting, the liver weight was determined (C), the plasma alkaline phosphatase (ALK) (D), alanine aminotransferase (ALT) (E) and aspartate aminotransferase (AST) (F) were determined. All the values are expressed as mean±SD. Statistical significant difference (p=0.017, n=16, by pair t-test). * $p<0.05$ and ** $p<0.01$ versus HFD-fed vehicle-treated mouse liver.
Figure 4B:
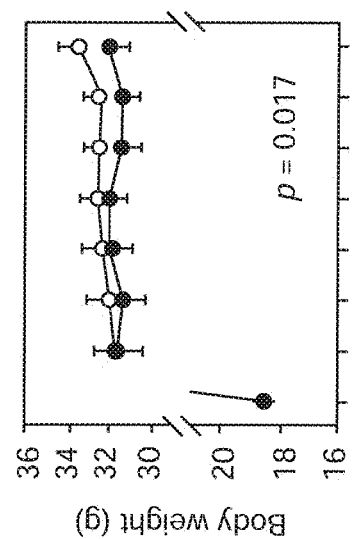
Figure 4A:
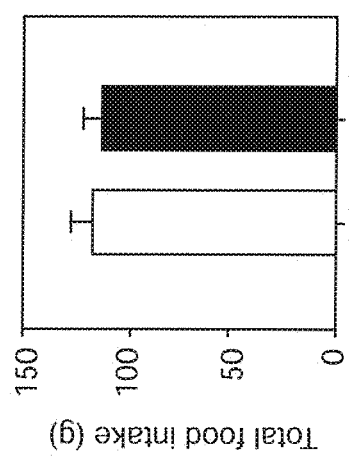
Figure 4F:
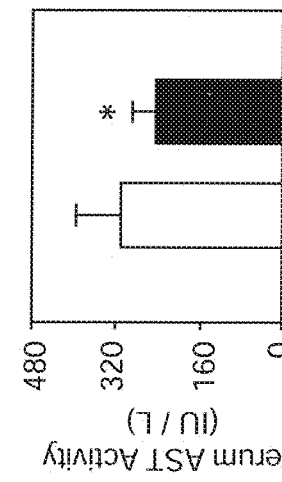

To study the effects of long-term treatment of 25HC3S on lipid homeostasis, 8-week-old C57BL/6J female mice were fed a HFD for 10 weeks, and then, divided into two groups: treated with 25HC3S or vehicle respectively by peritoneal injection once every three days. During the treatment, the HFD was continued, and we monitored body mass and caloric intake (FIG. 4A). 25HC3S treated mice stopped increasing body mass while the control group kept increasing as shown in FIG. 4B. After 6 weeks injection, the mice were fasted for 5 hrs, and sacrificed. The liver weight was significantly decreased in 25HC3S treatment group (FIG. 4C).

Figure 4E:
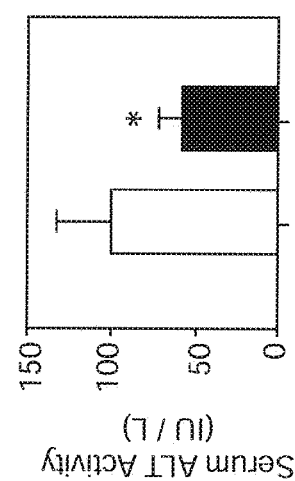
Figure 4D:
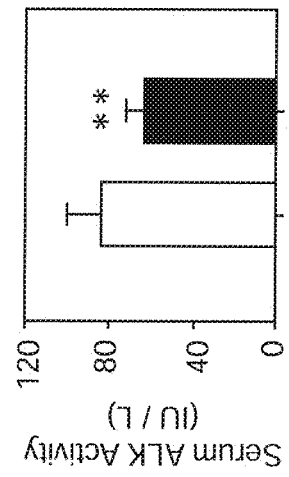

As expected, 25HC3S significantly decreased plasma cholesterol level as compared to vehicle-treated mice, but surprisingly, 25HC3S did not significantly decrease plasma triglyceride level (data not shown). Liver function analysis showed that 25HC3S treatment significantly reduced serum ALK, ALT and AST levels (FIGS. 4D,E,F). These results indicate that 25HC3S treatment suppresses hepatic inflammation and protects the liver from injury incurred by HFD.

To study the effect of 25HC3S on hepatic lipid metabolism, we measured hepatic lipid level and gene expression. HFD-fed increased triglyceride, total cholesterol, free cholesterol, and free fatty acid levels in liver by 3-, 3.5-3,2- and 2.5-fold compared to chow-fed mice (p<0.01). These increases were significantly reduced by 30%, 15%, 28% and 23%, respectively, by 25HC3S-treatment (FIG. 5A-D). It was noticed that cholesterol ester concentration was not affected by 25HC3S administration (FIG. 5E). The decrease in lipid level was further confirmed by a liver morphology analysis (FIG. 5F). The livers of HFD-fed mice were pale and were distended by large cytoplasmic lipid inclusions compared to that of chow-fed mice, suggesting successful NAFLD model following a HFD feeding. 25HC3S treatment significantly decreased lipid inclusions.

Gene expression study showed that 25HC3S significantly decreased mRNA levels of SREBP-1c, ACC1 and FAS by 23%, 41%, and 24%, respectively (Table 3), consistent with the acute treatment (Table 2), but the difference we found is that 25HC3S long-term treatment significantly decreased the key enzyme of triglyceride synthesis GPAM (19%), and lipid uptake CD36 (49%).

TABLE 3

Relative Hepatic mRNA Expresison in the Mice Fed a HFD with or without 25HC3S

|  | HFD | HFD + 25HC3S |
|---|---|---|
| Fatty acid biosynthesis |  |  |
| SREBP-1c | 0.98 ± 0.11 | 0.76 ± 0.08** |
| ACC1 | 1.05 ± 0.35 | 0.63 ± 0.08* |
| FAS | 0.96 ± 0.09 | 0.73 ± 0.16* |
| LXRα | 1.15 ± 0.17 | 0.95 ± 0.24 |

TABLE 3-continued

Relative Hepatic mRNA Expresison in the
Mice Fed a HFD with or without 25HC3S

|  | HFD | HFD + 25HC3S |
|---|---|---|
| Triglyceride metabolism | | |
| GPAM | 1.02 ± 0.16 | 0.81 ± 0.10* |
| MTTP | 1.02 ± 0.22 | 0.78 ± 0.09* |
| PLTP | 0.98 ± 0.32 | 0.60 ± 0.11* |
| Lipid uptake | | |
| SRB1 | 1.03 ± 0.18 | 0.87 ± 0.20 |
| CD36 | 0.92 ± 0.22 | 0.47 ± 0.08** |
| LDLR | 1.12 ± 0.23 | 0.79 ± 0.13 |
| Cholesterol efflux | | |
| ABCA1 | 1.01 ± 0.11 | 0.80 ± 0.12* |
| ABCG1 | 1.09 ± 0.26 | 0.72 ± 0.19* |
| Inflammatory cytokines | | |
| NFκB | 1.05 ± 0.34 | 0.86 ± 0.22 |
| IκBα | 1.05 ± 0.25 | 1.48 ± 0.38 |
| TNFα | 1.13 ± 0.23 | 0.60 ± 0.34* |
| IL1α | 1.16 ± 0.25 | 0.54 ± 0.14** |
| IL1β | 1.37 ± 0.46 | 0.58 ± 0.27* |

Animals were treated as described in FIG. 4. All values are expressed as the mean ± SD; n = 5-6
*p < 0.05,
**p < 0.01 compared with HFD mice.

Dysregulation of lipid metabolism is frequently associated with inflammatory conditions. 25HC3S treatment significantly suppressed the expression of TNFα, IL1α, and IL1β, by 47%, 53%, and 58%, respectively (Table 3) where 25HC increased the expression of IL1α and NFκB by 217% and 168%, respectively (data not shown). These results are consistent with liver function assays showing that 25HC3S suppresses liver inflammatory responses and improves liver damage (FIGS. 4E, F).

Discussion

The present study has shown that the acute treatment of mouse NAFLD models with 25HC3S decreases serum lipid levels; and the long term of treatment decreases both serum and hepatic lipid levels. 25HC3S suppresses key gene expressions involved in lipid biosyntheis at transcriptional levels via blocking activation of nuclear receptor LXRs and SREBPs, subsequently suppressing proinflammatory cytokines induced by HFD. Thus, 25HC3S serves as a potent regulator to reduce hepatic lipid levels effectively.

Example 2

Oxysterol Sulfation by SULT2B1b Suppresses LXR/SREBP-1c Signaling Pathway and Reduces Serum and Hepatic Lipids in Mouse Models of NAFLD In the present study, we further evaluated the effect of SULT2B1b on lipid metabolism in serum and liver tissues, and possible mechanism in vivo in mouse NAFLD models.

Materials and Methods

Animals and Treatment

Eight-week-old female C57BL/6 mice were purchased from Charles River Laboratories (Cambridge, Mass.) and LDLR$^{-/-}$ mice were from Jackson Laboratory (Sacramento, Calif.). Mice were hosted under a standard 12/1 2-hour light/dark cycle. Mice were fed with either standard rodent chow diet (Harlan Tekiad, Madison, Wis.), or a high-cholesterol diet (HCD, 3.1 Kcal/g, 2% cholesterol and 5.7% fat), or a high-fat diet (HFD, 4.5 Kcal/g, 0.2% cholesterol and 21.2% fat) for 10 weeks. Mice were then infected with recombinant adenovirus encoding CMV-driven SULT2B1b ($1 \times 10^8$ pfu/mouse) through tail vein injection. Ad-CMV-13-Gal adenovirus was used as control. In addition, some mice were given an intraperitoneal injection of 25HC 2 days after infection with virus as indicated. Mice were sacrificed following an overnight fast 6 days after adenovirus infection. All protocols were approved by the Institutional Animal Care and Use Committee (IACUC) of the McGuire VA medical center.

Immunohistochemistry

Formalin-fixed liver tissues were processed for histological analyses and stained with hematoxylin and eosin (H&E). Briefly, deparaffinized 4 μm sections were stained with rabbit anti-SULT2B1b antibody (AB38412, USA). Immobilized antibodies were detected by the avidin-biotin-peroxidase technique (Vectastain ABC Kits, Vector Laboratories, UK). DAB was used as the chromogen and methyl green or haematoxylin as the nuclear counterstain.

Lipid Levels in Liver Tissue and Sera

Liver cholesterol and triglycerides were extracted and analyzed as previously described in Example 1. Briefly, mouse liver tissue, 100 mg, was homogenized in 1 ml of PBS. The lipids in the homogenates were extracted with 9 ml of chloroform:methanol (2:1, v/v) overnight, sonicated for 1-2 hrs, and filtered. The extract, 100 was evaporated to dryness and dissolved in 100 μl of isopropanol containing 10% Triton X-100 for the cholesterol assay; dissolved in isopropanol for the triglyceride assay; or in NEFA solution (0.5 g of EDTA-Na$_2$, 2 g of Triton X-100, 0.76 ml of 1N NaOH, and 0.5 g of sodium azide/L of H$_2$O, pH 6.5) for the free fatty acids assay. Total and free cholesterol, triglycerides, and free fatty acids assays were performed according to the manufacturer's instructions.

For serum analysis, the lipid levels and the liver-specific cytosolic enzyme activities of alkaline phosphatase (ALP), alanine transaminase (ALT), and aspartate transaminase (AST) in serum of mice were determined by clinical biochemistry laboratory blood assays at the VA Medical Center. The lipoproteins of cholesterol and triglycerides (VLDL, LDL, and HDL) were measured by gel filtration using high pressure liquid chromatography (HPLC) as described in Example 1 with some modifications. Briefly, serum was centrifuged at 2000 rpm for 2 mm, and 100 μl of supernatant was subjected to HPLC with Pharmacia Superose 6HR 10/30 column using mobile phase, 154 mM NaCl, 0.1 mM EDTA pH 8.0 at flow rate of 0.2 ml/min. Each fraction was collected starting at 20 min, 1.2 min/each (240 μl) for up to 100 min. For cholesterol assay, 180 μl of each fraction was transferred to a 96 well plate, and 20 μl Wako total cholesterol kit 10× reagent buffer was added. After incubating at 37° C. for 3 hrs in the dark, the OD was read at 595 nm. For triglycerides assay, each 240 μl fraction was evaporated under N$_2$ gas. The residues were dissolved in 200 μl of Fisher Scientific Infinity triglyceride reagent, mixed, and transferred to a 96 well plate. The OD value was read at 500 nm. The protein profile was monitored at OD 280 nm as internal control.

Analysis of Composition of Oxysterols and Sulfated Oxysterols in Liver Tissue

Total lipids in liver tissue were extract by the well-known Folch method. Briefly, 200 mg of mouse liver tissue was homogenized in 1 ml of PBS. 20 ml of chloroform:methanol (2:1, v/v) was added in the homogenates, sonicated for 1-2 hrs, and filtered, 4 ml of water and 100 μl of 1 M K$_2$CO$_3$ were added, mixed, and allowed to stand for about 3 hrs for the phase separation.

The water/methanol (upper) phase, which contains sulfated oxysterols, and chloroform (lower) phase, which contains oxysterols, were evaporated under $N_2$ stream respectively. The residue from water/methanol phase was re-suspended in 0.5 ml of methanol, 3.5 ml of water and 0.5 ml of NaOH (1 N) by sonication, and the suspension was passed through a preconditioned Sep-Pak tC18 cartridge (Waters, Milford, Mass.) to remove non-sulfated oxysterols. After successively washing the cartridge with 8 ml of water, 3.5 ml of 15% acetone and 8 ml of water again, the sulfated oxysterol fraction was eluted in 5 ml of 75% methanol, which was taken to dryness under N2 stream below 40° C. The extracts were then hydrolyzed in 1 ml of sulfatase (2 mg/ml) at 37° C. for 4 hrs. De-conjugated oxysterols were extracted by Folch's partition ($CHCl_3:CH_3OH$, 2:1) and the chloroform phase was taken to dryness. The residue from chloroform phase was resuspended in 10 ml of hexane and passed through a pre-conditioned Pep-pak column. The oxysterols were eluted in 8 ml of 20% isopropanol/hexane after being washed by 3 ml of 1% isopropanol/hexane.

The oxysterol samples thus obtained from the methanol/water or chloroform phase were oxidized with cholesterol oxidase. To the oxysterol sample dissolved in 50 μl of 2-propanol were added 450 μl of water, 50 p μl of 1M potassium phosphate buffer (Kpi) and 1.5 μg of progesterone as an internal standard, and the resulting mixture was sonicated for 10 min. To the mixture 0.4 units of cholesterol oxidase in 50 μl of Kpi buffer was added and incubated at 37° C. for 1 h. 300 μl of methanol was added to stop the reaction and the products, enones, were extracted 3 times with 2 ml of hexane, and the extracts were evaporated under $N_2$ stream. The residue was re-dissolved in 150 μl of 5% isopropanol in hexane and 100 μl of the solution was subjected to the HPLC as described below.

HPLC analysis was conducted with an Alliance 2695 separation module fitted with 2487 Dual A absorbance detector (Waters, Milford, Mass.). The separation was carried out on an Ultraspere silica column (5 pm, 4.6 mm id×250 mm; Beckman, Urbana, Ill.) and hexane:isopropanol:acetic acid (965:25:10, v:v:v) as an eluent at a flow rate of 1.3 mL/min. The column temperature was kept constant at 30° C. The enones were monitored at 240 nm absorption.

Determination of Gene Expression Involved in Lipid Metabolism

Nuclear and cytosolic proteins from mouse liver tissue were extracted according to the manufacturer's instructions. 20 pg nuclear extracts or 50 pg cytosolic proteins were loaded on 10% SDS-PAGE for detection of the specific proteins, including LXRci, SREBP-1, SREBP-2, ACC-1, FAS, and SULT2BIb, using Lamin Bi and f3-actin as loading control for nuclear and cytosolic proteins respectively. Western blot analysis was performed using well-known methods, e.g. see Example 1.

Total RNA in liver tissue was isolated by SV total RNA isolation kit (Promega, Wisconsin, Wis.) following the manufacturer's instructions. Complementary DNA (cDNA) was synthesized retro-transcribing 2 pg of total RNA in a total volume of 20 μl using the M-MLV reverse transcriptase (Invitrogen, CA) according to manufacturer's instructions. The relative mRNA levels were measured by quantitative real-time polymerase chain reaction (qPCR). PCR assays were performed in 96-well optical reaction plates using the ABI 7500HT machine (Applied Biosystems, CA). PCR assays were conducted in triplicate wells for each sample. The following reaction mixture per well was used: 10 μl $RT^2$ Real-Time™ SYBR Green/Rox PCR master mix (SA Biosciences, MD), 1 μl of primer set at the final concentration of 500 nM, 4 μl RNase free water, 5 μl cDNA (10 ng). For all experiments the following PCR conditions were used: denaturation at 95° C. for 10 minutes, followed by 40 cycles at 95° C. for 15 seconds, then at 60° C. for 60 seconds. Quantitative normalization of cDNA in each sample was performed using GAPDH as an internal control. Suitable primers sequence-based were used.

Statistical analysis was carried out as described in Example 1.

Results

Effect of Adenovirus Infection on Liver Toxicity

To optimize the infection condition, the liver toxicity after infection with adenovirus was monitored with concentration- and time-dependence. The results showed that ALP, ALT, and AST activities in the serum were significantly increased 3, 6, 12, and 24 days after injection with adenovirus ($1 \times 10^9$ pfu), and the highest activities were noticed at day 6 as shown in FIG. 6A. Consistently, the ratios of liver weight to body weight were also significantly increased as shown in FIG. 6B. The serum activities of ALP, ALT, and AST and the ratios of liver to body weight following injection with different amount adenovirus for 6 days were shown in FIG. 6C and FIG. 6D. Only $1 \times 10^9$ pfu infection had the higher levels of ALP, ALT, and AST. Thus, $1 \times 10^8$ pfu for 6 days was selected to study the effect of SULT2B1b on lipid metabolism.

SULT2B1b Expression in Different Tissues after Infection with Ad-SULT2B1b

Figure 7A:
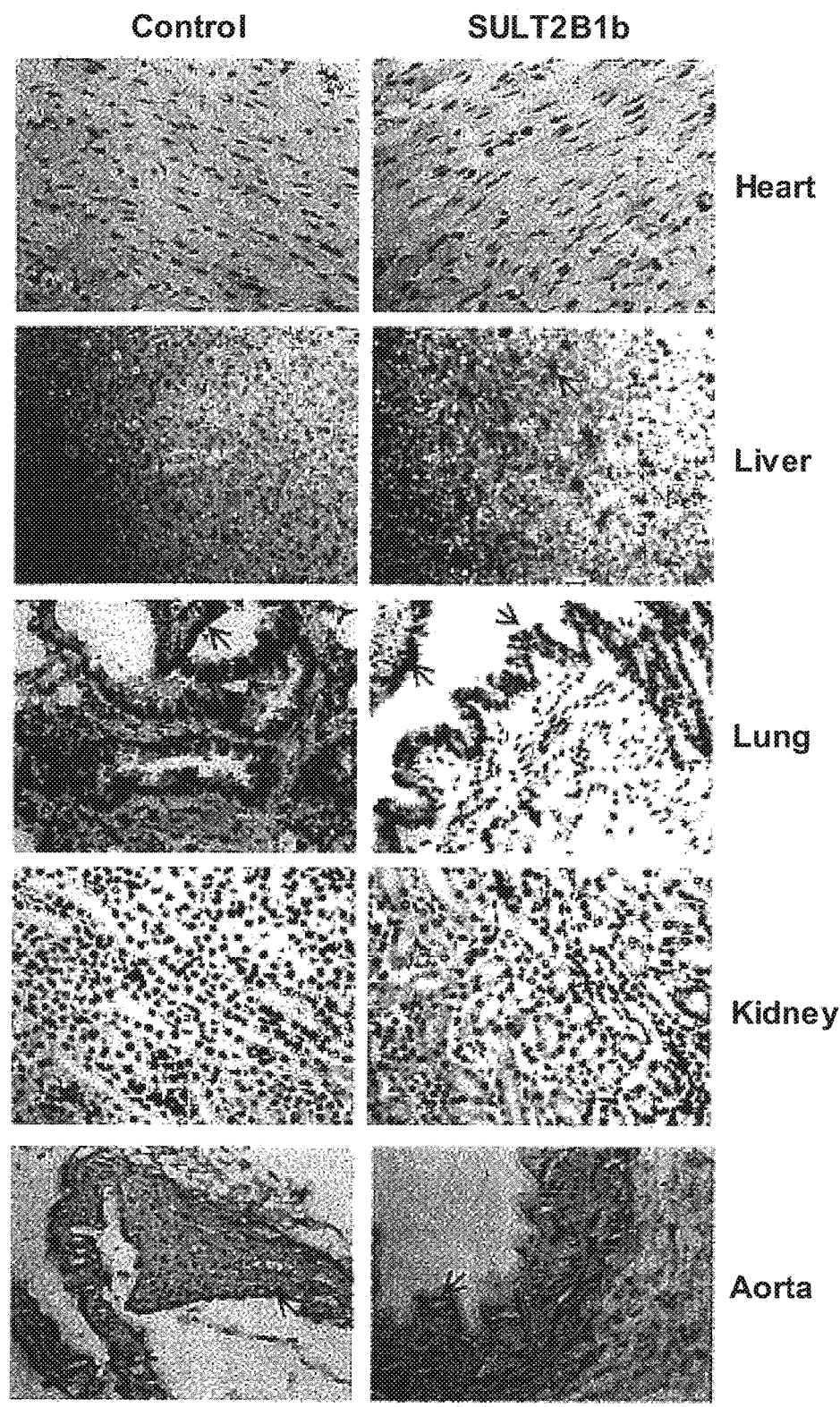
FIG. 7A-C. Determination of SULT2BI b expression in different tissues after infection with AdSULT2B1b. C57BL/6 mice, 12w, were infected with Ad-Control or Ad-SULT2B1b ($1\times10^8$ pfu) as indicated. (A) Immunohistochemistry analysis of SULT2BI b protein expression in different tissues 6 days after infection with Ad-Control or Ad-SULT2B1b. (B and C) SULT2B1b protein levels in different tissues were analyzed by Western blot. The data represent one of three separate experiments. * P<0.05, ** P<0.01 vs. Ad-Control.
Figure 7B:
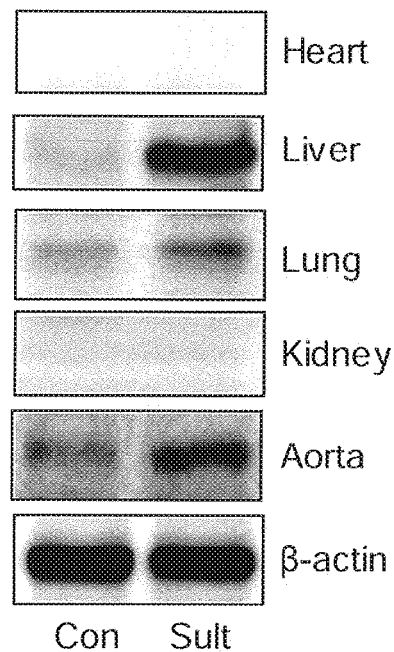
Figure 7C:
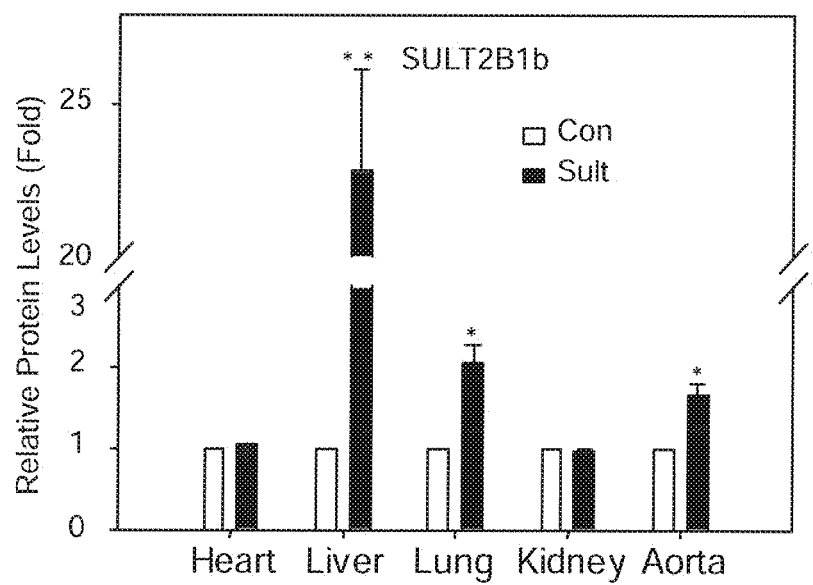

Mice were infected with Ad-SULT2B1b or Ad-control through tail vein injection in the condition as described above. Immunohistochemistry analysis showed that SULT2B1b gene expression was significantly increased in liver, aorta and lung tissues, but not in heart or kidney following infection (FIG. 7A). Consistently, western blot analysis showed that SULT2B1b gene expression increased by 20 fold in liver, 1.5 fold in aorta and 2 fold in lung following Ad-SULT2B1b infection, as compared to control, while no changes were detected in heart and kidney (FIGS. 7B and C).

Effect of SULT2B1b Overexpression on Lipid Levels in Sera and Liver Tissue.

Figure 8A:
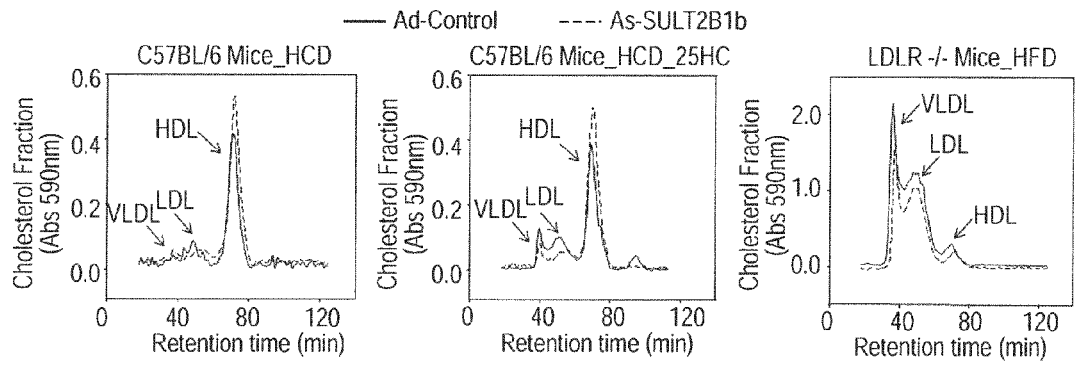
FIG. 8A-C. Effect of SULT2B1b overexpression on lipoprotein cholesterol and triglycerides in serum by HPLC. C57BL/6 mice and LDLR$^{-/-}$ mice, 8w, fed with high cholesterol diet (HCD) or high fat diet (HFD) for 10 weeks, then the mice were infected with Ad-control or Ad-SULT2B1b ($1\times10^8$ pfu) in the presence or absence of 25HC as indicated. Each group contains 5-6 mice. (A) HPLC analysis of the lipoprotein cholesterol (VLDL, LDL, and HDL) in serum both in C57BL/6 mice and LDL$^{-/-}$ mice. (B) HPLC analysis of the lipoprotein tryglycerides (VLDL, LDL, and HDL) in serum both in C57BL/6 mice and LDL$^{-/-}$ mice. (C) Protein assay in serum was used as internal control. The data represent one of three separate experiments.
Figure 8B:
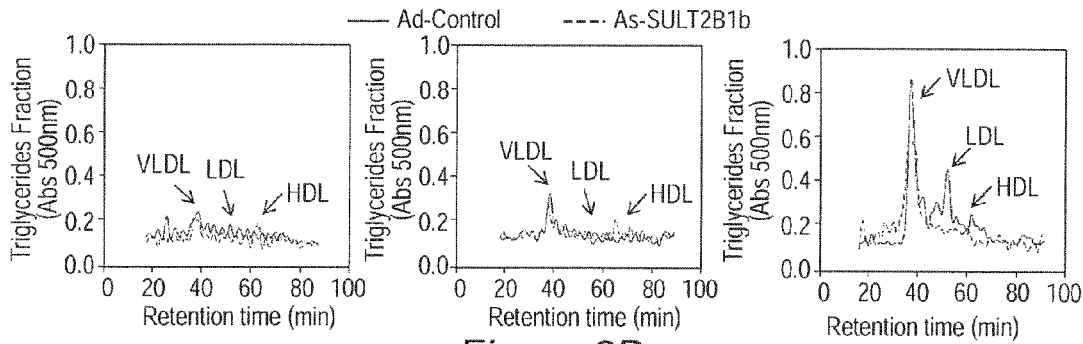
Figure 8C:
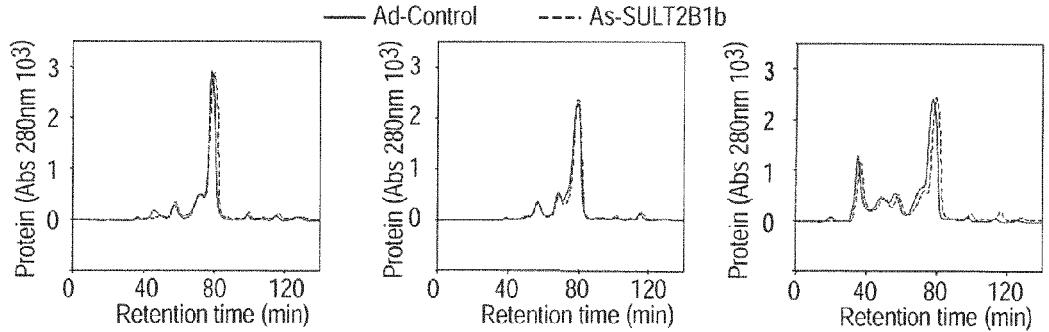
Figure 9A:
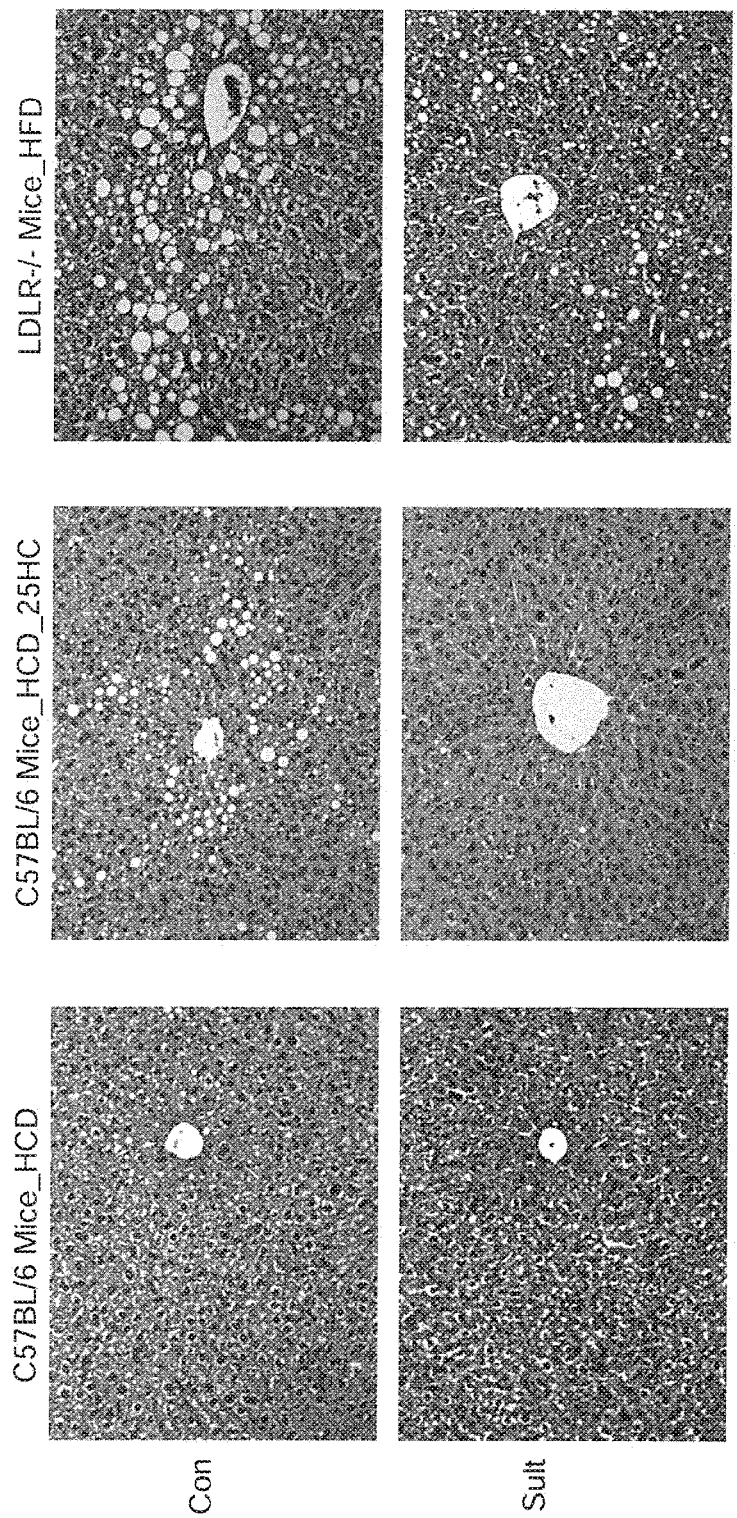
FIG. 9A-D. Effect of SULT2B1b overexpression on lipid levels in liver tissue. C57BL/6 mice and LDLR$^{-/-}$ mice, 8w, fed with high cholesterol diet (HCD) or high fat diet (HFD) for 10 weeks, then the mice were infected with Ad-control or Ad-SULT2B1b ($1\times10^8$ pfu) in the presence or absence of 25HC as indicated. Each group contains 5-6 mice. (A) H&E staining analysis of total lipids in liver tissue. (B-D) Triglycerides (TG), free fatty acids (FFA), total cholesterol (TC) and free cholesterol (FC) in liver both in C57BL/6 mice and LDLR$^{-/-}$ mice were analyzed as described in Methods. * P<0.05, ** P<0.01 vs. Ad-Control.
Figure 9B:
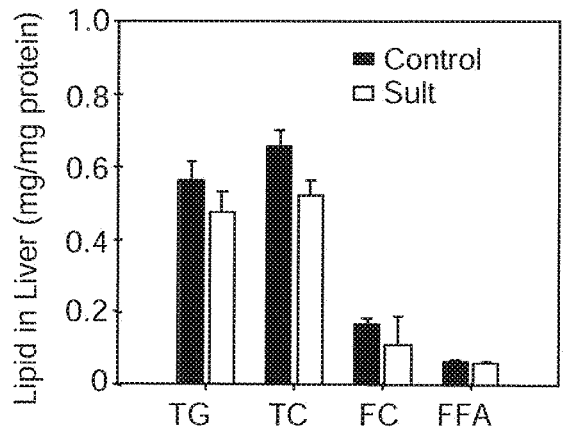
Figure 9C:
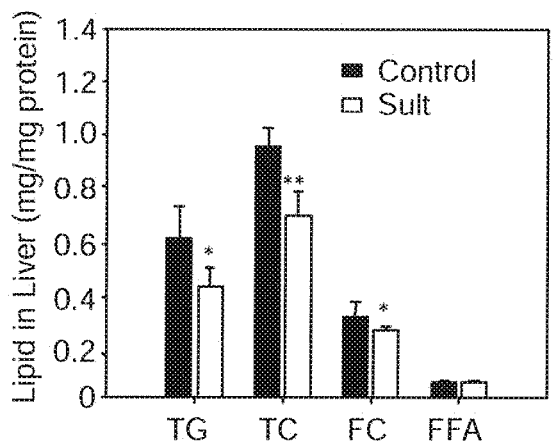
Figure 9D:
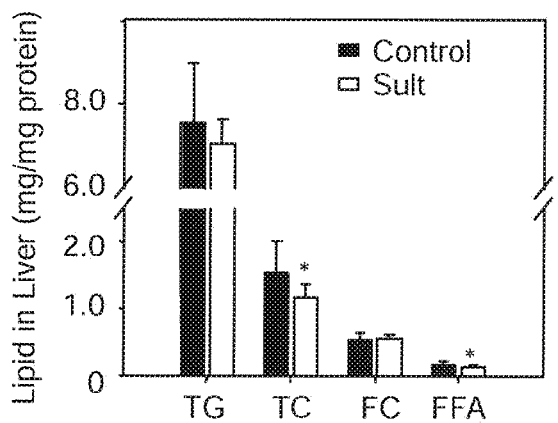
Figure 10A:
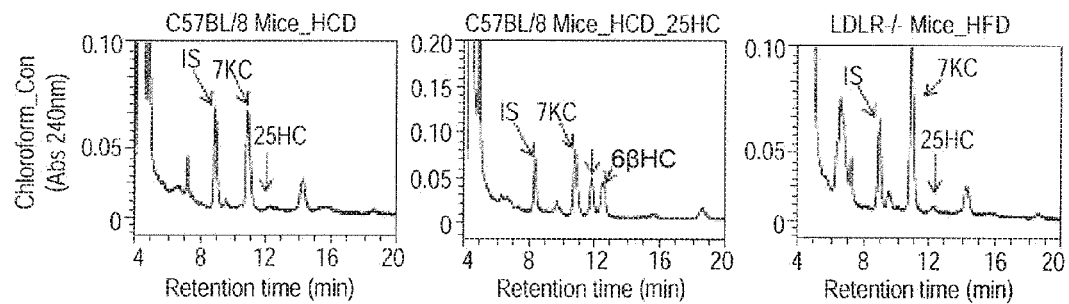
FIG. 10A-D. Effect of SULT2B1b overexpression on oxysterol and sulfated oxysterol levels in liver tissue. C57BL/6 mice and LDLR$^{-/-}$ mice, 8w, fed with high cholesterol diet (HCD) or high fat diet (HFD) for 10 weeks, then the mice were infected with Ad-control or AdSULT2B1b ($1\times10^8$ pfu) in the presence or absence of 25HC as indicated. Each group contains 5-6 mice. Total intracellular neutral lipids were extracted by adding 10 volumes of chloroform/methanol mixture (2:1, v/v). (A and B) Oxysterols in chloroform phase were analyzed by HPLC. (C and D) Sulfated oxysterols in methanol/water phase were analyzed by HPLC. 7KC, 6βHC, and 25HC were used as standard controls. The data represent one of three separate experiments.
Figure 10B:
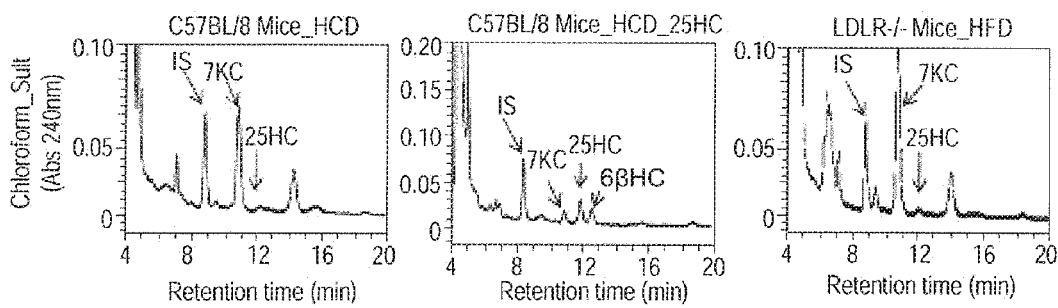
Figure 10C:
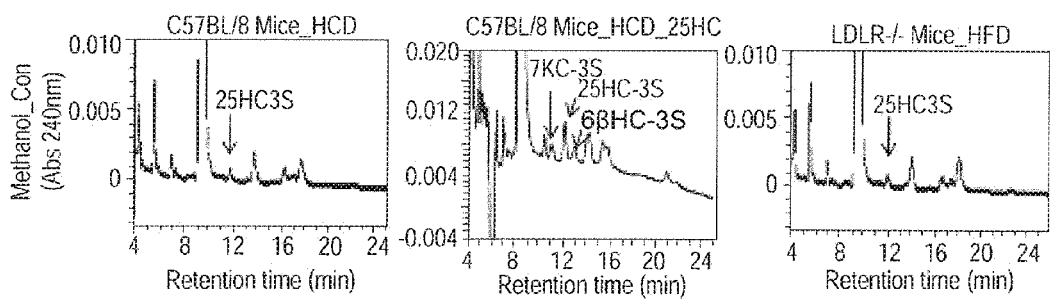
Figure 10D:
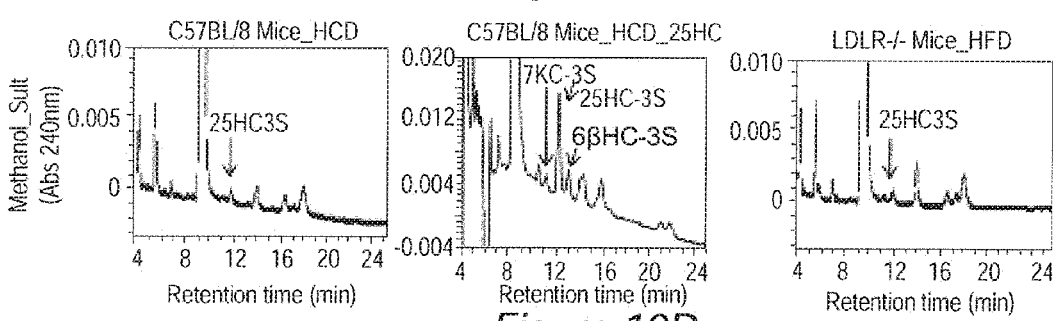

To study the effect of SULT2B1b on the lipid levels, the mice were infected by SULT2B1b adenovirus as described above. The serum lipid levels and specific enzyme activities were measured by clinical laboratory and are presented in Table 4. Following SULT2B1b overexpression triglyceride levels in serum in C57BL/6 mice fed with HCD were significantly decreased by 18%, in the presence of 25HC, but no change in the absence of 25HC as compared to control mice injected with 13-Gal virus. In $LDLR^{-/-}$ mice, both serum LDL and HDL were dramatically increased compared to those in C57BL/6 mice. The serum triglyceride levels were decreased by 32% following SULT2B1b overexpression as compared to the control in the knockout mice. However, total serum cholesterol levels both in C57BL/6 and $LDLR^{-/-}$ mice were unchanged with SULT2B1b overexpression. Interestingly, SULT2B1b overexpression decreased cholesterol and triglyceride levels in VLDL and LDL fraction in C57BL/6 and $LDLR^{-/-}$ mice while increased their levels in HDL fraction in C57BL/6 mice (FIG. 8A-C). These effects were much stronger in the presence of 25HC (FIG. 8A-C). There is no cytotoxicity following SULT2B1b overexpression as compared to no infection and 13-Gal virus infection (Table 4).

TABLE 4

Effect of SULT2B1b overexpression on serum lipids.

| | Wild Type HCD | | | |
|---|---|---|---|---|
| | Control | | SULT | |
| Lipids in serum | | | | |
| TG (mg/ml) | 53 | 7.3 | 49 | 12.4 |
| TC (mg/ml) | 117 | 12.7 | 120 | 8.4 |
| Glu (mg/ml) | 232 | 24.1 | 192 | 26.2* |
| LDL (mg/ml) | ND | ND | ND | ND |
| HDL (mg/ml) | 90 | 25.6 | 99 | 16.4 |
| Liver function | | | | |
| | 70 | 8.6 | 83 | 24.8 |
| ALT (IU/L) | 40 | 9.3 | 35 | 7.2 |
| | 201 | 34.1 | 228 | 49.2 |
| | Wild Type HCD + 25HC | | | |
| | Control | | SULT | |
| Lipids in serum | | | | |
| TG (mg/ml) | 39 | 3.4 | 32 | 4.3* |
| TC (mg/ml) | 102 | 8.2 | 107 | 9.3 |
| Glu (mg/ml) | 169 | 19.1 | 211 | 46.2 |
| LDL (mg/ml) | ND | ND | ND | ND |
| HDL (mg/ml) | 80 | 10.5 | 92 | 11.2 |
| Liver function | | | | |
| | 97 | 19.2 | 98 | 21.1 |
| ALT (IU/L) | 77 | 8.5 | 88 | 40.4 |
| | 229 | 4.1 | 264 | 61.9 |
| | LDLR$^{-/-}$ Mouse HFD | | | |
| | Control | | SULT | |
| Lipids in serum | | | | |
| TG (mg/ml) | 328 | 92.8 | 222 | 47.2* |
| TC (mg/ml) | 1338 | 203.8 | 1233 | 155.6 |
| Glu (mg/ml) | 222 | 42.7 | 266 | 32.3* |
| LDL (mg/ml) | 744 | 84.5 | 689 | 94.5 |
| HDL (mg/ml) | 529 | 190.3 | 497 | 120.5 |
| Liver function | | | | |
| | 92 | 23.4 | 77 | 19.1 |
| ALT (IU/L) | 151 | 74.7 | 79 | 37.4 |
| | 395 | 83.9 | 329 | 78.2 |

C57BL16 mice and LDLR mice, 8 w, fed with high cholesterol diet (HCD) or high fat diet (HFD) for 10 weeks, then the mice were infected with Ad-control or Ad-SULT2B1b ($1 \times 10^8$ pfu) in the presence or absence of 25HC as indicated. Total cholesterol (TC), triglycerides (TG), glucose (Glu), LDL, HDL and the enzyme activities of ALP, ALT, and AST in the serum were measured by clinical laboratory.
*$P < 0.05$,
**$P < 0.01$ vs. Con.
Values are mean SD. ND, not determined.

To determine the effects of SULT2B1b on hepatic lipid levels, total neutral lipids in liver tissue were extracted by chloroform-methanol (2:1, v/v) mixture. Quantitative analysis showed that overexpression of SULT2B1b significantly decreased hepatic triglyceride, total cholesterol, and free cholesterol levels in the presence of 25HC in C57BL/6 mice fed with HCD. No change was detected in the absence of 25HC as compared to control. In LDLR$^{-/-}$ mice, SULT2B1b overexpression significantly decreased total cholesterol and free fatty acids levels but did not change triglycerides and free cholesterol levels. Consistently, H&E staining also showed that SULT2B1b overexpression substantially decreased total neutral lipids in liver tissue both in C57BL/6 mice and LDLR mice (FIG. 9A-D).

Effect of SULT2B1b on Oxysterols and Sulfated Oxysterols in Liver Tissue.

To study whether generation of sulfated oxysterols is responsible for the effects of overexpression of SULT2B1b on the serum and hepatic lipid levels, oxysterols and sulfated oxysterols were exacted from liver tissue and analyzed by HPLC. The results showed that SULT2B1b overexpression in the presence of 25HC significantly increased sulfated oxysterols, especially 25HC3S, and decreased oxysterols, including 7-ketocholesterol (7KC), 6β-hydroxycholesterol (6βHC), and 25HC (FIG. 10A-D). However, in the absence of 25HC, SULT2BI b overexpression did not significantly change the levels of oxysterols and sulfated oxysterols (FIG. 10A-D).

Effect of SULT2BI b on Gene Expressions Involved in Lipid Metabolism

Figure 11A:
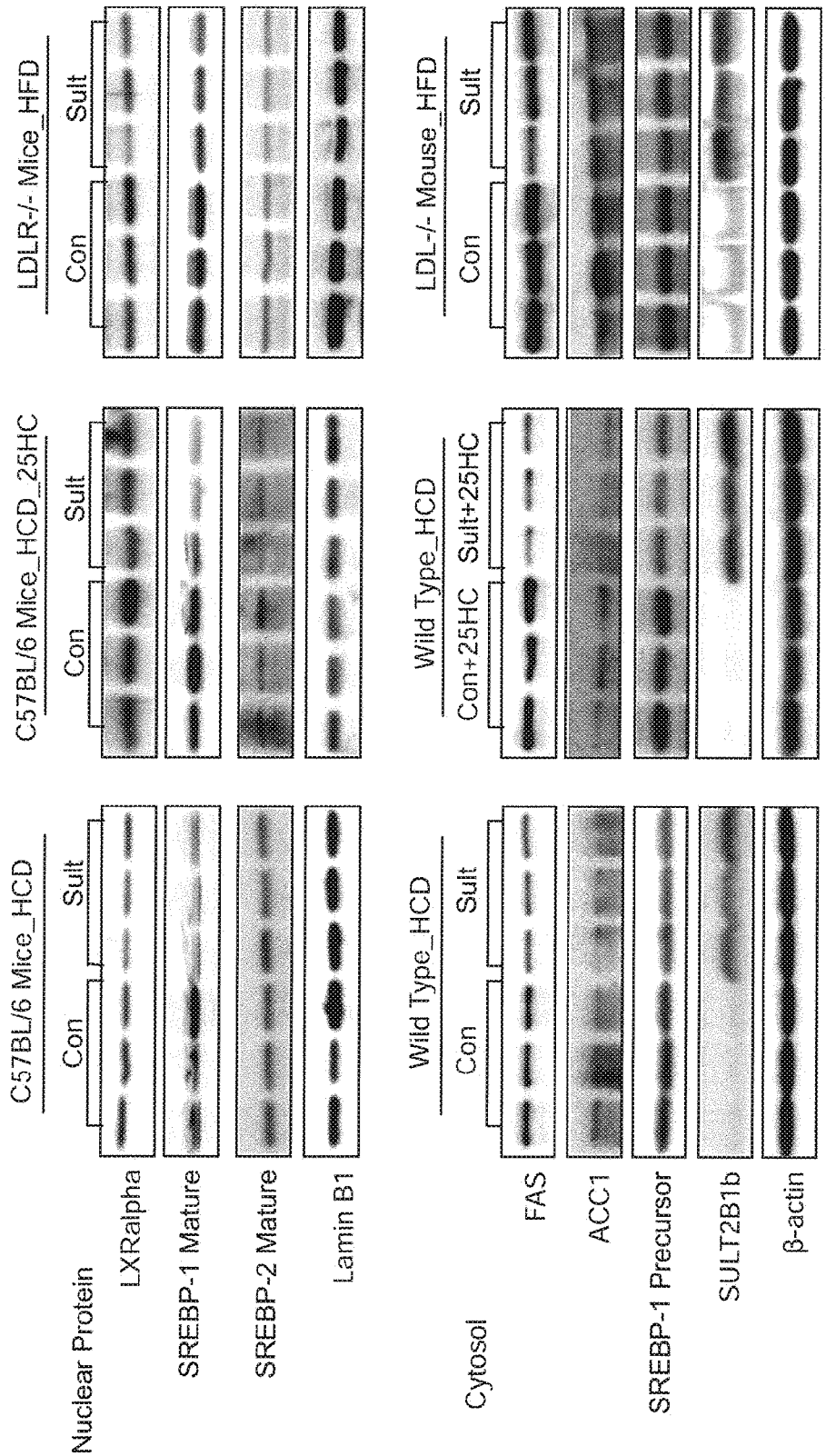
FIGS. 11A and B. Effect of SULT2B1b overexpressoin on gene expressions involved in lipid metabolism at protein level. C57BL16 mice and LDLR' mice, 8w, fed with high cholesterol diet (HCD) or high fat diet (HFD) for 10 weeks, then the mice were infected with Ad-control or Ad-SULT2B1b ($1\times10^8$ pfu) in the presence or absence of 25HC as indicated. (A) Western blot analysis of nuclear extracts and cytosolic proteins with specific antibodies against LXRa, ABCA1, SREBP-1, SREBP-2 and SULT2BIb. (B) Quantitative analysis for western blot data. * P<0.05, ** P<0.01 vs. Con.

To better understand the mechanism of SULT2B1b on lipid metabolism, gene expressions involved in lipid metabolism were determined. As expected, overexpression of SULT2B1b significantly decreased LXRα and SREBP-1 in nuclear protein levels but not SREBP-2 both in C57BL/6 mice and LDLR$^{-/-}$ mice fed with HCD or HFD. Consistently, SULT2B1b overexpression also significantly decreased the cytosolic protein levels of FAS and ACC1 as shown in FIGS. 11A and B.

Real-time RT-PCR analysis of the gene expressions at mRNA level involved in lipid metabolism was shown in Table 5. Consistent with protein levels, SULT2B1b overexpression significantly decreased mRNA levels of LXRα, SREBP-1, SREBP-2, GPAM, ACAT2, CYP27A, ABCAI, ABCGI and STS in the mice injected peritoneally with 25HC; in the absence of 25HC, SULT2B1b overexpression only decreased mRNA levels of LXRα, SREBP-1, and ABCA1.

TABLE 5

Effect of SULT2BI b overexpression on gene expressions involved in lipids metabolism at mRNA level.

| | Wild Type HCD | | | |
|---|---|---|---|---|
| | Control | | SULT | |
| Fatty acid metabolism | | | | |
| SREBP-1c | 1.0 | 0.29 | 0.57 | 0.19* |
| ACC1 | 1.0 | 0.37 | 0.93 | 0.15 |
| FAS | 1.0 | 0.41 | 0.76 | 0.21 |
| LXRα | 1.0 | 0.14 | 0.81 | 0.09* |
| PPARgamma | 1.0 | 0.26 | 0.59 | 0.17 |
| FABP4 | 1.0 | 0.51 | 0.68 | 0.19 |
| FATP | 1.0 | 0.39 | 0.59 | 0.15* |
| Triglyceride metabolism | | | | |
| GPAM | 1.0 | 0.62 | 0.94 | 0.36 |
| MTTP | 1.0 | 0.55 | 0.93 | 0.41 |
| PLTP | 1.0 | 0.69 | 0.94 | 0.51 |
| Cholesterol metabolism | | | | |
| SREBP-2 | 1.0 | 0.68 | 0.92 | 0.50 |
| HMGR | 1.0 | 0.19 | 0.90 | 0.08 |
| LDLR | 1.0 | 0.20 | 1.13 | 0.25 |
| ACAT1 | 1.0 | 0.12 | 1.02 | 0.35 |
| ACAT2 | 1.0 | 0.27 | 0.61 | 0.10* |
| Cholesterol efflux | | | | |
| ABCA1 | 1.0 | 0.22 | 0.65 | 0.09* |
| ASCG1 | 1.0 | 0.23 | 1.15 | 0.28 |
| Bile acid metabolism | | | | |
| CYP7a | 1.0 | 0.33 | 0.78 | 0.42 |
| CYP27a | 1.0 | 0.27 | 0.80 | 0.14 |

TABLE 5-continued

Effect of SULT2BI b overexpression on gene expressions involved in lipids metabolism at mRNA level.

Others

| | | | | |
|---|---|---|---|---|
| SILT2B1b | 1.0 | 0.24 | 193.5 | 46.1** |
| STS | 1.0 | 0.73 | 0.52 | 0.23 |

| | Wild Type HCD + 25HC | | | |
|---|---|---|---|---|
| | Control | | SULT | |

Fatty acid metabolism

| | | | | |
|---|---|---|---|---|
| SREBP-1c | 1.0 | 0.16 | 0.53 | 0.18* |
| ACC1 | 1.0 | 0.27 | 0.79 | 0.09 |
| FAS | 1.0 | 0.50 | 0.57 | 0.14 |
| LXRα | 1.0 | 0.30 | 0.63 | 0.08* |
| PPARgamma | 1.0 | 0.29 | 0.58 | 0.15* |
| FABP4 | 1.0 | 0.45 | 0.43 | 0.16* |
| FATP | 1.0 | 0.25 | 0.62 | 0.17* |

Triglyceride metabolism

| | | | | |
|---|---|---|---|---|
| GPAM | 1.0 | 0.33 | 0.69 | 0.11* |
| MTTP | 1.0 | 0.28 | 0.81 | 0.16 |
| PLTP | 1.0 | 0.13 | 0.85 | 0.20 |

Cholesterol metabolism

| | | | | |
|---|---|---|---|---|
| SREBP-2 | 1.0 | 0.08 | 0.71 | 0.07** |
| HMGR | 1.0 | 0.24 | 0.96 | 0.24 |
| LDLR | 1.0 | 0.39 | 0.53 | 0.11* |
| ACAT1 | 1.0 | 0.18 | 1.11 | 0.29 |
| ACAT2 | 1.0 | 0.21 | 0.73 | 0.06* |

Cholesterol efflux

| | | | | |
|---|---|---|---|---|
| ABCA1 | 1.0 | 0.22 | 0.65 | 0.16* |
| ASCG1 | 1.0 | 0.23 | 1.15 | 0.22* |

Bile acid metabolism

| | | | | |
|---|---|---|---|---|
| CYP7a | 1.0 | 0.33 | 0.78 | 0.31 |
| CYP27a | 1.0 | 0.27 | 0.80 | 0.07* |

Others

| | | | | |
|---|---|---|---|---|
| SILT2B1b | 1.0 | 0.24 | 193.5 | 114.8** |
| STS | 1.0 | 0.73 | 0.52 | 0.06* |

| | LDL$^{-/-}$ Mouse HFD | | | |
|---|---|---|---|---|
| | Control | | SULT | |

Fatty acid metabolism

| | | | | |
|---|---|---|---|---|
| SREBP-1c | 1.0 | 0.23 | 1.14 | 0.27 |
| ACC1 | 1.0 | 0.22 | 0.84 | 0.22 |
| FAS | 1.0 | 0.27 | 1.01 | 0.20 |
| LXRα | 1.0 | 0.19 | 0.82 | 0.11* |
| PPARgamma | 1.0 | 0.27 | 0.81 | 0.19* |
| FABP4 | 1.0 | 0.27 | 0.87 | 0.27 |
| FATP | 1.0 | 0.33 | 0.51 | 0.18** |

Triglyceride metabolism

| | | | | |
|---|---|---|---|---|
| GPAM | 1.0 | 0.19 | 0.90 | 0.17 |
| MTTP | 1.0 | 0.17 | 0.89 | 0.16 |
| PLTP | 1.0 | 0.15 | 0.69 | 0.11** |

Cholesterol metabolism

| | | | | |
|---|---|---|---|---|
| SREBP-2 | 1.0 | 0.14 | 0.94 | 0.16 |
| HMGR | 1.0 | 0.26 | 0.91 | 0.29 |
| LDLR | 1.0 | 0.34 | 0.80 | 0.22 |
| ACAT1 | 1.0 | 0.23 | 1.00 | 0.13 |
| ACAT2 | 1.0 | 0.19 | 0.89 | 0.10 |

Cholesterol efflux

| | | | | |
|---|---|---|---|---|
| ABCA1 | 1.0 | 0.26 | 0.89 | 0.17 |
| ASCG1 | 1.0 | 0.27 | 0.83 | 0.19 |

TABLE 5-continued

Effect of SULT2BI b overexpression on gene expressions involved in lipids metabolism at mRNA level.

Bile acid metabolism

| | | | | |
|---|---|---|---|---|
| CYP7a | 1.0 | 0.20 | 0.90 | 0.48 |
| CYP27a | 1.0 | 0.21 | 1.10 | 0.21 |

Others

| | | | | |
|---|---|---|---|---|
| SILT2B1b | 1.0 | 0.44 | 324.6 | 36.7** |
| STS | 1.0 | 0.57 | 1.28 | 0.37 |

C57BL16 mice and LDLR$^{-/-}$ mice, 8 w, fed with high cholesterol diet (HCD) or high fat diet (HFD) for 10 weeks, then the mice were infected with Adcontrol or Ad-SULT2B1b (1 × 10$^8$ pfu) in the presence or absence of 25HC as indicated. Gene expressions involved in lipid metabolism were analyzed by real-time PCR at mRNA level.
*P < 0.05,
**P < 0.01 vs. Con.

Discussion

The present study shows that SULT2B1b overexpression increases 25HC sulfation and its product 25HC3S mainly in liver tissue in vivo in mouse NAFLD animal models. Subsequently, SULT2B1b decreases serum and hepatic triglycerides, total cholesterol, free cholesterol, and free fatty acids, accompanied by reduction in key regulators and enzymes in lipid metabolism, including SREBP-1, SREBP-2, acetyl-CoA carboxylase-1, and fatty acid synthase. The results confirm that oxysterol sulfation by SULT2B1b plays an important role in lipid metabolism in vivo, indicating that oxysterol sulfation is another systematic signaling pathway involved in lipid metabolism. These findings also suggest that the sulfation product, 25HC3S, is an important endogenous regulator of lipid biosynthesis and has a potential to serve as a new medicine for therapy of NAFLD. These results indicate that the sulfated oxysterol may act as an LXR antagonist rather than only an inactive form of LXR ligand and that SULT2B1b plays an important role in lipid homeostasis, determining the balance between 25HC and 25HC3S, and represents a novel target for lipid metabolic disorder related diseases, including NAFLD and atherosclerosis.

In summary, the results indicate that 25HC sulfation by SULT2B1b substantially decreases serum and hepatic lipid levels via inhibiting the LXR-SREBP-1c signaling pathway. This finding supports the hypothesis that 25HC3S is an important endogenous regulator of lipid biosynthesis. This pathway represents a novel target for pharmacological intervention in NAFLD and other lipid-related disorders.

Example 3

Cholesterol Metabolite, 5-cholesten-3beta, 25diol 3-sulfate (25HC3S) Promotes Hepatic Proliferation in Mice 25HC3S is a sulfated oxysterol present in the nuclei of hepatocytes, where it plays an important role in regulating lipid metabolism In the present Example, we have shown for the first time that 25HC3S substantially up-regulates proliferative gene expression and induces DNA replication in liver. Conversely, treating mice with the liver-X-receptors (LXR) synthetic agonist, T0901317, leads to effective suppression of 25HC3S-induced proliferation, indicating the involvement of LXR signaling. These findings provide a previously undescribed function of 25HC3S in liver, and may shed light on our understanding of proliferative mechanisms regulated by the acidic pathway of bile acid biosynthesis in liver.

Experimental

Synthesis of 5-cholesten-3beta, 25-diol 3-sulfate (25HC3S)

25HC3S was synthesized as described in Example 1, with some modifications. Briefly, a mixture of 25-hydroxycholesterol (402 mg, 1 mmol) and triethylamine-sulfur trioxide pyridine complex (106 mg, 1 mmol) in 5 ml of dry pyridine was stirred at 25° C. for 2 h. After the solvents were evaporated at reduced pressure, products were purified by HPLC using a silica gel column, methylene chloride and methanol (5%) were used as the mobile phase. The product was further purified by reverse-phase HPLC using C18 column as obtained as a white powder. The structure of the product was characterized by mass spectrum and nuclear magnetic resonance spectroscopy analysis.

Synthesis of [$^3$H]-25HC3S

A mixture of [$^3$H]-25HC (10 μCi), cholesterol (4 mg) and triethylamine-sulfur trioxide complex (1 mg) in 500 ul of dry pyridine was stirred at 20° C. for 1 h. After the solvents were evaporated, 1 ml of alkaline methanol (pH 8) was added, mixed, filtered, and purified by HPLC (mobile phase A is 20% $CH_3CN$ in $H_2O$, B is 20% CHCN in $CH_3OH$, 0-20 min, A 50%-0%, B 50%-100%, 2 ml/min; 20-35 min, A 0%, B 100%, 2 ml/min; 35-40 min, A 0%-50%, B 100%-50%, 2 ml/min. A pure peak with the same retention time as standard 25HC3S and with high radioactivity was collected for further usage.

Animal Maintenance and Treatment.

Nine- to 12-week-old C57BL/6 mice were used and received humane care in accordance with the institutional guidelines and the National Institutes of Health Guide for the Care and Use of Laboratory Animals. Mice were randomly allocated into the following groups (n=3-5/group): (i) vehicle group-mice were administrated with 10% ethanol in phosphate buffer solution (PBS) intravenously (i.v.); (ii) 25HC3S group-same as vehicle group but in which 25HC3S (5 mg/kg, 10% ethanol) was administered i.v.; (iii) T0901317 group-identical to 25HC3S group except the administration of T0901317 (5 mg/kg, 10% ethanol administered i.v.; Cayman Chemical, Ann Arbor, Mich.); (iv) 25HC3S+T0901317 group-mice were administrated with 25HC3S and T0901317 (5 mg/kg, 10% ethanol administered i.v.). To get the mouse model with high endogenous 25HC3S, mice were received an i.v. injection of adenovirus encoding human SULT2B1b (Ad-SULT2B1b, 1×10$^8$ pfu/mouse), and further supplemented with 25HC (25 mg/kg, 10% ethanol; Research Plus, Inc. Bayonne, N.J.) intraperitoneally (i.p.), 2 days after the adenovirus infection and followed by once every two days [Bai Q, et al. Oxysterol sulfation by cytosolic sulfotranseferase suppresses liver X receptor/sterol regulatory element binding protein-1c signaling pathway and reduces serum and hepatic lipids in mouse models of nonalcohol fatty liver disease. Metabolism. (Accepted)]. Adenovirus encoding β-Gal (Ad-Control) or 10% ethanol (vehicle) in PBS was used as controls, respectively. Animals were sacrificed at 48 h after administration or day 5 following adenovirus injection. Blood samples were collected at sacrifice and serum was separated, stored at −80° C. until assayed. Alanine aminotransferase (ALT), aspartate aminotransferase (AST), and alkaline phosphatase (AP) concentrations were measured in the clinical lab at the McGuire VA Medical center. Liver tissues were harvested and divided into two portions, one for analysis of gene expression and the other for morphological studies.

Biodistribution and Pharmacokinetic Studies.

In a separate set of experiments, mice received an i.v. injection of [$^3$H]-25HC3S (1×10$^6$ cpm/mouse) and 25HC3S (5 mg/kg). At 4, 24, 48, and 96 h after the injection, mice were sacrificed, tissues (brain, heart, lung, liver, kidney, spleen, stomach, small intestine, skeletal muscle, and colon) were rapidly dissected and weighed, and the radioactivity was measured using a liquid scintillation counter with automatic decay correction (Beckman Counter, Atlanta, Ga.). Tissue values were calculated as a percentage of injected counts per gram of tissue (% IC/g). For pharmacokinetics, blood samples (30 μl) were collected at selected times after injection from 0 to 96 h via tail clip. Counts of radioactivity were expressed as IC/ml of blood.

RNA Extraction.

Total liver RNA was extracted using SV Total RNA Isolation Kit (Promega, Wisconsin, Wis.) according to the manufacture's instruction. RNA purity was checked by spectrophotometer. Complementary DNA (cDNA) was synthesized by retrotranscribing 2 ug of total RNA with Oligo dT primers and M-MLV Reverse Transcriptase (Invitrogen, Carlsbad, Calif.).

Quantitative Real-Time Polymerase Chain Reaction (RTqPCR) and Cell Cycle RT2 Profiler™ PCR Array.

PCR assays were performed in 96-well optical reaction plates using the ABI 7500 Fast Real-Time PCR System (Applied Biosystems, Foster City, Calif.). PCR assays were conducted in triplicate wells for each sample. Baseline values of amplification plots were set automatically and threshold values were kept constant to obtain normalized cycle times and linear regression data. The following reaction mixture per well was used: 2×SYBR Green PCR Master Mix (10 ul), primer at the final concentration of 10 uM (1 ul), RNAse-free water (4 ul), cDNA (5 ul, 10 ng). For all experiments the following PCR conditions were used: denaturation at 95° C. for 10 minutes, followed by 40 cycles at 95° C. for 15 seconds, then at 60° C. for 60 seconds. Quantitative normalization of cDNA in each sample was performed using 18S gene as an internal control. Relative quantification was performed using the ΔΔCT method. Suitable primers were used for RtqPCR.

The real-time PCR array was performed using the Mouse Cell cycle RT2 Profiler™ PCR Array consisting of 84 key genes involved in apoptosis and proliferation as the manufacturer's instruction (SABiosciences, Frederick, Md.). Total mRNA was reverse-transcribed to cDNA as described above. Three of biologically-distinct specimens were pooled to reduce variance. The cDNA was then amplified precisely like real-time PCR in the primers-preloaded PCR plates on the ABI 7500 Fast Real-Time PCR System. ΔΔCT values between different stimulated samples were analyzed as the manufacturer's instruction, which output p-values for fold-regulation change. Only those genes whose expression levels showed a 1.5-fold or greater expression difference between groups were considered significant changes between groups.

Liver Histology.

Liver specimens collected at sacrifice were fixed in 10% neutral-buffered formalin, embedded in paraffin, sectioned at 4 um, deparaffinized, and rehydrated. Endogenous peroxidase was inactivated by incubation in 3% hydrogen peroxide in absolute methanol for 30 min. Antigen retrieval was performed by microwaving of the sections in citrate buffer (PH 6.0) for 10 min. Sections were incubated overnight at 40° C. with the primary monoclonal antibody against proliferating cell nuclear antigen (PCNA) (ab29, Abcam, Cambridge, Mass.). After washing with PBS, immobilized antibodies were detected by the avidin-biotin-peroxidase complex technique (Vectastain@ ABC Kit, Vector Laboratories, Burlingame, Calif.). DAB (Vector Laboratories, Burlingame, Calif.) and haematoxylin (Sigma-Aldrich, St. Louis, Mo.) was used as the chromogen and nuclear counterstain, respectively. PCNA-positive and PCNA-negative nuclei were counted in five randomly selected fields for each sample, and each group included sections from at least 3 mice. The quantitation of PCNA expression was expressed as the PCNA labeling index.

Western Blot Analysis.

Cell lysates were prepared from frozen mouse liver tissues. Total proteins, 100 µg, were separated by 10% SDS-PAGE, and transferred to PVDF membrane (Millipore, Eschbom, Germany). Specific protein was probed with specific antibodies against PCNA, human SULT2B1b (Santa Cruz Biotechnology, Santa Cruz, Calif.), LXRa (Abcam, Cambridge, Mass.), ATP-binding cassette transporters 1 (ABCA1) (Abcam, Cambridge, Mass.), and SREBP-1c (Santa Cruz Biotechnology, Santa Cruz, Calif.). β-Actin (Sigma-Aldrich, St. Louis, Mo.) was used as a loading control. The immunoreactive bands were detected by Fujifilm Medical System (Fujifilm, Stamford, Conn.) and quantified by Advanced Image Data Analyzer (Aida Inc., Straubenhardt, Germany).

Statistical Analysis.

Statistical analyses were carried out as described in Example 1.

Results

Pharmacokinetics and Tissue Biodistribution.

Figure 12A:
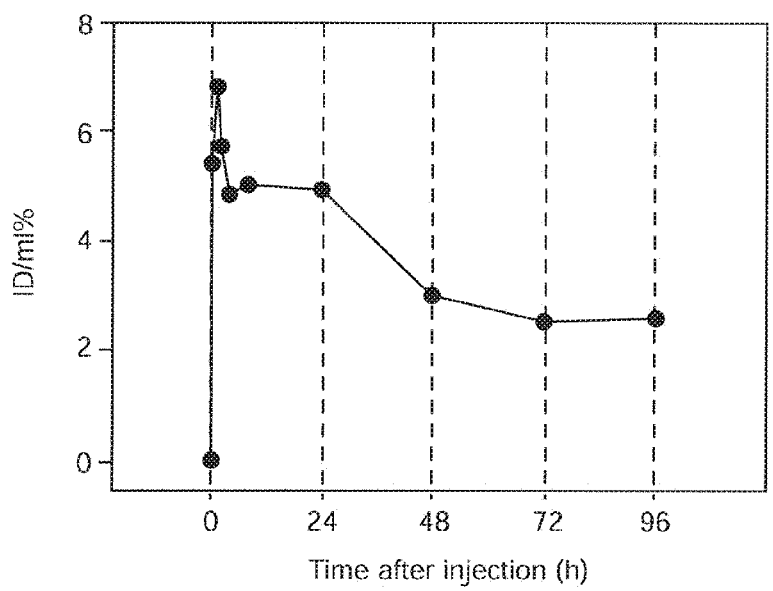
FIGS. 12 A and B. A, Pharmacokinetics and B, tissue biodistribution of radioactivity following intravenous injection of [$^3$H]-25HC3S and 25HC3S in mice. Each point represents one animal.

$^3$H-Radioactivity counts in the blood after i.v. injection of [$^3$H]-25HC3S and 25HC3S was shown in FIG. 12A. The compound showed slow clearance. $^3$H-Radioactivity in blood began to increase at 0.25 h, reached the maximum level of 7% IC/g at 1 h, and decreased to the half level at 48 h.

Figure 12B:
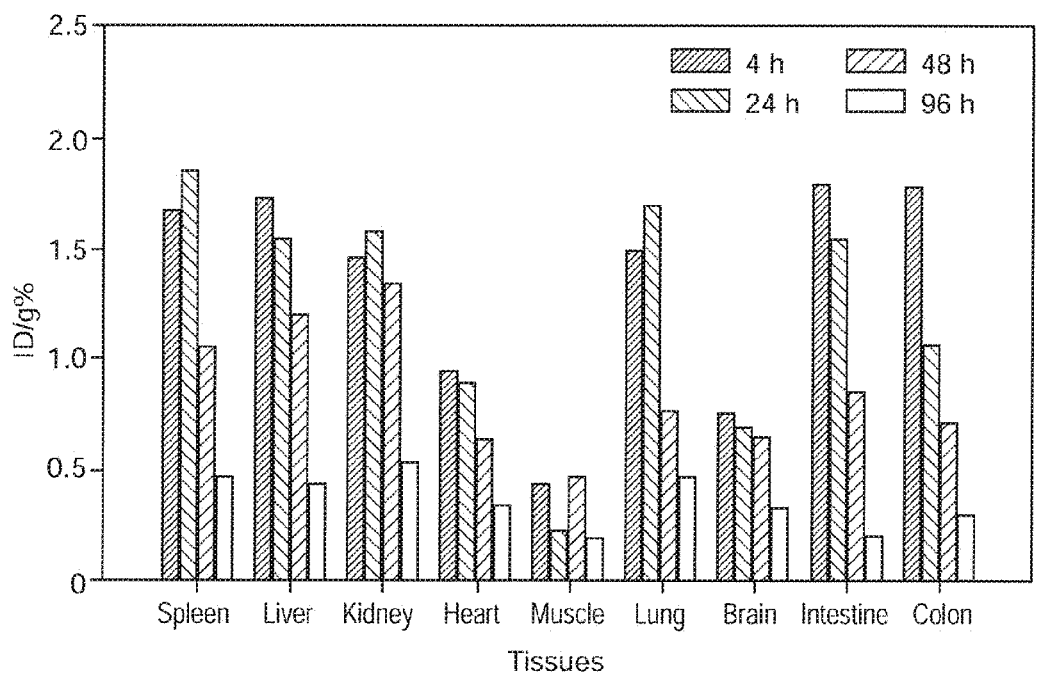
Figure 13A:
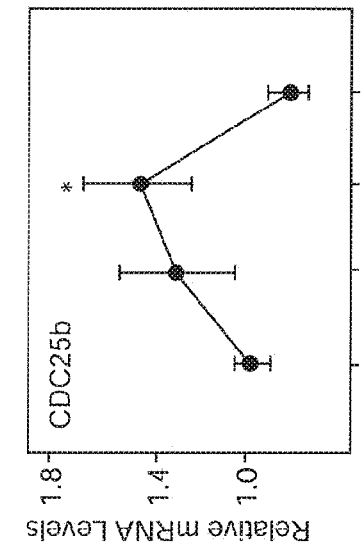
FIG. 13A-D. Expression levels of cell cycle-related genes in response to 25HC3S in mouse liver tissues. Mice have been treated for 48 h with 25HC3S at different concentrations as indicated. mRNA levels of FoxM1b (A), CDC25b (B), cyclin A (C), and c-myc (D) were analyzed by RTqPCR at the end of the treatment. The results are shown as mean±S.D. (n=3-5/group)* P<0.05 vs. mRNA expression at 0 mg/kg concentration.
Figure 13B:
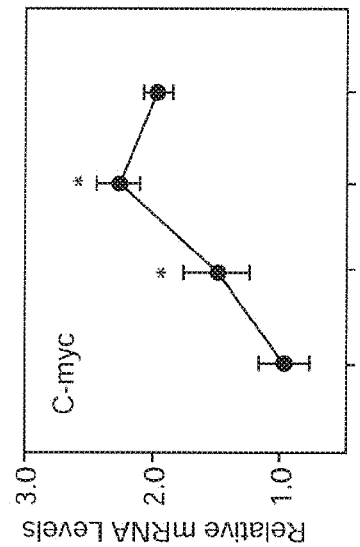
Figure 13C:
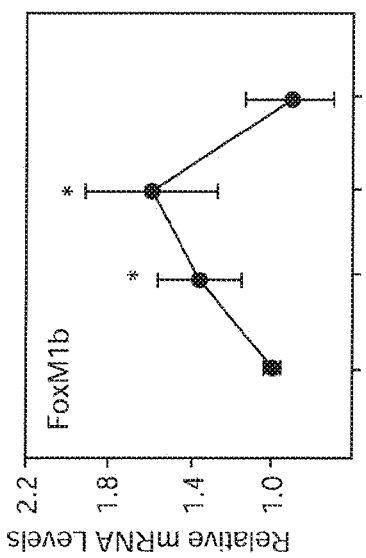
Figure 13D:
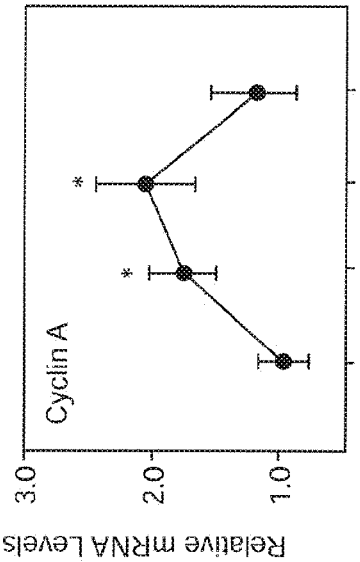

The tissue biodistribution of [$^3$H]-25HC3S were measured at 4, 24, 48 and 96 h after the i.v. administration. As shown in FIG. 12B, most of the organs exhibited the highest uptake of $^3$H-radioactivity at 4 h. Radioactivity remained at the level until 24 h, and gradually decreased with time. No obvious trend of radioactivity distribution was observed among spleen, liver, kidney, lung, small intestine, and colon. The radioactivity in these organs was relatively higher than those in heart, muscle, and brain at each time point after the injection. The results of long half life and wide distribution indicate that no specific receptor(s) of 25HC3S presents in vivo cells and tissues.

Effect of 25HC3S on Proliferative Gene Expression in Mouse Liver Tissues.

In order to investigate the effect of 25HC3 S on the hepatic proliferation, 48 h (half-decay period) was chosen in this study. Mice were treated for 48 h with different concentrations of 25HC3S (0-10 mg/kg). ALT, AST and AP activities were determined in mouse serum following the administration. ALT, AST and AP in serum of mice with 25HC3S administration were slightly higher than those without treatment. However, no significant differences were seen among the four groups (data not shown), indicating no toxicity where 25HC3S was administered. The hepatic mRNA levels of genes related to cell cycle progression, including cMyc, cyclin A, forkhead Box m1b (FoxM1b), and its target gene cell division cycle 25b (CDC25b), which control the cell cycle progression through G1/S and G2/M phases were investigated following the administration. RTqPCR analysis showed that at doses of 25HC3S lower than 5 mg/kg, mouse liver tissues displayed a significant up-regulation in the expression of these genes, and in a 25HC3S dose-dependent manner (FIG. 13A-D). However, when the concentration of 25HC3S reached to 10 mg/kg, most of these gene (except cMyc) expressions recovered to the normal level.

25HC3S Regulates the Expression of Apoptotic and Cell Cycle Related Genes.

To elicit the effects of 25HC3S on liver proliferation and to identify the genes regulated by 25HC3S in promoting proliferation, a real-time PCR array encompassing 84 genes associated with apoptosis and cell cycle progression was used. Mice were treated with vehicle or 25HC3S (5 mg/kg) for 48 h. Three of biologically-distinct mRNA samples were pooled to reduce variance, and the real-time array was run for each treatment. Table 6 lists the genes that were regulated by 1.5-fold difference or greater compared to vehicle group. Treatment with 25HC3S resulted in 18 genes up-regulated and 6 genes down-regulated. Interestingly, most of the up-regulated genes were positively related to the regulation of cell cycle progression, anti-apoptosis, and cell differentiation. 25HC3S substantially increased the expression of Wt1 (3.9-fold), an oncogene involved in the cell differentiation and viability, and PCNA (3.7-fold) encoding PCNA protein serves as a proliferative cell marker; and significantly increased the expression of Ccne2 encoding cyclin E2, an essential regulator for the cell cycle at the late G1 and early S phase, and Ccnb2 encoding cyclin B2, also serves as a proliferation marker and is crucial for the control of cell cycle at the G2/M transition. On the other hand, 25HC3S substantially decreased the expression of Chek2 by 4.5-fold encoding CHK2, an important protein kinase involved in cell cycle arrest in response to DNA damage and Apaf1 by 3-fold encoding apoptotic peptidase activating factor 1, a cytoplasmic protein that initiates apoptosis. Taken together, these data demonstrate that 25HC3S may enhance liver proliferation potential by up-regulating proliferative gene expression and down-regulating apoptosis gene expression.

TABLE 6

Mouse Profiler ™ Gene Expression Array analysis of mouse liver tissues induced by 25HC3S. Differential gene expression in response to 25HC3S treatment (5 mg/kg, 2 days) versus vehicle treatment was analyzed using the Mouse Cell cycle RT$^2$ Profiler ™ PCR Array. Three biologically-distinct mRNA samples were pooled to reduce variance. Genes equally down- or up-regulated by at least 1.5-fold in response to 25HC3S treatment were shown.

| Functional Gene Grouping | Gene Symbol | Fold change | Gene Name |
|---|---|---|---|
| Regulation of Cell cycle and Genes Related to the Cell Cycle | Ccnb2(NM_007630) | 1.90 | Cyclin B2 |
| | Ccne2(NM_009830) | 2.52 | Cyclin E2 |
| | Cdc25a(NM_007658) | 1.53 | Cell division cycle 25 homolog A (S. pombe) |
| | Cdc25c(NM_009860) | 1.56 | Cell division cycle 25 homolog C (S. pombe) |
| | Pcna(NM_011045) | 3.77 | Proliferating cell nuclear antigen |
| | E2f3(NM_010093) | 2.0193 | E2F transcription factor 3 |
| | Esr1(NM_007956) | 2.2535 | Estrogen receptor 1 (alpha) |
| | Mdm2(NM_010786) | 1.6222 | Transformed mouse 3T3 cell double minute 2 |
| | Wt1(NM_144783) | 3.90 | Wilms tumor 1 homolog |

TABLE 6-continued

Mouse Profiler ™ Gene Expression Array analysis of mouse liver tissues induced by 25HC3S. Differential gene expression in response to 25HC3S treatment (5 mg/kg, 2 days) versus vehicle treatment was analyzed using the Mouse Cell cycle RT² Profiler ™ PCR Array. Three biologically-distinct mRNA samples were pooled to reduce variance. Genes equally down- or up-regulated by at least 1.5-fold in response to 25HC3S treatment were shown.

| Functional Gene Grouping | Gene Symbol | Fold change | Gene Name |
|---|---|---|---|
| Cell Cycle Arrest and Negative Regulation of Cell Cycle | Cdkn1a(NM_007669) | 3.0411 | Cyclin-dependent kinase inhibitor 1A (P21) |
|  | Gadd45a(NM_007836) | −1.59 | Growth arrest and DNA-damage-inducible 45 alpha |
|  | Brca1(NM_009764) | −1.87 | Breast cancer 1 |
|  | Chek2(NM_016681) | −4.65 | CHK2 checkpoint homolog (*S. pombe*) |
|  | Trp73(NM_011642) | 2.5194 | Transformation related protein 73 |
| Cell Differentiation | Hif1a(NM_031168) | 1.7576 | Hypoxia inducible factor 1, alpha subunit |
|  | Myod1(NM_010866) | 1.56 | Myogenic differentiation 1 |
|  | Nf1(NM_010897) | 2.10 | Neurofibromatosis 1 |
| Induction of Apoptosis | Apaf1(NM_009684) | −3.21 | Apoptotic peptidase activating factor 1 |
|  | Tnf(NM_013693) | −2.76 | Tumor necrosis factor |
|  | Tnfrsf10b(NM_020275) | −2.28 | Tumor necrosis factor receptor superfamily, member 10b |
|  | Prkca(NM_011101) | 2.29 | Protein kinase C, alpha |
| Anti-apoptosis | Bag1(NM_009736) | 2.0488 | Bcl2-associated athanogene 1 |
|  | Bnip3(NM_009760) | 2.0112 | BCL2/adenovirus E1B interacting protein 3 |
| DNA Repair | Atr(NM_019864) | −2.15 | Ataxia telangiectasia and rad3 related |
|  | Xrcc5(NM_009533) | −1.90 | X-ray repair complementing defective repair in Chinese hamster cells 5 |
| Transcription Factors | Ep300(NM_177821) | 1.8114 | E1A binding protein p300 |

Induction of DNA Replication by Exogenous 25HC3S in Mouse Liver Tissues.

Proliferation in liver was examined with liver histology by counting PCNA labeling index. FIG. 14B shows PCNA staining in a liver specimen collected from 25HC3S treated mice, compared to vehicle control (FIG. 14A). Immunoreaction was observed as strong reaction (short arrow) or weak reaction (long arrow). The labeling index of cells with nuclear reaction was 12% in this case. We used this standard to evaluate all sections. Immunohistochemical analysis showed that treatment of mice with 25HC3S (5 mg/kg) for 48 h significantly increased the PCNA labeling index in liver as compared to the vehicle group (FIG. 14C). While no significant differences were seen between the vehicle group and no-treatment group (data not shown). The results indicate that 25HC3S promotes mouse liver proliferation.

Induction of DNA Replication by Endogenous 25HC3S in Mouse Livers.

Figure 15A:
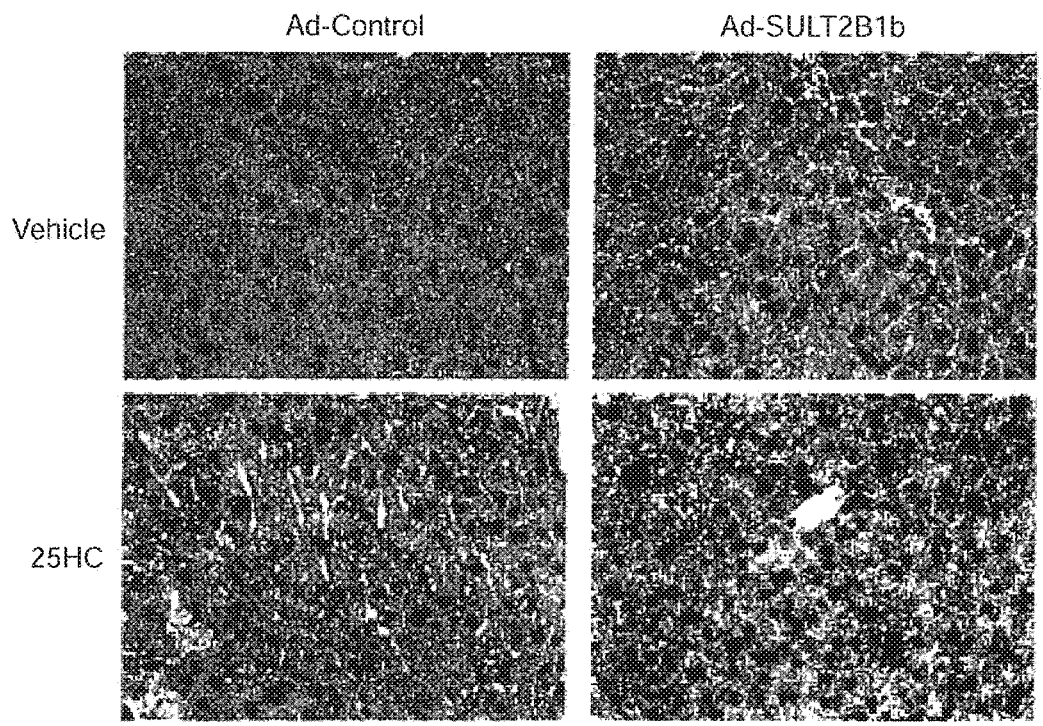
FIGS. 15 A and B. Effect of endogenous 25HC3S on PCNA labeling index in mouse liver tissues. A, Mice have been infected for 5 d with either Ad-Control or Ad-SULT2B1b ($1\times10^8$ pfu) in the presence or absence of 25HC (25 mg/kg) as indicated. B, PCNA labeling index obtained from liver sections of each group were analyzed at the end of the treatment. The results are shown as mean±S.D. (n=3-5/group) * P<0.05 vs. corresponding Ad-Control group.
Figure 15B:
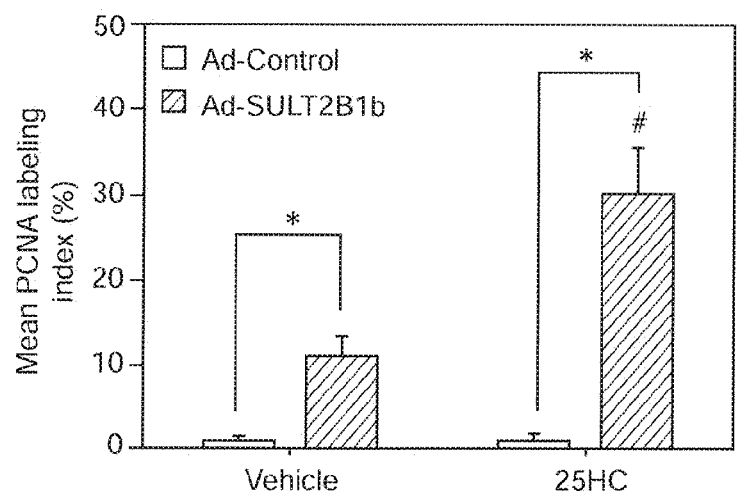

SULT2B1b is responsible for the synthesis of 25HC3S from 25HC. SULT2B1b overexpression in the presence of 25HC can effectively elevate 25HC3S levels in both primary hepatocytes and mouse liver. To further confirm the proliferation induction by endogenous 25HC3S in liver, PCNA positive cells were compared following overexpression of SULT2B1b. As the immunohistochemical analysis shown in FIGS. 15A and B, SULT2B1b resulted in a significant increase in the liver PCNA labeling index at day 5 following Ad-SULT2B1b infection with no evidence of toxicity (data not shown). The PCNA labeling index induced by SULT2B1b was further increased (up to 30%) in the livers of mice supplemented with 25HC. These results confirm that 25HC3S promotes liver proliferation.

Effect of 25HC3S on LXR Activity and its Target Gene Expression in the Mouse Liver Tissues.

Figure 16A:
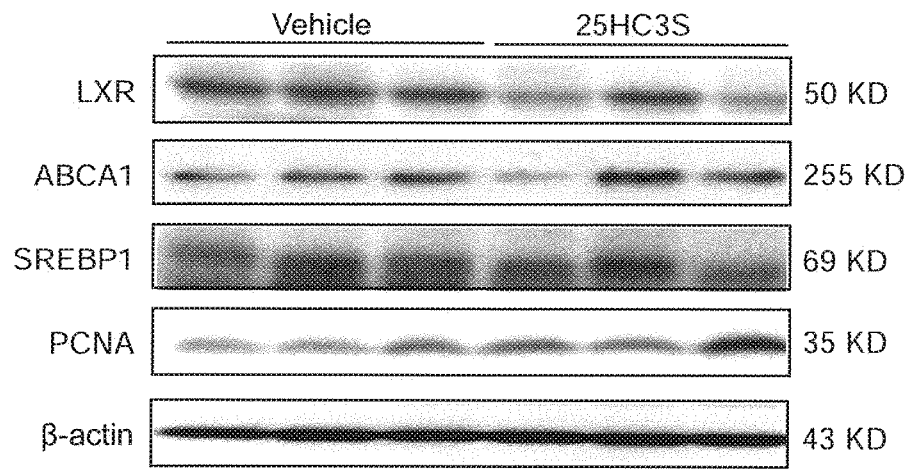
FIGS. 16 A and B. Effect of exogenous 25HC3S on LXR activity and its target gene expressions in mouse liver tissues. Mice have been treated for 48 h with vehicle or 25HC3S (5 mg/kg) as indicated. (A) LXRa, SREBP-1c, ABCA1, and PCNA proteins were detected by western blot at the end of the treatment. (B) Western blot data were quantitatively normalized to β-actin. The results are shown as mean±S.D. (n=3-5/group) * P<0.05 vs. Vehicle.
Figure 16B:
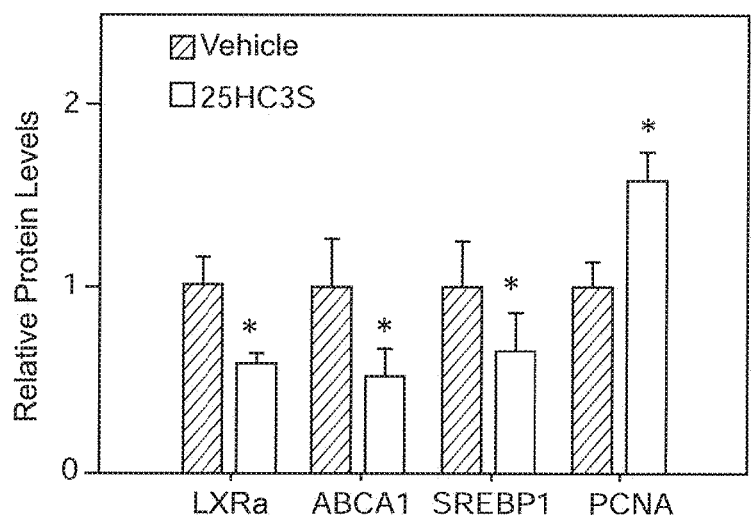
Figure 17A:
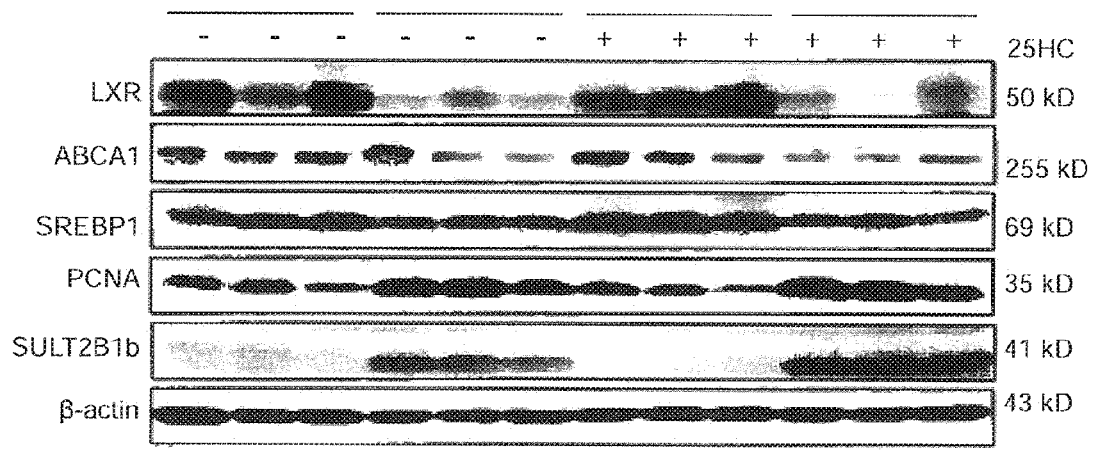
FIGS. 17A and B. Effect of endogenous 25HC3S on LXR activity and its target gene expressions in mouse liver tissues. Mice have been infected for 5 d with either Ad-Control or Ad-SULT2B1b ($1\times10^8$ pfu) in the presence or absence of 25HC (25 mg/kg) as indicated. (A) LXRa, SREBP-1c, ABCA1, and PCNA proteins were detected by western blot at the end of the treatment. (B) Western blot data were quantitatively normalized to β-actin. The results are shown as mean±S.D. (n=3-5/group) * P<0.05 vs. Ad-Control.
Figure 17B:
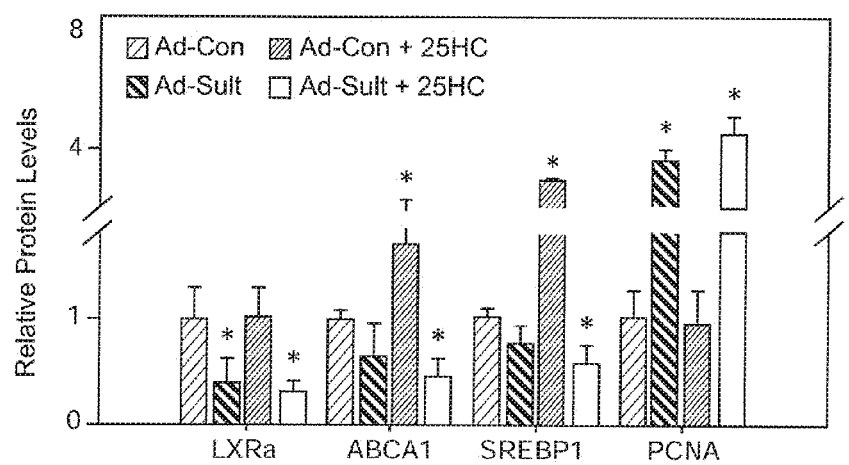

To understand the possible mechanisms by which 25HC3S promotes hepatic proliferation, the expression of genes regulated by LXR signaling pathway was analyzed in mouse liver tissues. As shown in FIGS. 16A and B, injection of mice with exogenous 25HC3S (5 mg/kg, 48 h) inhibited the activity of LXR response in liver, the protein levels of LXRα and its target genes ABCA1 and SREBP-1c in the 25HC3S group decreased by 40%, 50%, and 30%, respectively. For PCNA, the exogenous 25HC3S increased its protein level by 2-fold. Similar down-regulated liver LXR signaling and up-regulated PCNA expression were also observed in Ad-SULT2B1b infected mouse, where SULT2B1b overexpression in the presence (or absence) of 25HC decreased the protein levels of LXRa by 70% (60%), and SREBP-1c by 43% (25%); and increased the protein level of PCNA by 2-fold (2.5-fold), as compared to the Ad-control group (FIGS. 17A and B). In the Ad-Control and 25HC co-treatment group, 25HC effectively up-regualted the expression of ABCA1 and SREBP-1c, indicating the activation of LXRs signaling (FIGS. 17A and B). The data not only are consistent with previous studies showing the inactive effect of 25HC3S on LXR response in primary hepatocytes, but also support the idea that 25HC is a natural LXR ligand in vivo. Considering that LXR activation induces growth arrest and inhibits proliferation in many cells and animal models, the stimulation of proliferation by 25HC3S is related to the inactivation of LXR signaling.

Role of LXR Pathway on 25HC3S-Mediated Proliferation in Mouse Livers.

Figure 18A:
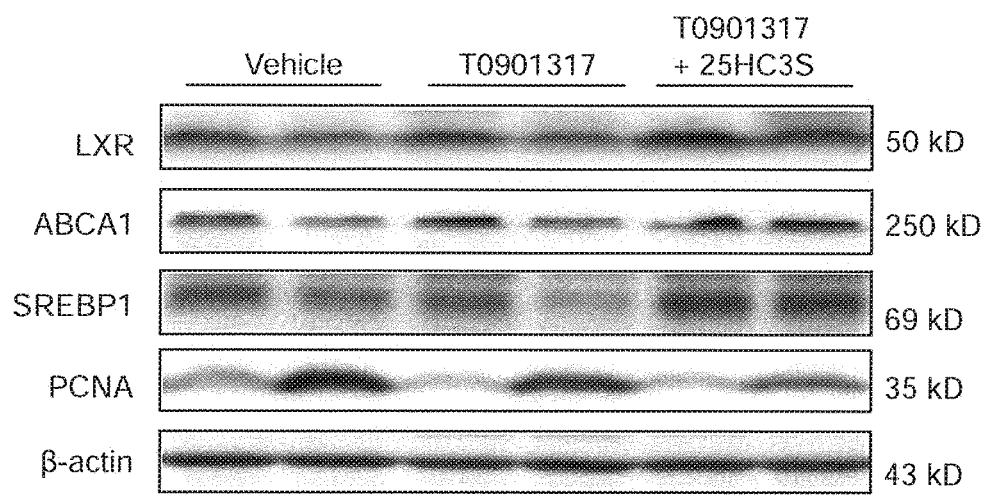
FIGS. 18A and B. Effect of LXR activation on 25HC3S-induced proliferation. Mice have been treated for 48 h with either vehicle or 25HC3S (5 mg/kg) in the presence or absence of T0901317 (5 mg/kg) as indicated. (A) LXRa, SREBP-1c, ABCA1, and PCNA proteins were detected by western blot at the end of the treatment. (B) Western blot data were quantitatively normalized to β-actin. The results are shown as mean±S.D. (n=3-5/group) * P<0.05 vs. Vehicle.
Figure 18B:
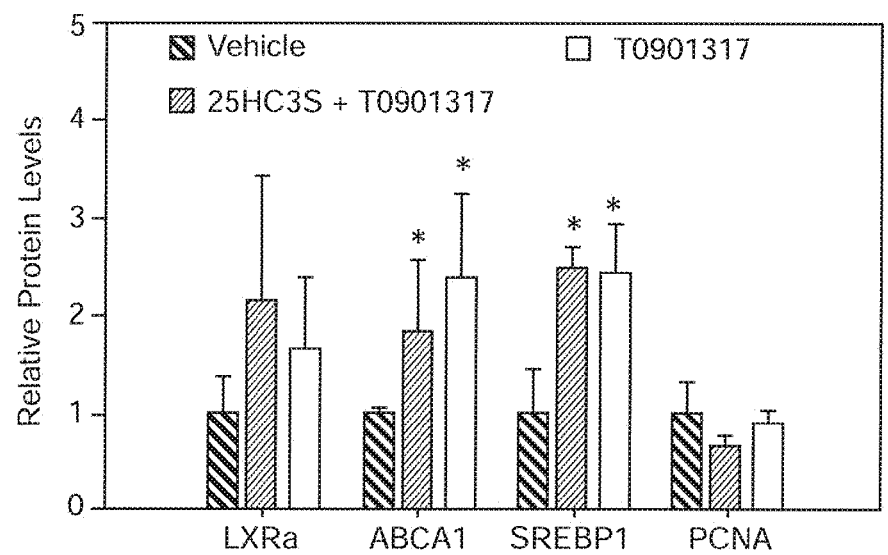

T0901317 is a potent synthetic LXR agonist. As an additional approach to investigate whether LXR signaling repression plays a role in 25HC3S-induced proliferation, we detected the effect of i.v. administration of T0901317 at 5 mg/kg to mice. As shown in western blot analysis in FIGS. 18A and B, T0901317 administration induced, at day 2 after the injection, the expressions of LXR target genes ABCA1 and SREBP-1c in both the presence and absence of 25HC3S as compared to the vehicle group. Furthermore, the T0901317 administration significantly repressed the 25HC3S-induced PCNA expression. The results further confirm that 25HC3S induces proliferation via inactivation of LXR signaling.

Discussion

The present study shows that LXR signaling pathway is down-regulated in livers of mice treated with 25HC3S). Our data showed that the presence of exogenous 25HC3S significantly increases the expression of proliferative genes at doses lower than 5 mg/kg. However, this effect is not observed when the concentration reaches to 10 mg/kg. In our high-performance liquid chromatography studies, we detected a small peak of 25HC in 25HC3S-treated mice liver. Thus, it is possible that the reduced effect of 25HC3S on proliferation is related to the accumulation of 25HC.

Example 4

Cytosolic Sulfotransferase 2B1b Promotes Hepatocyte Proliferation Gene Expression In Vitro And In Vivo In the present Example, we show for the first time that overexpression of SULT2B1b promotes hepatic proliferation. Decreases of SULT2B1b expression in primary rat hepatocytes (PRH) significantly repress the expression of cell cycle regulatory genes, including forkhead Box m1b (FoxM1b), cyclin-dependent kinase 2 (CDK2), and Cyclin A. Notably, LXR activation by T0901317 in cultured PRH and mouse liver effectively suppresses SULT2B1b-induced proliferation, indicating that the promotion of proliferation by SULT2B1b is via LXR signaling. These findings shed light on a previously undescribed role of SULT2B1b in enhancing liver proliferation.

Materials and Methods

Animals and Treatment.

Nine- to 10-week-old C57BL/6 mice were used and received humane care in accordance with the institutional guidelines and the National Institutes of Health Guide for the Care and Use of Laboratory Animals. For vector administration, the vector in 100 ul of sterile phosphate-buffered saline (PBS) was infused through tail vein. Two groups were used (n=3-5/group): the control group (Con) received $1\times10^8$ pfu/mouse of adenovirus encoding β-Gal (Ad-Control), while the SULT2B1b group (Sult) received a simultaneous injection of $1\times10^8$ pfu/mouse of adenovirus encoding human SULT2B1b (Ad-SULT2B1b). For study of LXR signaling pathway, mice were given intraperitoneal injections of T0901317 (25 mg/kg; New Cayman Chemical, Ann Arbor, Mich.) or 25HC (25 mg/kg; Research Plus, Inc. Bayonne, N.J.) 1 h after vector administration, and followed by once every two days. Animals were sacrificed at day 0, 2, 4, 5, and 12 after vector administration. Blood samples were collected at sacrifice and serum was separated, stored at −80° C. until assayed. Alanine aminotrasferase (ALT), aspartate aminotransferase (AST), and alkaline phosphatase (AP) concentrations were measured in the clinical lab of the McGuire VA Medical center. Liver tissues were harvested and divided into two portions, one for gene expression analyses and the other for morphological studies.

Immunohistochemistry.

Liver specimens collected at sacrifice were fixed in 10% neutral-buffered formalin, embedded in paraffin, sectioned at 4-μm, deparaffinized and rehydrated. Endogenous peroxidase was inactivated by incubation in 3% hydrogen peroxide in absolute methanol for 30 min. Antigen retrieval was performed by microwaving of the sections in citrate buffer (pH 6.0) for 10 min. Sections were incubated overnight at 4° C. with the primary monoclonal antibody against proliferating cell nuclear antigen (PCNA) (ab29, Abcam, Cambridge, Mass.). After washing with PBS, immobilized antibodies were detected by the avidin-biotin-peroxidase technique (Vectastain@ ABC Kit, Vector Laboratories, Burlingame, Calif.). DAB (Vector Laboratories, Burlingame, Calif.) and haematoxylin (Sigma-Aldrich, St. Louis, Mo.) was used as the chromogen and nuclear counterstain, respectively. The primary antibody was omitted as negative control. PCNA-positive and PCNA-negative nuclei were counted in five randomly selected fields for each sample, and each group included sections from at least 3 mice. The quantitation of PCNA expression was expressed as the percentage of PCNA-positive cells.

Double Immunofluorescent Staining.

Liver tissues from the mice at day 4 after Ad-SULT2B1b infection were used for double immunofluorescence to locate the expression of PCNA and human SULT2B1b. Deparaffinized 4-μm sections were cultured with a cocktail mix of two primary antibodies: mouse anti-PCNA antibody, 1:800 (ab29, Abcam, Cambridge, Mass.) and rabbit anti-SULT2B1b antibody, 1:30 (ab38412, Abcam, Cambridge, Mass.). Subsequent antibody detection was carried out with secondary antibodies: Alexa Fluor 488 goat anti-mouse IgG, 1:500 (Invitrogen, Carlsbad, Calif.) and Alexa Fluor 488 goat anti-rabbit IgG, 1:500 (Invitrogen, Carlsbad, Calif.). Negative control was performed by replacing the primary antibody with PBS. Sections were examined with a fluorescence microscope and merged images were formed using Adobe Photoshop CS2.

Culture of PRH.

PRH were prepared as previously described (24). Briefly, parenchymal cells ($3.5\times10^6$) were inoculated in 60-mm plastic Petri dishes coated with rat tail collagen. The plates contained 3 ml of Williams E culture media supplemented with thyroxine (1 μM), dexamethasone (0.1 μM), and penicillin (100 units/ml). Three hours after plating, culture medium was removed and fresh medium was added. Cells were then infected with Ad-SULT2B1b at a multiplicity (MOI) of 10 plaque forming units/cell (pfu/cell) or 100 nM of siRNA-SULT2B1b (ON-TARGET plus siRNA of rat SULT2B1b, Thermo Scientific Dharmacon, Lafayette, Colo.) as previously described (31). The Ad-Control and siRNA-Control (ON-TARGET plus negative control siRNA) were used as controls, respectively. Twenty four hours after infection, cells were treated with T0901317 (1.5 μM) or 25HC (3 μM) for another 24 hours. The cells were harvested at the timepoints as indicated in the text.

Cell Survival Assay.

Cultured hepatocyte-viability following treatments with Ad-SULT2B1b or siRNA-SULT2B1b for 24 h to 48 h, was evaluated using Cell Proliferation Kit I (Roche, Indianapolis, Ind.) according to the manufacturer's protocol. Briefly, cultured cells were treated with 3-(4,5-Dimethylthiazol-2-yl)-2, 5-diphenyltetrazolium bromide (MTT) for 4 h and then subcultured in solubilization solution. The absorbance of modified dye was measured at 570 nm. Assays were performed in triplicates. Ad-Control, siRNA-Control, and no treatment were used as controls.

Western Blot.

Cell lysates were prepared from frozen mouse liver tissues or PRH, and 50 μg of the total proteins were separated by 10% SDS-PAGE, transferred to polyvinylidene difluoride membrane (Millipore, Eschbom, Germany). Specific protein was probed with specific antibodies against PCNA, human SULT2B1b (Santa Cruz Biotechnology, Santa Cruz, Calif.), LXRα (Abcam, Cambridge, Mass.), ATP-binding cassette transporters 1 (ABCA1) (Abcam, Cambridge, Mass.), and SREBP1 (Santa Cruz Biotechnology, Santa Cruz, Calif.). β-Actin (Sigma-Aldrich, St. Louis, Mo.) was used as a loading control. Western analysis was performed by methods known in the art.

Reverse-Transcription Polymerase Chain Reaction (RT-PCR).

Total RNAs were isolated from mouse livers and PRH with SV Total RNA Isolation Kit (Promega, Wisconsin, Wis.). Two micrograms of total RNA was used for first-strand cDNA synthesis as recommended by the manufacturer (Invitrogen, Carlsbad, Calif.). Chosen genes were amplified by PCR. The PCR fragments were visualized on a 1.5% agarose gel containing 5 mg/ml ethidium bromide.

Quantitative Real-Time PCR (RTqPCR).

RTqPCR was performed using SYBR Green (Invitrogen, Carlsbad, Calif.) on the ABI-7500 Fast Real-Time PCR System (Applied Biosystems, Foster City, Calif.). The final reaction mixture contained 10 ng of cDNA, 100 nM of each primer, 10 μg of 2×SYBR Green PCR Master Mix, and RNase-free water to complete the reaction mixture volume to 20 μl. All reactions were performed in triplicate. The PCR was performed with a hot-start denaturation step at 95° C. for 10 min and then was carried out for 40 cycles at 95° C. for 15 s and 60° C. for 1 min. The intensity of fluorescence was read during the reaction, allowing a continuous monitoring of the amount of PCR product. The data were normalized to internal controls, 18S gene or GAPDH. Suitable primers were used for PCR and RTqPCR.

Statistical Analysis.

Data are expressed as mean±standard deviation (SD). Statistical comparison was made using Student's t test for unpaired samples. A value of P<0.05 was defined as statistical significant.

Results

Overexpression of SULT2B1b In Vivo by a Recombinant Adenovirus.

Figure 19A:
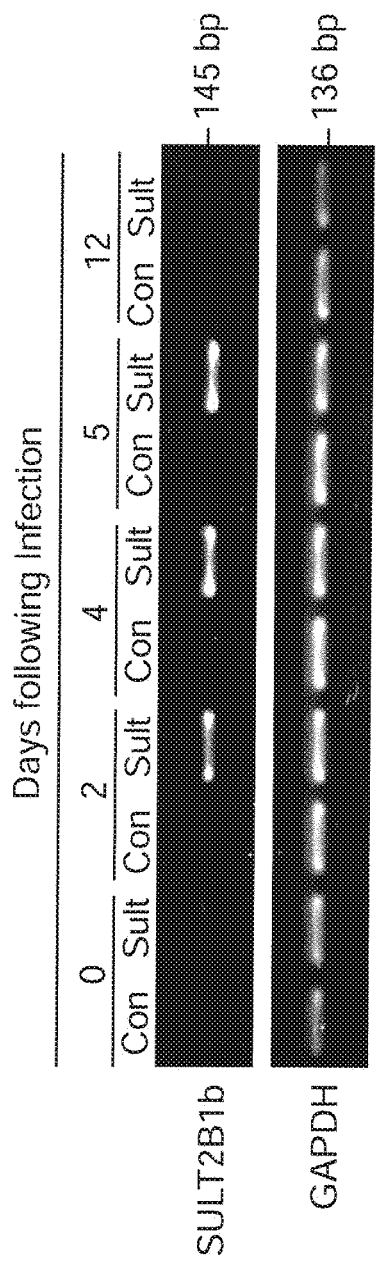
FIGS. 19A and B. SULT2B1b mRNA and protein levels in mouse liver tissues following infection. Mice were infected with Ad-Control or Ad-SULT2B1b. After the day as indicated, mice were sacrificed and liver tissues were collected. (A) Relative mRNA level of SULT2B1b expression was measured by RT-PCR. An equivalent of total RNA for each sample was loaded, and 25 cycles for each sample were used for PCR analysis. (B) SULT2B1b protein level was determined via western blot analysis. The results are shown as mean±S.D. (n=3-5/group) *P<0.05 vs. day 0.
Figure 19B:
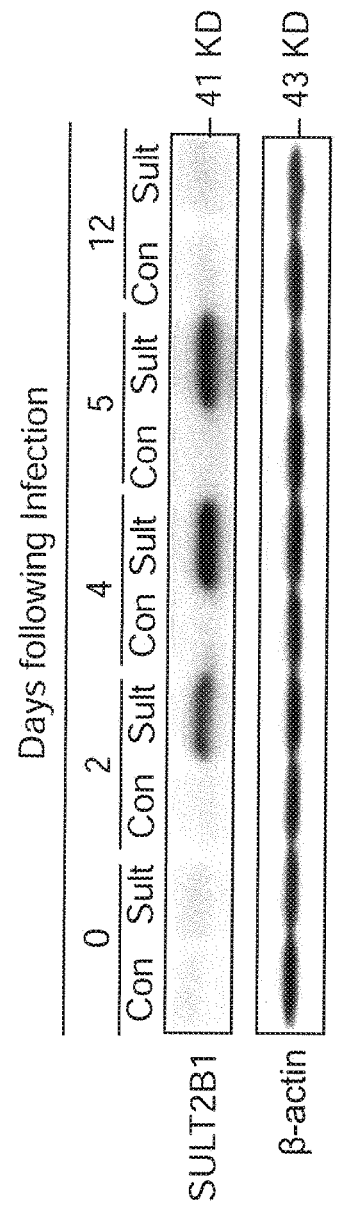
Figure 20A:
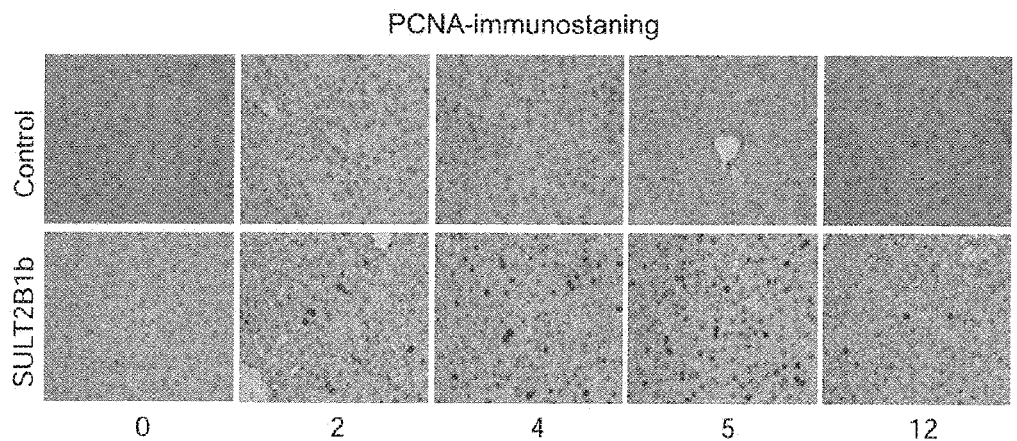
FIG. 20A-C. Effect of SULT2B1b on PCNA expression in mouse liver tissues. At the indicated day following infection with Ad-Control or Ad-SULT2B1b, mice were sacrificed and liver tissues were harvested. (A) Representative photomicrographs from PCNA-stained liver sections (20× optical field); (B) Percentage number of PCNA-positive cells obtained from liver sections; (C) SULT2B1b and PCNA protein levels were determined via western blot analysis. The results are shown as mean±S.D. (n=3-5/group) *P<0.05 vs. day 0.
Figure 20B:
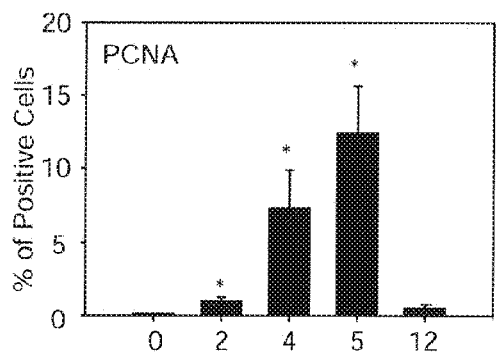
Figure 20C:
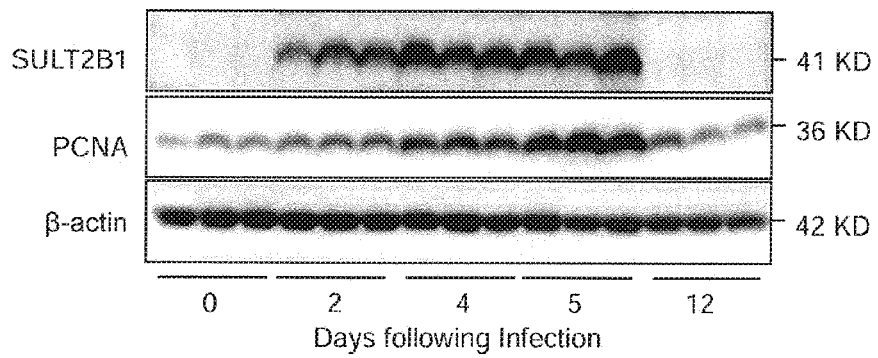

ALT, AST and AP activities were determined in mouse serum following adenovirus infection. ALT, AST and AP in serum of mice with Ad-Control or Ad-SULT2B1b injection were slightly higher than those without virus. However, no significant differences were seen among the three groups (data not shown), indicating no toxicity was observed where the adenovirus was infected. RT-PCR and western blot analysis of human SULT2B1b expression in the livers at day 0, 2, 4, 5 and 12 after injection were performed to verify the transgene expression. Human SULT2B1b mRNA and protein levels were substantially increased in the liver following infection of mice with Ad-SULT2B1b (FIGS. 19A and B): started the increase at day 2, increased to its highest level at day 4 and day 5 and returned to the normal level at day 12. However, no human SULT2B1b expression was detected in the liver of control group. Effect of SULT2B1b on PCNA expression in mouse liver tissues. PCNA is a protein for DNA replication in proliferating cells. To determine the effect of SULT2B1b on proliferation in liver, PCNA was used as a proliferation marker. Immunohistochemistry analysis showed that the number of PCNA-positive cells in mouse liver tissues was significantly increased with the enhanced SULT2B1b expression, as compared to day 0 (FIGS. 20A and B). However, in the control group, number of PCNA-positive cells following the infection did not change significantly (FIG. 20A). Western analysis in the FIG. 20C showed that the PCNA protein levels were coincidentally increased with SULT2B1b: started to increase at day 2, reached the maximum at day 5, and returned to the baseline at day 12. The results indicated that the increases in SULT2B1b expression induce PCNA expression, which further confirmed the immunohistochemistry study.

Locations of PCNA and SULT2B1b Expression in Mouse Liver Tissues.

To elucidate the relationship between SULT2B1b and PCNA, double immunofluorescence was performed in liver specimens collected from control and SULT2B1b group at day 4 after infection. The results (not shown) indicated that the hepatocytes with PCNA expression in the nuclei were accompanied by SULT2B1b overexpression in the cytosol. Interestingly, no PCNA expression was detected in the cells without SULT2B1b expression, indicating that SULT2B1b is directly associated with the expression of PCNA. The PCNA and human SULT2B1b positive cells were undetectable in the liver sections from control group (data not shown).

Effect of SULT2B1b on the mRNA Levels of Cell Cycle Regulatory Genes in Mouse Liver Tissues.

Figure 21A:
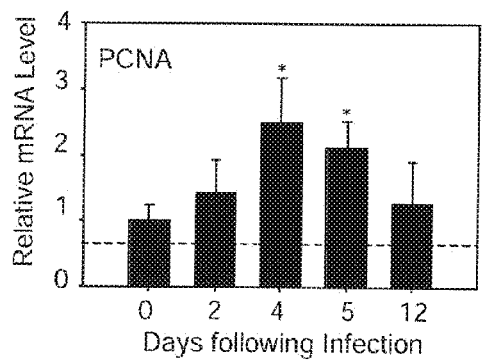
FIG. 21A-E. Effect of SULT2B1b overexpression on proliferative gene expressions in mouse liver tissues. Following infection with Ad-Control or Ad-SULT2B1b, mice were sacrificed at the days as indicated. Total mRNAs were prepared from liver tissues, and each mRNA level was analyzed by RTqPCR. (A) PCNA; (B) FoxM1b; (C) CDC25b; (D) Cyclin A; (E) MMP-9 expressions at mRNA level. The results are shown as mean±S.D. (n=3-5/group) *P<0.05 vs. day 0.
Figure 21B:
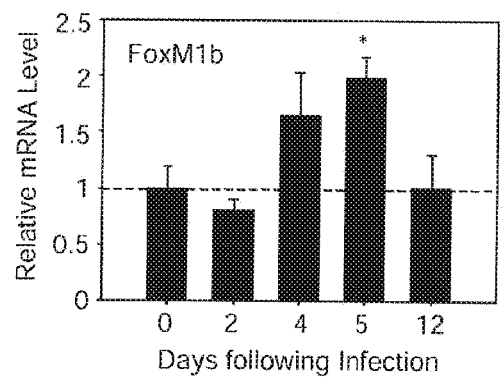
Figure 21C:
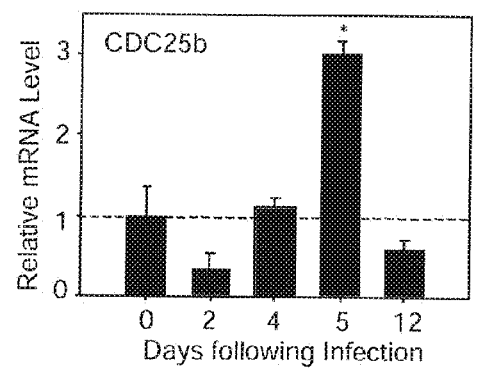
Figure 21D:
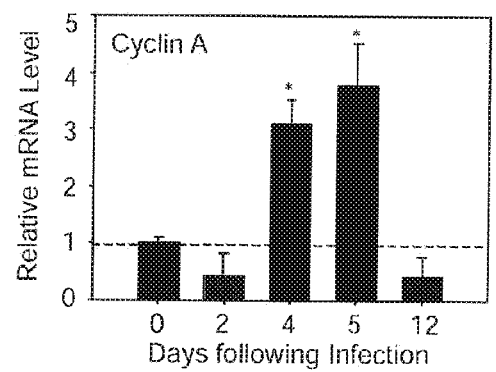
Figure 21E:
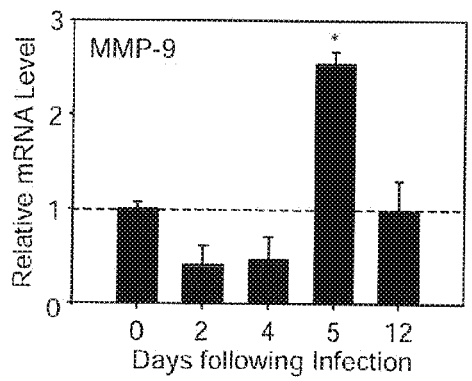

The mRNA levels of other proliferative genes were determined by RTqPCR in mouse liver tissues. As depicted in FIG. 21, when the expression of SULT2B1b reached its highest level (day 4 or 5), the tissues produced strong 2- to 4-fold increases in mRNA levels of PCNA (FIG. 21A), forkhead Box m1b (FoxM1b, (FIG. 21B), cell division cycle 25b (CDC25b, (FIG. 21C), and cyclin A (FIG. 21D). FoxM1b and its target gene CDC25b are known to be essential in cell cycle progression through G1/S and G2/M and cyclin A is a protein required for the cell to progress through the S phase. In addition, 2.6-fold increase of mRNA level for matrix metalloproteinase-9 (MMP-9, FIG. 21E) was observed in mouse liver tissues at day 5 after Ad-SULT2B1b injection. MMP-9 is a zinc endopeptidase involved in the breakdown of extracellular matrix in normal physiological processes and tissue remodeling in the regenerating liver. Thus, increases in SULT2B1b expression may promote liver proliferation in vivo.

Effect of SULT2B1b on LXR Activity and its Target Gene Expression in the Mouse Liver Tissues.

Figure 22A:
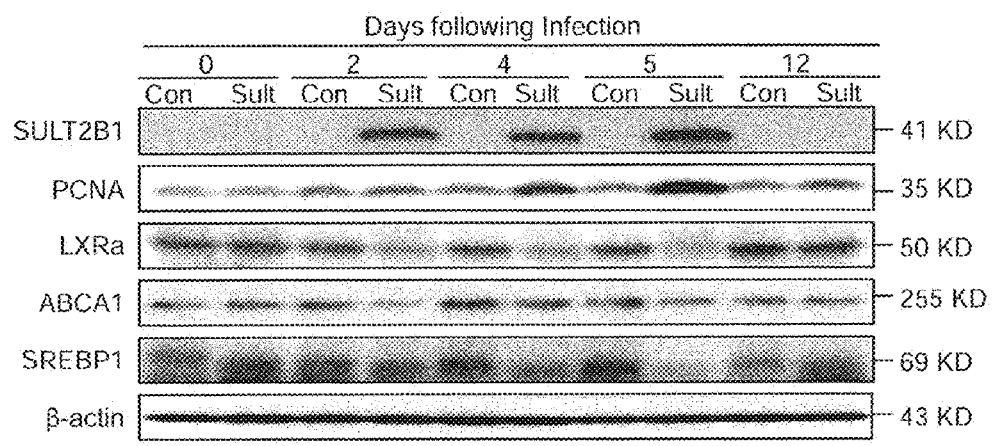
FIGS. 22A and B. Effect of SULT2B1b overexpression on LXR and its target gene expressions in mouse liver tissues. Mice were sacrificed at the days as indicated following Ad-Control or Ad-SULT2B1b infection. (A and B) The hepatic SULT2B1b, PCNA, LXRa, ABCA1 and SREBP1 protein levels in the control (black bars) and SULT2B1b (gray bars) groups were analyzed by western blot. The results are shown as mean±S.D. (n=3-5/group) #P<0.05 vs. Con.
Figure 22B:
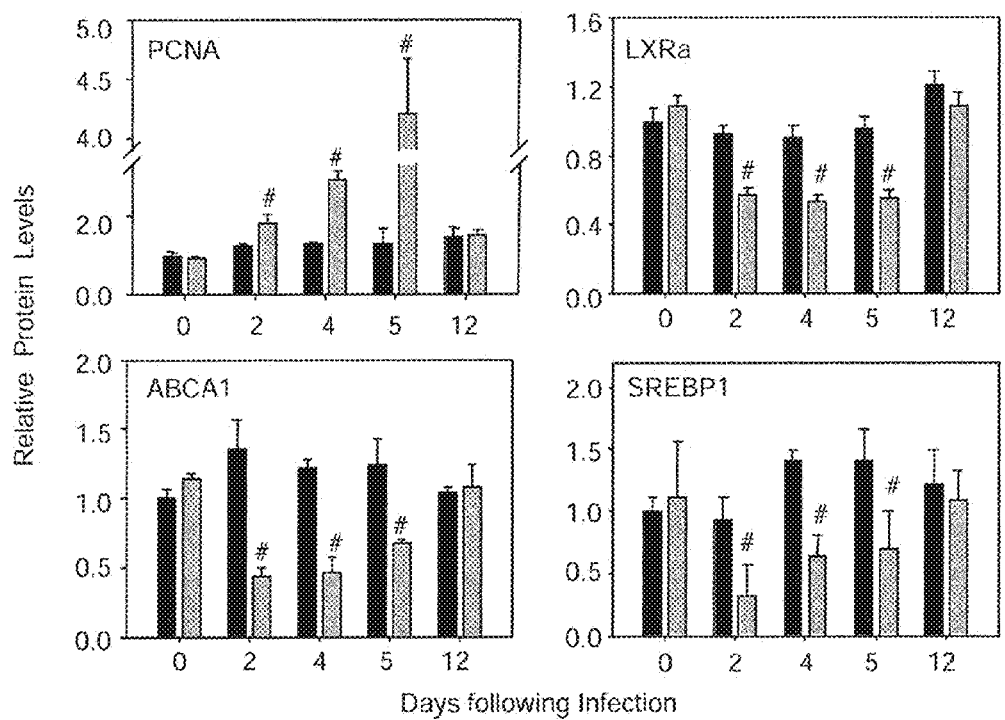

To understand the possible mechanisms by which SULT2B1b promotes hepatic proliferation, the expression of genes regulated by LXR signaling pathway were analyzed in mouse liver tissues. As shown in FIGS. 22A and B, infection of mice for 2 to 5 d with Ad-SULT2B1b inhibited the activity of LXR response in liver, the protein levels of LXRa and its target genes ABCA1 and SREBP-1c in the SULT2B1b group decreased by >40%, >50%, and >70%, respectively. These results in vivo were consistent with previously reported studies showing inactive effect of SULT2B1b on LXR response. Recent reports indicate that LXR activation induces growth arrest and inhibits proliferation in many cells and animal models. Thus, the stimulation of proliferation by SULT2B1b is most likely via the inactivation of LXR signaling.

Effect of LXR Agonists on SULT2B1b-Induced Proliferation in Mouse Liver Tissues.

Figure 23A:
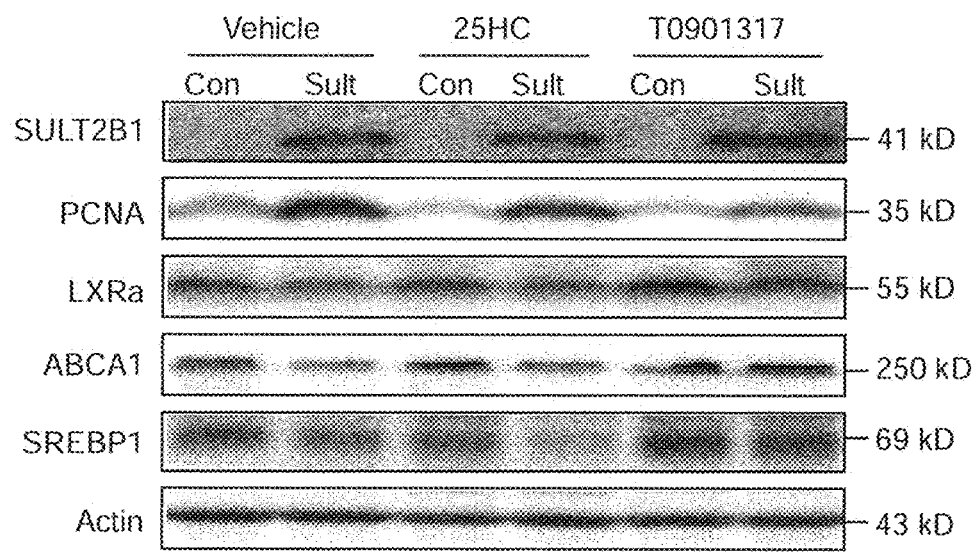
FIGS. 23A and B. Role of LXR signaling in SULT2B1b-induced proliferation in mouse liver tissues. Following infection with Ad-Control or Ad-SULT2B1b, mice were then given intraperitoneal injections of 25HC or T0901317 (25 mg/kg) for every two days, and sacrificed at day 5. (A and B) The hepatic protein levels of SULT2B1b, PCNA, LXR and its target genes ABCA1 and SREBP1 were analyzed by western blot. The results are shown as mean±S.D. (n=3-5/group) *P<0.05 vs. corresponding vehicle, #P<0.05 vs. Con.
Figure 23B:
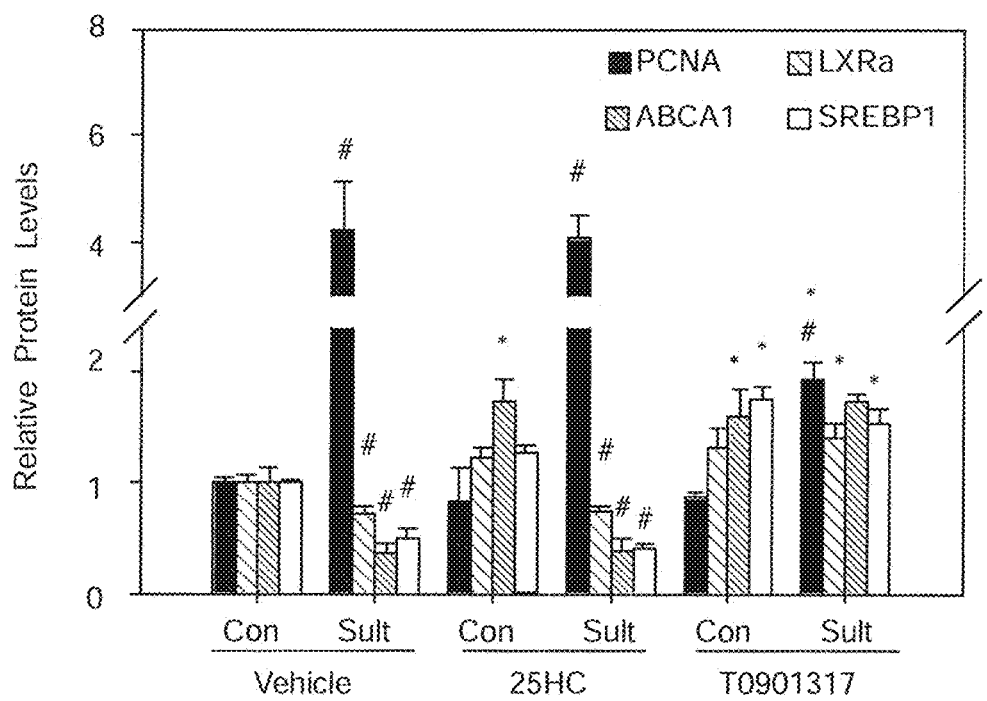

Synthetic T0901317 and natural 25HC are LXR agonists. T0901317 can impair SULT2B1b overexpression-induced LXR inactivation, while 25HC cannot. To determine whether the SULT2B1b-induced proliferation depends on LXR signaling repression, we compared the effect of these two LXR agonists in mouse liver. Briefly, mice with virus administration for 5 days were given intraperitoneal injections of 25HC or T0901317 as described in Methods. The results demonstrated that SULT2B1b overexpression indeed resulted in increased PCNA expression and repressed LXR activation in the presence of vehicle or 25HC, as compared to the corresponding control groups. However, the presence of T0901317 significantly blocked the SULT2B1b-stimulated PCNA expression by 2- to 4-fold (FIGS. 23A and B). These in vivo data clearly indicate the involvement of LXR signaling in SULT2B1b-induced proliferation.

Effect of SULT2B1b on Proliferation in Primary Rat Hepatocytes.

Figure 24A:
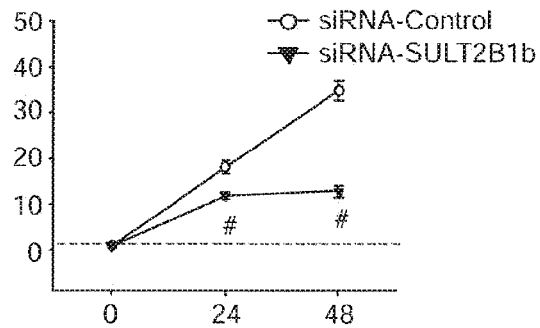
FIG. 24A-F. Effect of siRNA-SULT2B1b on proliferation in PRH. PRH at a confluency of 100% were transfected with siRNA-SULT2B1b or siRNA-control for 24 and 48 hours as indicated. (A) RtqPCR analysis of SULT2B1b mRNA level after siRNA-SULT2B1b transfection; (B-D) RTqPCR analysis of cell cycle regulatory gene mRNA levels, including CDK2, FoxM1b, cyclin A and PCNA; (F) Relative hepatocyte viabilities were measure by cell survival assay. The OD value of cell cultured in normal (N) was arbitrarily assigned as 100%. Data are the mean±S.D. of three determinations. *P<0.05 vs. N, #P<0.05 vs. siRNA-Control.
Figure 24B:
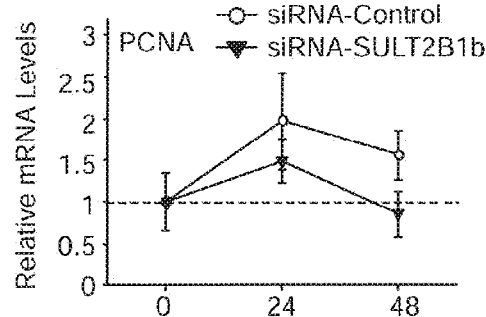
Figure 24C:
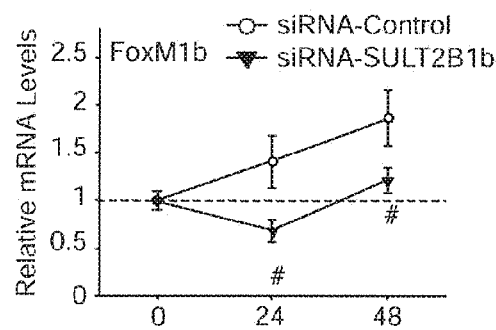
Figure 24D:
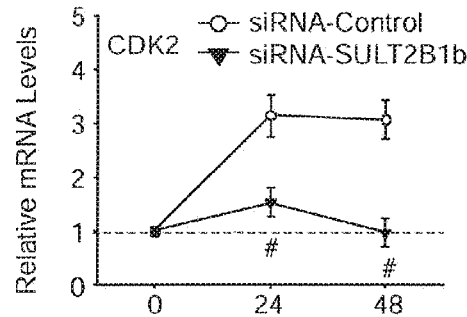
Figure 24E:
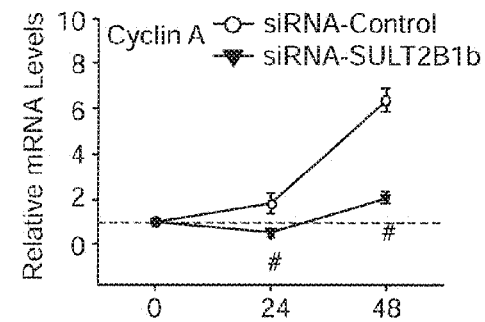
Figure 24F:
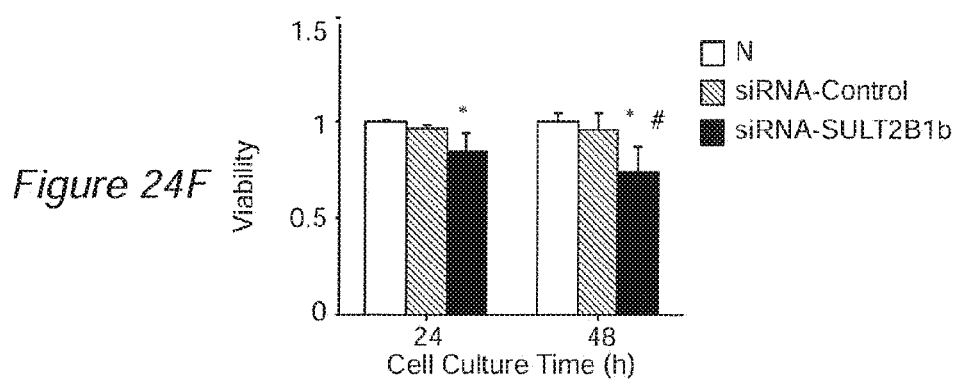
Figure 28A:
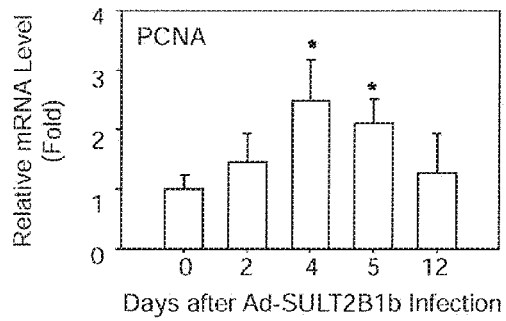
FIG. 28A-F. Effect of SULT2B1b overexpression on gene expressions involved in proliferation. Mice were infected with Ad-SULT2B1b or Ad-control (1×10[8] pfu) as indicated. Each group contained 3-5 mice. A-F: RTqPCR analysis of PCNA, Cyclin A, FoxM1b, CDC25b, MMP-9 and C-myc, expressions at mRNA level. * Represents P<0.05 vs. time-point 0.
Figure 28B:
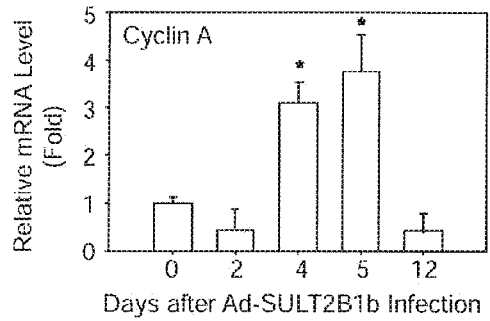
Figure 28C:
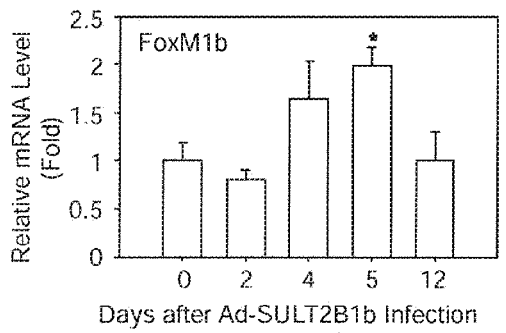
Figure 28D:
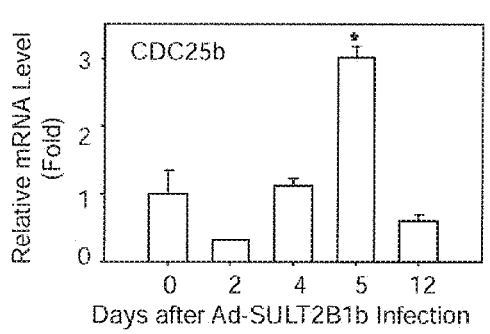
Figure 28E:
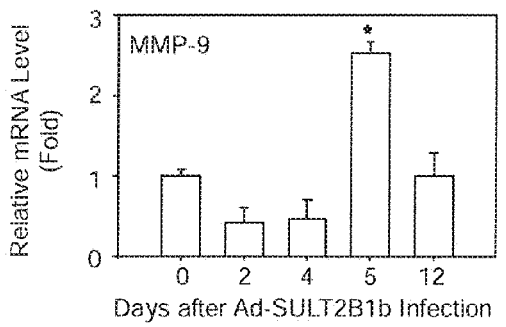
Figure 28F:
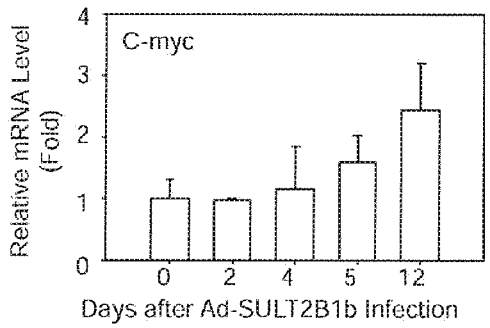

To study the effect of SULT2B1b on the hepatic proliferation gene expression, the loss-of-function studies were performed using siRNA-SULT2B1b in PRH, which had shown relative high level of SULT2B1b expression. As reported previously, rat SULT2B1b mRNA level in the control group gradually increased with time in culture, and reached up to 35-fold at the 48 h (FIG. 24A). The expressions of cell cycle regulatory genes PCNA, FoxM1b, CDK2, and cyclin A in the control group were also upregulated with time in culture (FIG. 24 B-E). However, when the SULT2B1b levels were efficiently (about 50%-70%) silenced following siRNA-SULT2B1b transfection (FIG. 24A), the mRNA levels of these proliferative genes were substantially repressed (FIG. 24C-E). These results demonstrated that PRH are potential proliferation cells and their proliferation capacity may be regulated by SULT2B1b expression. As expected, cell survival assay demonstrated an effective reduction of cell viability in SULT2B1b-silenced hepatocytes, as compared to the cells infected with siRNA-Control and cultured in normal (N) (FIG. 24 F), supporting our RTqPCR analysis. Effect of SULT2B1b on proliferation of PRH was also assessed by SULT2B1b overexpression. As shown in FIG. 25A, infection of PRH with Ad-SULT2B1b at a MOI of 10 pfu/cell for 24 h-48 h produced high SULT2B1b protein levels. Simultaneously, the hepatic proliferation potential was substantially promoted at 48 h as investigated through cell survival assay (FIG. 25B). RTqPCR showed that in contrast with the loss-of-function results described above, SULT2B1b overexpression in PRH led to a further increase (about 2-fold) in the mRNA levels of the proliferative genes PCNA, FoxM1b, CDK2 and cyclin A (FIG. 25C). Thus, similar to that in mouse liver tissues, SULT2B1b expression may promote hepatocyte proliferation in vitro.

Effect of LXR Agonists on SULT2B1b-Induced Proliferation in PRH.

The role of LXR signaling in SULT2B1b-induced proliferation was further demonstrated by in vitro application of T0901317 and 25HC in PRH. First, the effect of SULT2B1b on LXR signaling and PCNA protein levels was investigated. As shown in FIGS. 26A and B, the LXR and SREBP1 protein levels in the control group gradually decreased with time in culture, and SULT2B1b overexpression further decreased the levels at 24 and 48 h. For the proliferative marker PCNA, Ad-SULT2B1b infection increased its protein level by 8-fold at 48 h (FIGS. 26A and B). Hence, 48 h was chosen for the following studies. As the western blot analysis shown in FIG. 29C, for the Ad-Control-infected group, treatment of cells for 48 h with either T0901317 or 25HC significantly increased LXR response gene expressions and decreased PCNA expression. Compared with cells treated with only virus (Ad-Control or Ad-SULT2B1b) infection for 48 h (FIGS. 26A and B), the addition of 25HC results in a similar downregulation of LXR response and upregulation of PCNA expression after SULT2B1b overexpression, while slight but no significant change was detected in the presence of T0901317 (FIGS. 26 C and D), indicating that the activation of LXR by T0901317 blocks the SULT2B1b-induced proliferation. These in vitro data further confirm that the effect of SULT2B1b on proliferation in vitro is LXR signaling pathway dependent.

Discussion

In this study, we found that FoxM1b, CDK2, and cyclin A gene expressions are significantly (>2-fold) increased in cultured PRH at 24-48 h compared to 0 h. This increase in proliferative genes may play a role in hepatic survival in response to liver injury. Interestingly, SULT2B1b expression is also enhanced (20-35 fold) with time in PRH culture, and SULT2B1b inhibition by siRNA results in significant downregulation of these cell cycle regulatory genes. The present data signify the fact that the increasing level of SULT2B1b expression is crucial for the proliferation of hepatocytes in culture.

We also showed that LXR signaling pathway is downregulated with time in PRH culture as seen by western blot. In fact, this downregulation of LXR response in PRH is similar to that in liver after partial hepatectomy: during liver regeneration, significant inactivation of LXR signaling is observed following partial hepatectomy, and this is accompanied by increases in SULT2B1b. In view of our results in normal mouse livers and primary hepatocytes that SULT2B1b overexpression substantially represses LXR response, it is reasonable to conclude that LXR signaling pathway may play a role in SULT2B1b-induced proliferation. Furthermore, the data in cultured hepatocytes showed that both LXR signaling activity and PCNA expression are regulated by SULT2B1b, whereas the times differ: LXR inactivation occurs earlier than the upregulation of PCNA. This can be explained based on our data where we studied the effect of LXR agonist T0901317 on SULT2B1b-induced proliferation in PRH. Considering that the enhanced PCNA protein level and repressed LXR response induced by SULT2B1b overexpression are blocked by T0901317, LXR signaling pathway must play an important role in SULT2B1b-induced proliferation in vitro. Thus, that the repression of LXR response occurs earlier (24 h) than the upregulation of PCNA expression (48 h) is not surprising.

We saw that SULT2B1b overexpression increased PCNA-positive cells and PCNA protein levels in a dose- and time-dependent manner in mouse liver tissues. When LXR was activated in vivo, SULT2B1b retained part of its ability to induce PCNA. In fact, we also observed a direct relationship between SULT2B1b and PCNA expression in vivo by double immunofluoresence.

In summary, we for the first time provide convincing evidence that SULT2B1b may promote hepatic proliferation via increasing cell cycle regulatory gene expressions in vivo and in vitro. By application of the synthetic LXR agonist, we further found that LXR signaling is a key factor in SULT2B1b-induced proliferation. The results demonstrate a previously undefined function of SULT2B1b in liver, and suggest a role in regulating liver regeneration and the re-growth process.

Example 5

SULT2B1b Overexpression Promotes Liver Regeneration via Inhibiting LXR Signaling in Primary Rat Hepatocyte and Mouse Liver with or without Partial Hepatectomy In the present Example, we demonstrate that SULT2B1b plays a critical role in liver regeneration by inhibiting the LXR signaling pathway. Increases in SULT2B1b in mouse liver tissues with or without PH upregulate PCNA-positive cells in a dose- and time-dependent manner while decreases in SULT2B1b significantly inhibit many proliferative gene expressions in PRH. Activation of LXR pathways in PRH by synthetic agonist completely blocks the SULT2B I b-induced increases in PCNA. The results provide novel therapeutic indications for liver injury, transplantation and surgery.

Materials and Methods

Animals and Treatment.

C57BL/6 female mice were obtained from Charles River Laboratories (Cambridge, Mass.). Mice were hosted under a standard 12/12-hour dark-light cycle with standard rodent chow diet and water ad libitum. Nine- or 10-week-old mice were infected with recombinant adenovirus encoding CMV-driven SULT2B1b ($1 \times 10^8$ pfu/mouse) through tail vein injection. Ad-CMV-Gal adenovirus was used as control. For the PH animal model, PH was performed under anesthesia following infection of the mice at the days as indicated in the text using Higgins and Anderson's methods. Briefly, left lateral and median lobes were completely removed. For the sham-operated controls, an excision was made into the peritoneal cavity followed by closure of the incision. At indicated times after surgery, mice were sacrificed by isoflurane inhalation, and serum and liver tissues were collected. To measure the liver re-growth rate, the collected liver tissue from each group of mice (n=3-4) were weighed and compared to the body weight at the time of sacrifice. To evaluate liver injury, the liver-specific cytosolic enzyme activities of aspartate aminotransferase (AST), alanine aminotransferase (ALT) and alkaline phosphatase (ALP) in serum were measured using standard clinical biochemistry laboratory blood assays. All protocols were approved by the Institutional Animal Care and Use Committee (IACUC) of the McGuire VA medical center.
Culture of PRH PRH cultures, prepared as previously described (Hylemon et al., J Biol Chem 1992: 267; 16866-16871), were plated on 60-mm tissue culture dishes in Williams' E media containing thyroxine (1 µM) and dexamethasone (0.1 µM). Cells were infected with Ad-CMV-SULT2B1b at a multiplicity (MOI) of 10 plaque forming units/cell (pfu/cell) or 100 nM of siRNA-SULT2B1b (ON-TARGET plus siRNA of rat SULT2B1b, Thermo Scientific Dharmacon, USA). Ad-CMV-β-Gal adenovirus and ON-TARGET pius negative control siRNA were used as controls respectively.
Immunohistochemistry Liver tissues were fixed in 10% buffered formalin and embedded in paraffin. Deparaffinized 4-µm sections were stained with mouse anti-PCNA antibody (ab29, Abcam, Mass., USA). Immobilized antibodies were detected by the avidin-biotin-peroxidase technique (Vectastain ABC Kits, Vector Laboratories, UK). DAB was used as the chromogen and haematoxylin as the nuclear counterstain. The primary antibody was omitted as negative control. For quantitation of PCNA expression, PCNA-positive and PCNA-negative nuclei were counted in at least five high-power fields each slide and expressed as the percentage of PCNA-positive cells.
Double Immunofluorescenc.

Liver tissue in mice 4 days after Ad-SULT2B1b infection was used for double immunofluorescence to co-locate the expression of PCNA with SULT2B1b. Deparaffinized 4-µm sections were cultured with a cocktail mix of two primary antibodies: mouse anti-PCNA antibody (1:800; ab29, Abcam, Mass., USA) and rabbit anti-SULT2B1b antibody (1:30; AB38412, USA). Subsequent antibody detection was carried out with secondary antibodies: Alexa Fluor 488 goat anti-mouse IgG (1:500; Invitrogen, USA) and Alexa Fluor 488 goat anti-rabbit IgG (1:500; Invitrogen, USA). Negative control was performed by replacing the primary antibody with PBS. Sections were examined with a fluorescence microscope and merged images were formed using Adobe Photoshop CS2.
Determination of Gene Expressions Involved in Proliferation and LXR Pathway.

Total cell lysate was prepared from frozen mouse liver tissue or PRH, and 50 pg total proteins were subjected to 10% SDS-PAGE, transferred to polyvinylidene difluoride membranes (Millipore, Eschbom, Germany). The membranes were probed with antibodies against PCNA, SULT2B1b (Santa Cruz, Calif.), LXRα (Abcam, Cambridge, Mass.), ABCA1 (Abcam, Cambridge, Mass.), SREBP1 (Santa Cruz, Calif.) and actin (Sigma, USA) as a loading control for 2 h at room temperature. Western blot analysis was performed as previously described (Ren et al., J. Lipid Res. 2004; 45:2123-2131).

Total RNA was extracted using SV Total RNA Isolation Kit (Promega, Wisconsin, Wis.) according to the supplier's instruction. The relative mRNA levels were measured by RT-PCR and quantitative real-time PCR(RTqPCR) as previously described (Ren et al., J. Lipid Res. 2004; 45:2123-2131). Expression levels were normalized to the 18S gene or GAPDH. Suitable oligonucleotide primers for RTqPCR were employed.
HPLC Analysis of Oxysterols in Liver Tissue.

Mouse liver samples (300 Mg) that come from three biologically-distinct specimens were pooled together to reduce variance and digested by 2 mg/ml of Proteinase K in PBS (1 ml) at 50° C. for 12 h. 20 ml of chloroform:methanol (2:1, v/v) was added to the digests, sonicated for 30 min, and filtered, 4 ml of water was added, mixed, and allowed to stand for about 3 h for phase separation. The chloroform (bottom) phase, which mainly contains oxysterols, was added 30 µl of testosterone in chloroform solution (50 µg/ml) and evaporated under nitrogen stream. The residue was re-suspended in 8 mL of hexane and passed through a pre-conditioned Waters Sep-Pak silica cartridge (400 mg) that had been washed with hexane (5 ml) and 1% isopropanol in hexane (5 ml). The purified oxysterols fraction was eluted with 8 ml of isopropanol:hexane (1:9, v/v) and evaporated under $N_2$.

The oxysterol samples thus obtained from the chloroform were oxidized with cholesterol oxidase. To the oxysterol sample dissolved in 50 µl of 2-propanol were added 450 µl of water and 50 µl of 1M potassium phosphate buffer (Kpi), and the resulting mixture was sonicated for 10 min. To the mixture 4 units of cholesterol oxidase in Kpi buffer (10 µl) was added and incubated at 37° C. for 1 h. Methanol (300 µl) was added to stop the reaction and the products, enones, were extracted with 3 times with 2 ml of hexane, and the extracts were evaporated under an $N_2$ stream. The residue was re-dissolved in 5% isopropanol in hexane (150 µl) and 100 µl of the solution was subjected to the HPLC as described below.

HPLC analysis was conducted with Alliance 2695 separation module fitted with 2487 Dual λ absorbance detector (Waters, Milford, Mass.). The separation was carried out on an Ultraspere silica column (5 µm, 4.6 mm id×250 mm; Beckman, Urbana, Ill.) and hexane: isopropanol:acetic acid=965:25:10 (by volume) as an eluent at a flow rate of 1.3 ml/min. The column temperature was kept constant at 30° C. and the enones were monitored at the absorption at 240 nm.
Statistical Analysis.

Data are expressed as mean±standard deviation (SD). Statistical comparison was made using Student's t test for unpaired samples. A value of P<0.05 was defined as statistical significance.
Results Effect of SULT2B1b on PCNA Expression in Mouse Liver.

Proliferation cell nuclear antigen (PCNA) is a critical protein required for DNA replication in proliferating cells. To elucidate the growth regulation by SULT2B1b in liver, we used PCNA as the proliferation marker. Mice were infected with Ad-SULT2B1b or Ad-control ($1\times10^8$ pfu) through tail vein injection. Mouse liver was harvested at 0, 2, 4, 5 and 12 days after SULT2B1b infection. RTqPCR analysis showed that the mRNA level of SULT2B1b gene expression increased to its highest level (about 150-fold) at the fourth or fifth day (D4 or D5) and returned steadily to the normal level at the twelfth day (D12) (FIG. 27A). Immunohistochemistry analysis showed the number of PCNA-positive cells was significantly increased following increases of SULT2B1b expression in liver, as compared to DO (FIGS. 27B and C). Consistently, SULT2B1b overexpression also significantly increased the total protein levels of PCNA. (FIG. 27D).

Co-Localization of PCNA and SULT2B1b Expression in Mouse Liver Hepatocytes.

To elucidate the role of SULT2B1b in the expression of PCNA, mice were infected with Ad-SULT2B1b or Ad-control as described above. Four days after infection, PCNA and SULT2B1b expressions in paraffin sections of mouse liver tissues were analyzed by double immunoflorescent staining (not shown). The merged images indicated that the hepatocytes with PCNA expression in the nuclei are almost always accompanied by SULT2B1b overexpression in the cytosol, while there was no PCNA expression in the cells without SULT2B1b overexpression, indicating the direct relationship between SULT2B1b and PCNA. The number of PCNA and SULT2B1b positive cell was difficult to detect in mouse liver infected with control virus (data not shown).

Effect of SULT2B1b on Gene Expression Involved in Proliferation in Mouse Liver.

To confirm the impact of SULT2B1b on promoting liver proliferation in mouse liver, the mice were infected with Ad-SIILT2B1b or Ad-control as described above. RNA was exacted from liver tissue and the relative mRNA level of each gene was measured by qRTPCR. As the expression of SULT2B1b reached to its highest level (at day 4 and day 5), the mRNA level of four well-known proliferative genes were substantially increased: PCNA, for DNA replication in proliferation cells; forkhead Box m1b (FoxM1b) and its target gene CDC25b, for the cell progression through GuS and G2/M phases; CyclinA, for GuS transition, and matrix metalloproteinase-9 (MMP-9), a zinc endopeptidase, for hepatic matrix remodeling in the regenerating liver, and C myc (FIG. 28A-F).

Figure 29A:
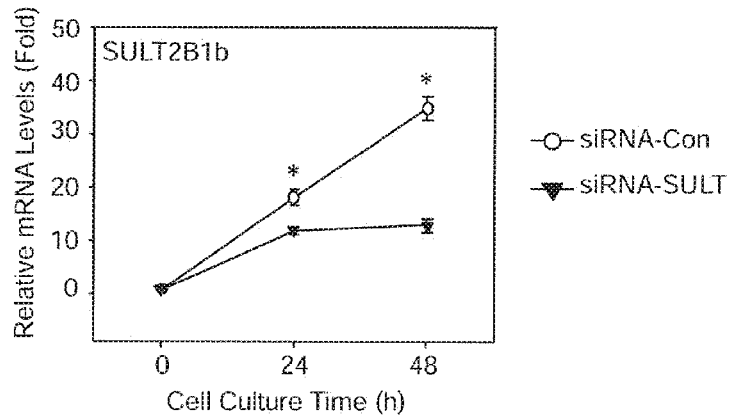
FIG. 29A-E. Effect of siRNA-SULT2B1b on proliferation in PRH. PRH were cultured and transfected with siRNA-SULT2B1b for 24-48 hrs as described. (A) RTqPCR quantified the expression levels of SULT2B1b after siRNA-SULT2B1b transfection. (C-E) RTqPCR analyzed the gene expressions related to cell cycle, including CDK2, FoxM1b, CyclinA and PCNA. * P<0.05 vs. Control FIG. 30A-E. Effect of SULT2B1b overexpression on LXR and its target gene expressions in normal mouse liver. Mice were infected with Ad-Control or Ad-SULT2BIb (1×10[8] pfu) as indicated. Each group contained 3-5 mice. Total protein and mRNA in liver tissue were extracted. A: Western blot analysis of LXR and its target gene expressions at protein level. B-E: RTqPCR analysis of ABCG1, ABCA1, ABCG5 and SREBP-1 expression at mRNA level. The protein data represent one of three separate experiments. Con, the mice infected with Ad-control virus. Sult, the mice infected with Ad-SULT2B1b. * P<0.05 versus time-point 0.
Figure 29B:
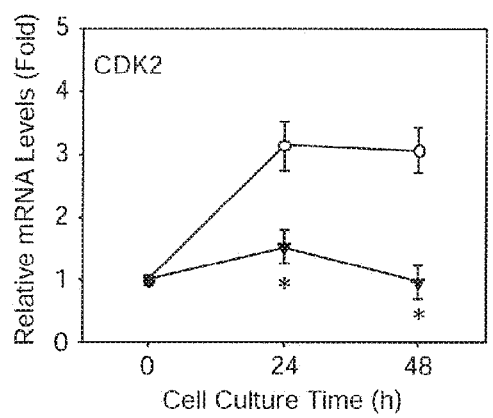
Figure 29C:
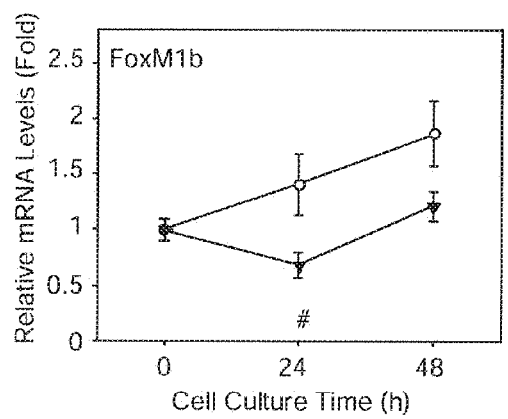
Figure 29D:
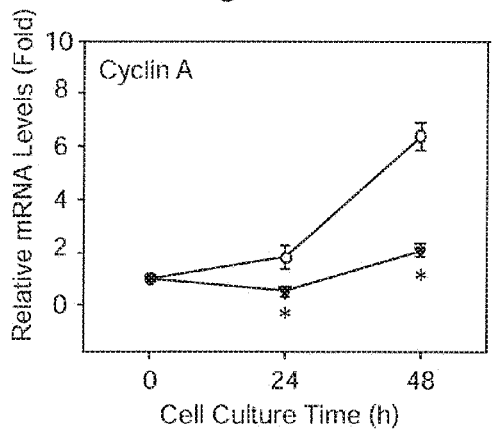
Figure 29E:
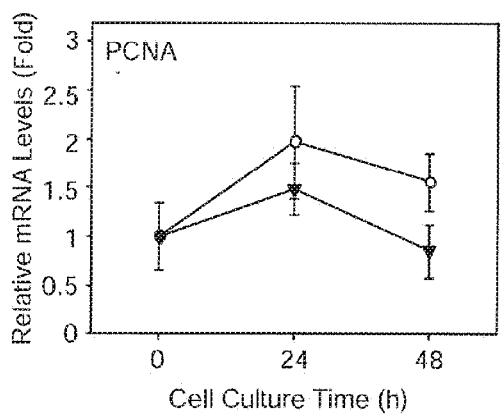

Knockdown of SULT2B1b in PUB: Effect on Gene Expression for Hepatocyte Proliferation To investigate whether SULT2B1b is crucial for hepatocyte proliferation, loss-of-function studies were performed using siRNA-SULT2B1b. Since rat liver expresses much higher SULT2B1b, PRH were selected for this study. During the culture of PRH, as expected, the levels of SULT2B1b gradually increased up to 35-fold at the 48 h time-point (FIG. 29A). Meanwhile, the expression of cell cycle related genes was also up-regulated (FIG. 29B-E). After siRNA-SULT2B1b recombinant plasmid infection, SULT2B1b gene expression was successfully knocked down by 50-60% (FIG. 29A), and the mRNA levels of proliferative genes CDK2, FoxM1b, CyclinA and PCNA were significantly decreased (FIG. 29B-E).

Effect of PH on Expression of SULT2B1b and LXR Signaling Pathway.

PH is the best model for investigating liver regeneration. In order to understand the mechanism of SULT2B1b in promoting proliferation, we used a mouse PH model to detect the expression of SULT2B1b and genes involved in the LXR signaling pathway. Mouse liver tissues were harvested at 0, 1, 3 and 5 days after PH. Total RNA was exacted from liver tissue and gene expression (as mRNA levels) was measured by PCR and RTqPCR. Consistent with previous findings, once PH is performed on a mouse, the liver begins to regenerate, as evaluated by the mRNA level of PCNA (not shown). Interestingly, SULT2B1b expression was significantly up-regulated during this process (not shown), and was accompanied by the suppression of LXR response gene expression, including ABCA1, ABCG1 and SREBP1, as compared by sham-operated mice (not shown). It is possible that the promotional effect of liver proliferation by SULT2B1b is via inhibiting LXR signaling pathway.

Effect of SULT2B1b on Hepatocyte Proliferation Via LXR Signaling Pathway

Figure 30A:
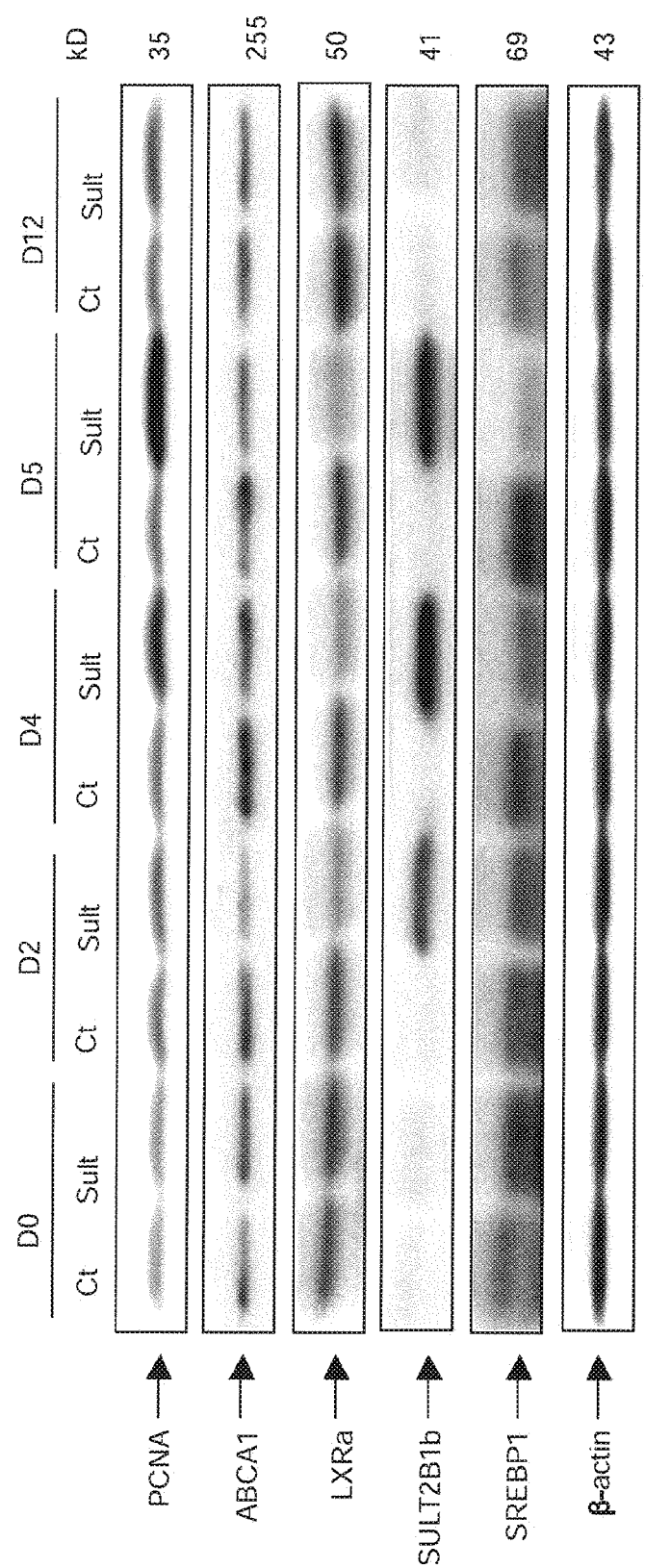
Figure 30C:
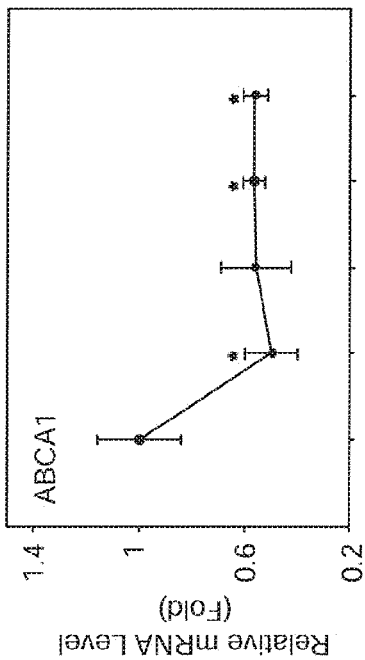
Figure 30E:
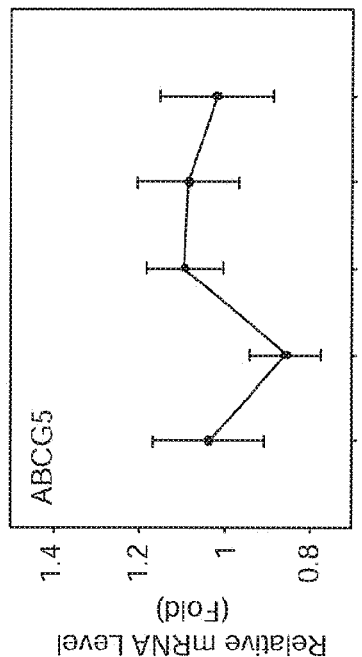
Figure 30B:
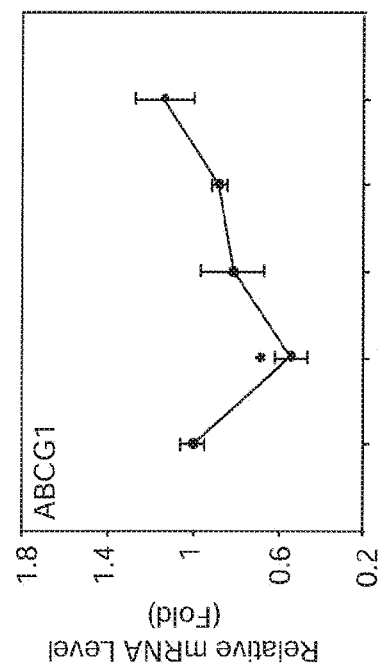
Figure 30D:
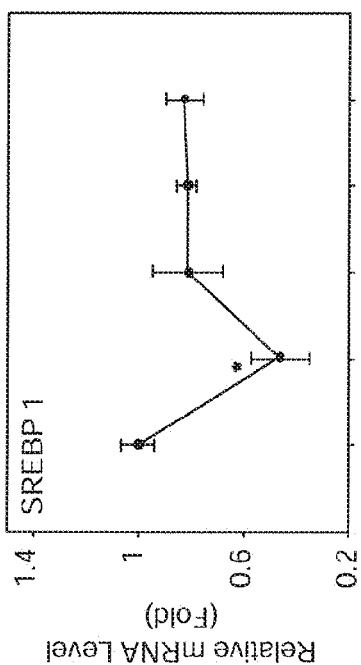
Figure 31A:
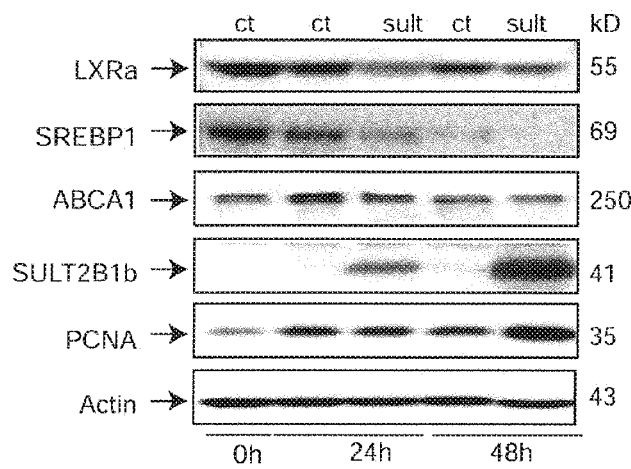
FIG. 31A-H. Effect of SULT2B1b on proliferation via LXR signaling pathway in PRH. PRH were cultured and infected with Ad-control or Ad-SULT2B1b adenovirus (MOI=10) for 24-48 hrs. (A) Western blot analysis of LXR, VSREBP1, ABCA1, SULT2B1b and PCNA protein levels. (B-E) RTqPCR analyzed the gene expressions related to cell cycle, including PCNA, FoxM1b, CDK2, and CyclinA. (F-H) RTqPCR quantified the expression levels of SREBP1, ABCA1 and ABCG5. Samples were harvest 24 hrs after adenovirus infection, the protein levels of SULT2B1b, PCNA, LXR and its target gene were analysed by western blot. The data of western blot represents one of three separate experiments. Con, PRH infected with Ad-control virus. Sult, PRH infected with AdSULT2B1b. * P<0.05 vs. Control FIG. 32A-F. Effect of SULT2B1b overexpression on liver proliferation after PH. Mice were infected with Ad-Control or Ad-SULT2B1b (1×10[8] pfu) as indicated for 5 days. During the five days, mice were subjected to PH and allowed to live for 0, 1, 3 and 5 days. Each group contains 3-5 mice. A: Immunohistochemistry analysis of PCNA expression on liver sections (20× optical field) from mice with virus infection. B: Percentage number of PCNA-positive cells obtained from liver sections at the indicated time-points. C: Liver regeneration after PH was monitored by the ratio of liver to body weight. D-F: Acute liver injury after PH was evaluated by measuring serum AST, ALT and ALP levels. H: RTqPCR analysis of PCNA, C-myc, FoxM1b, CDC25b, Cyclin A and MMP-9 expressions at mRNA level. The data represent one of three separate experiments. Con, the mice infected with Ad-control virus. Suit, the mice infected with Ad-SULT2B1b. * P<0.05 vs. Con.
Figure 31B:
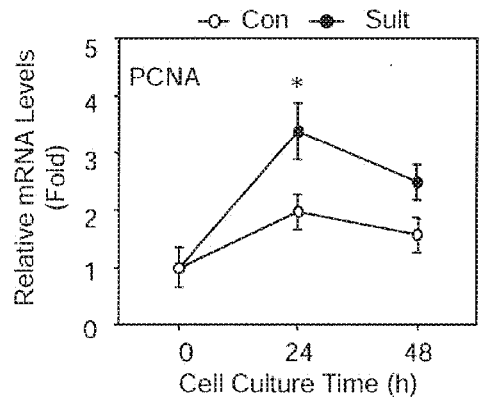
Figure 31C:
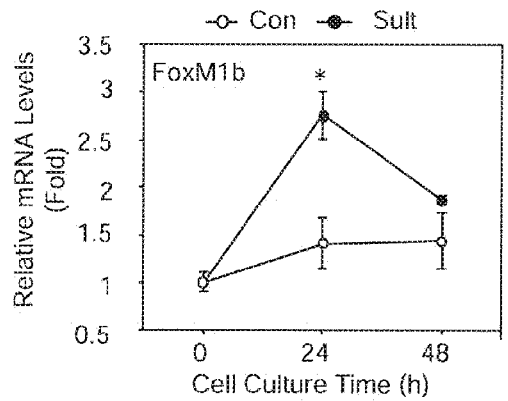
Figure 31D:
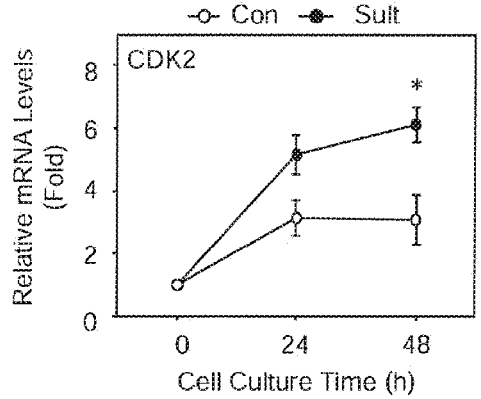
Figure 31E:
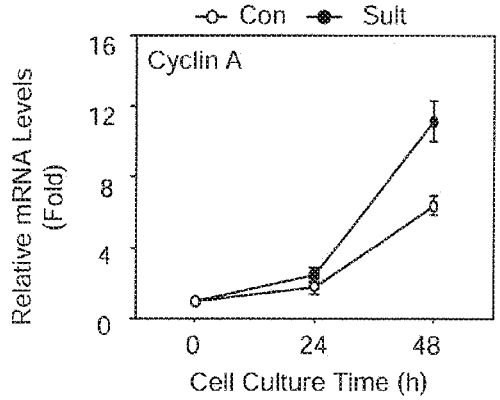
Figure 31F:
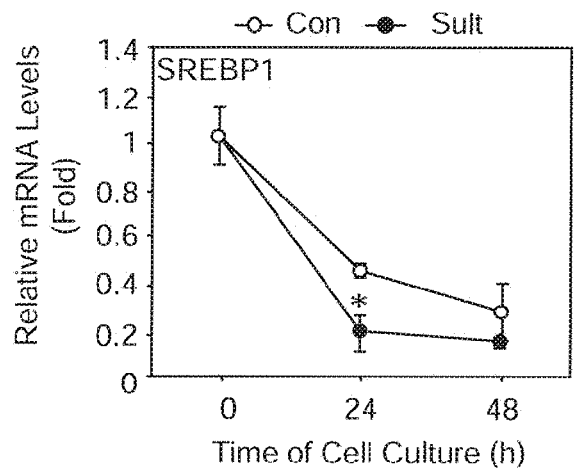
Figure 31G:
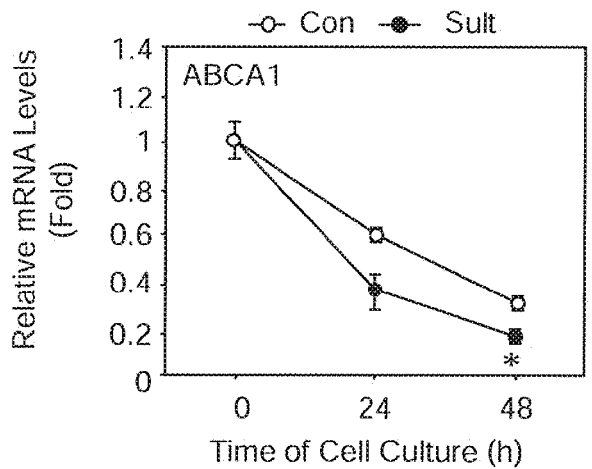
Figure 31H:
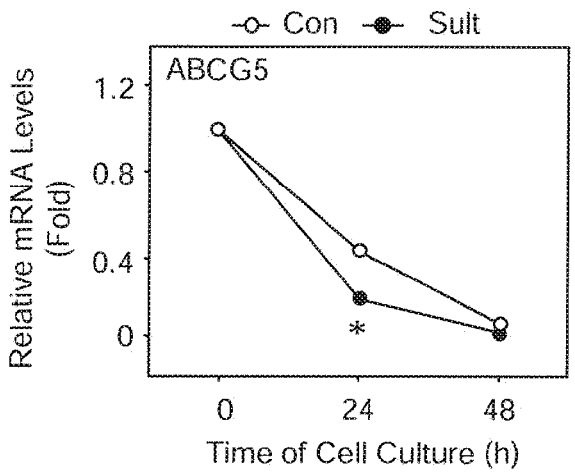

To determine that the effect of SULT2B1b on liver proliferation is through the LXR signaling pathway, we compared the gene expressions involved in LXR signaling pathway between the mice infected with Ad-SULT2B1b and Ad-control mice. As expected, overexpression of SULT2B1b significantly decreased protein levels of LXRa, ABCA1 and SREBP-1 in mouse liver (FIG. 30A). RTqPCR analysis also showed that SULT2B1b overexpression significantly decreased mRNA levels of LXR target genes SREBP-1, ABCA1, ABCG1 and ABCG5 in mouse liver tissues (FIG. 30B-E). The results were consistent with those in PRH (not shown). In the cells with SULT2B1b overexpression, the protein level of PCNA was significantly increased after 48 hours in culture, while the protein levels of LXRcL, ABCA1 and SREBP-1 were significantly decreased at both of 24 and 48 hour time-points (FIG. 31A). SULT2B1b overexpression also increased mRNA levels of PCNA, FoxM1b, and CDK2 (FIGS. 31B-D), and decreased mRNA levels of SREBP1, ABCG5 and ABCA1 compared with those in the cells infected with Ad-ct virus (FIGS. 6F-I1).

Previous studies showed that, T090 1317, as a synthetic agonist of LXR, effectively blocked the effect of SULT2B1b on LXR in human aortic endothelial cells, but not 25HC, the natural ligand which can be sulfated to 25HC3S by SULT2B1b (Bai et al. Atherosclerosis 2011; 214:350-356). To confirm that the impact of SULT2B1b on proliferation is LXR dependent, T0901317 and 25HC were used to compare the effect in PRH. As previously reported, in the cells with control virus infection, both agonists increased LXR response gene expressions, however, the effects of 25HC were impaired by overexpression of SULT2B1b (FIG. 31A). Interestingly, the presence of 25HC further increased the expression of PCNA stimulated by SULT2B1b overexpression, but T0901317 blocked the stimulation by SULT2B1b (not shown).

Figure 32A:
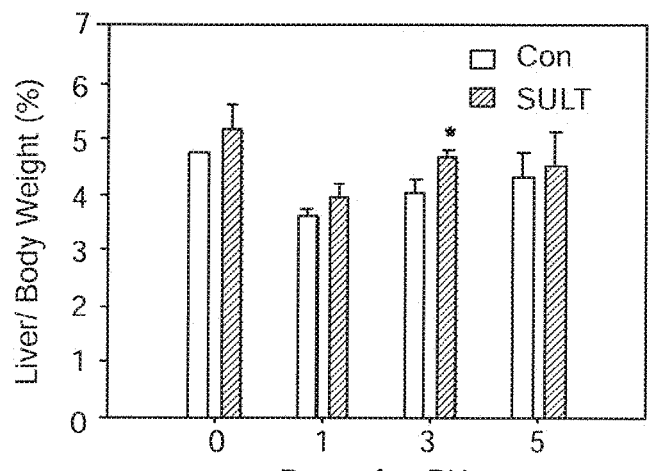

Effect of SULT2B1b Overexpression on Hepatocyte Proliferation During Liver Regeneration To investigate whether SULT2B1b overexpression stimulates hepatocyte proliferation during PH-induced liver regeneration, we infected PH mice with Ad-SULT2B1b or Ad-Control ($1 \times 10^8$ pfu). Livers were harvested and weighed for calculating liver regrowth. Interestingly, mice infected with Ad-SULT2B1b exhibited a faster liver regrowth during the first 3 days after PH and taking only 3 days to achieve their original mass while control mice took 5 days to do so (FIG. 32A).

Figure 32B:
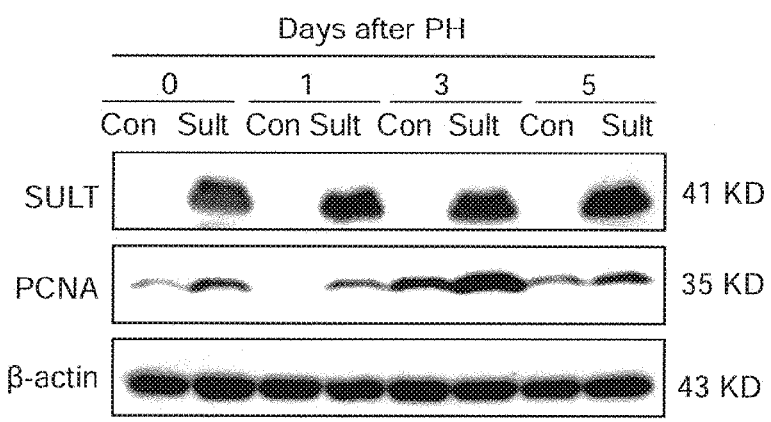
Figure 32C:
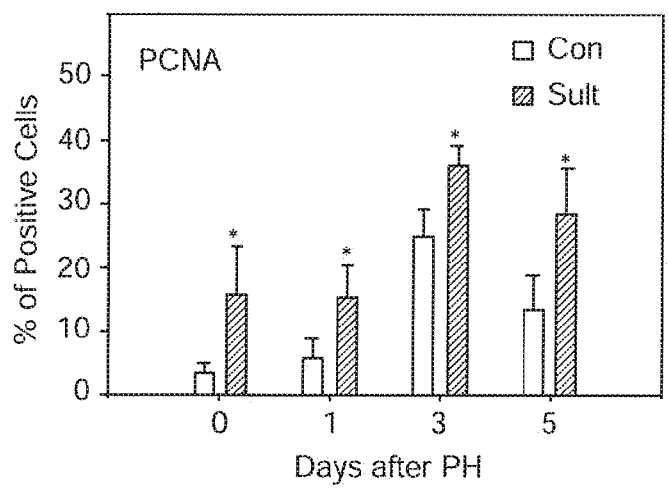
Figure 32D:
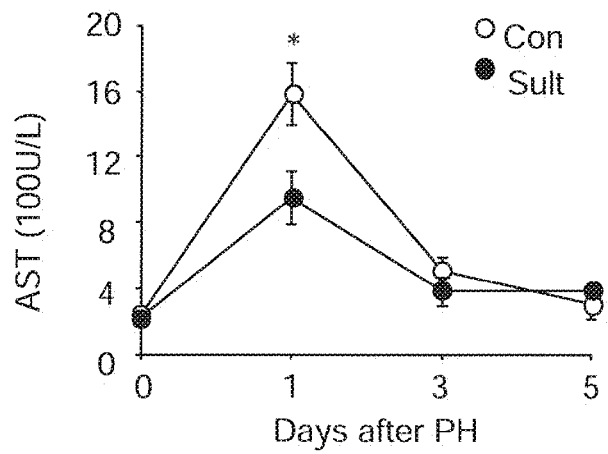
Figure 32E:
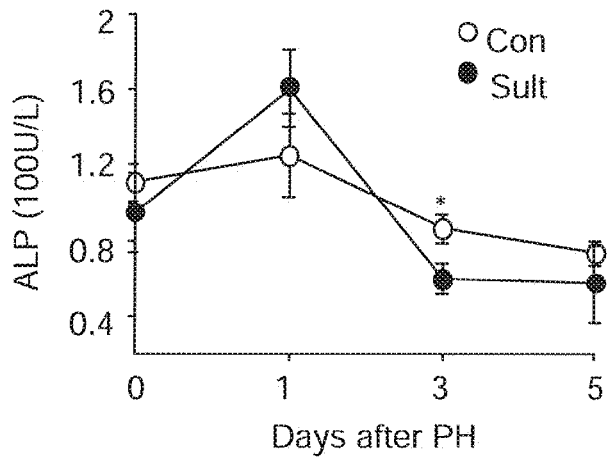
Figure 32F:
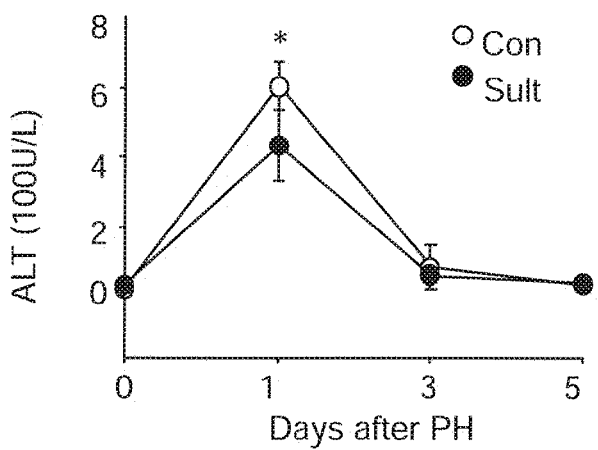

To better understand if SULT2B1b overexpression exerts an impact on the hepatocyte proliferation response, PCNA immunostaining was performed in liver sections. At each time point after PH, the number of PCNA-positive hepatocytes in Ad-SULT2B1b infected mice was substantially increased compared with Ad-Control infected mice (FIG. 32C). Consistently, mice with SULT2B1b overexpression showed significant increases in the protein level of PCNA expression, compared to controls (FIG. 32B). To evaluate whether acute liver injury might influence the regeneration, serum AST, ALT and ALP levels were measured. Compared with Ad-Control infected mice group, strong decreases of AST, ALT and ALP serum levels in AdSULT2B1b infected mice were observed 1 or 3 days after PH (FIG. 32D-F), indicating SULT2B1b significantly decreased liver damage by suppressing inflammation responses. Thus, SUTL2B1b acts positively on liver proliferation after PH, both promoting the hepatocyte proliferation rate and exerting a specific reduction of acute liver injury.

Effect of SULT2B1b Overexpression on Hepatocyte Proliferative Gene Expression During Liver Regeneration.

Figure 33A:
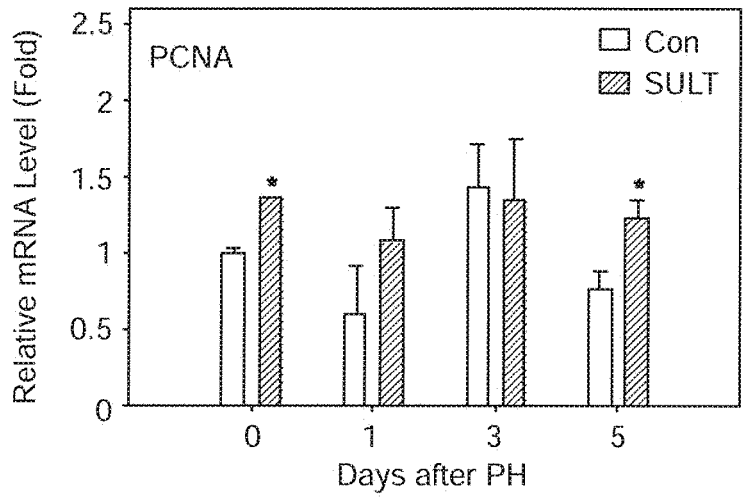
FIG. 33A-F. Effect of SULT2B1b overexpression on hepatocyte proliferative gene expression after PH. Mice were infected with Ad-Control or Ad-SULT2B1b (1×10[8] pfu) for 5 days. During the five days, mice were subjected to PH and allowed to live for 0, 1, 3 and 5 days, as described previously. Total RNAs were purified from mouse liver. Each group contains 3-5 mice. A-F: RTqPCR analysis of PCNA, Cyclin A, FoxM1b, CDC25b, C-myc and MMP-9 expressions at mRNA level. * Represents P<0.05 vs. con.
Figure 33B:
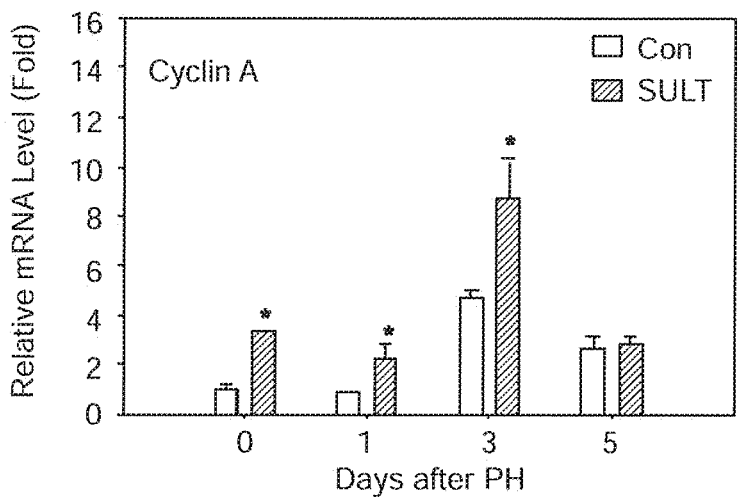
Figure 33C:
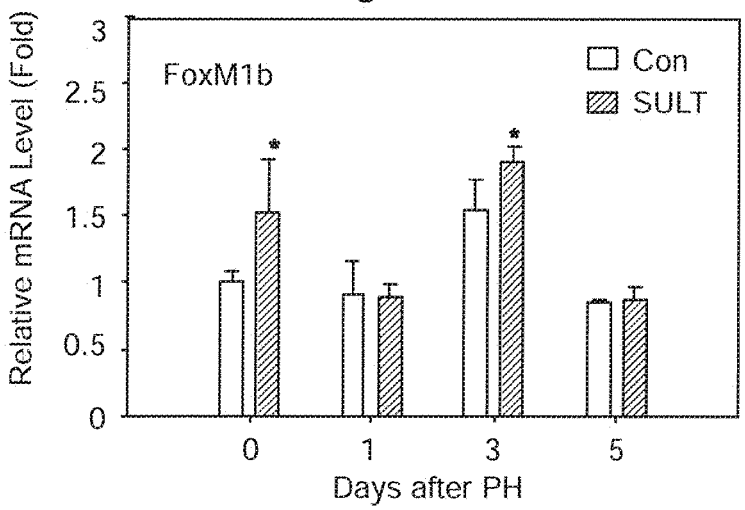
Figure 33D:
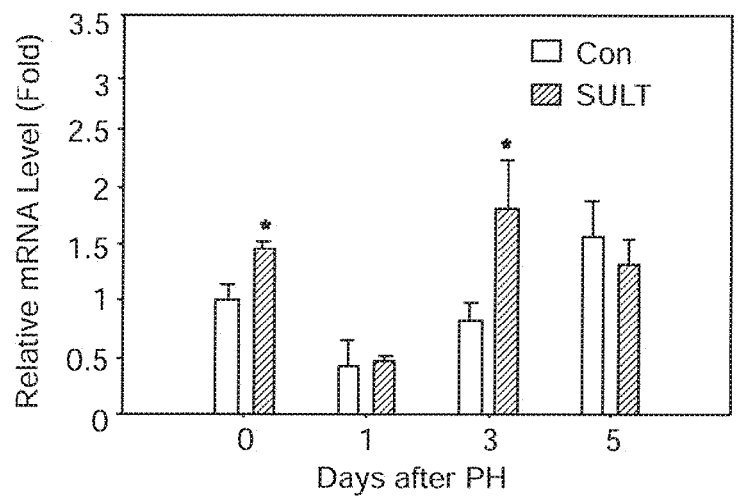
Figure 33E:
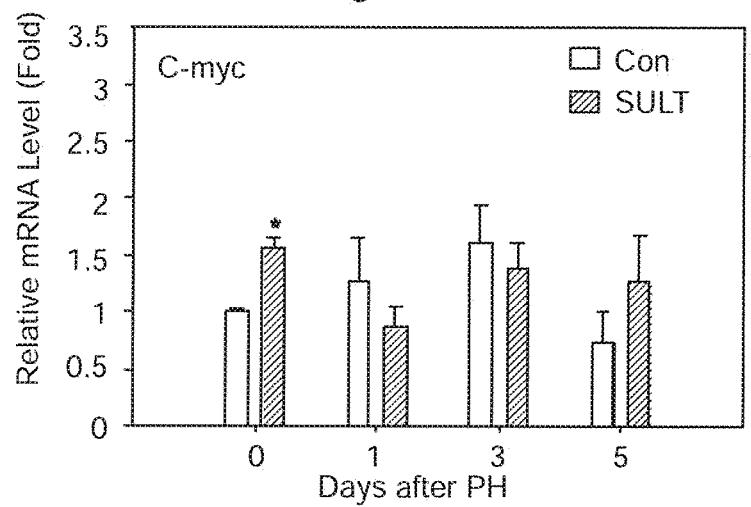
Figure 33F:
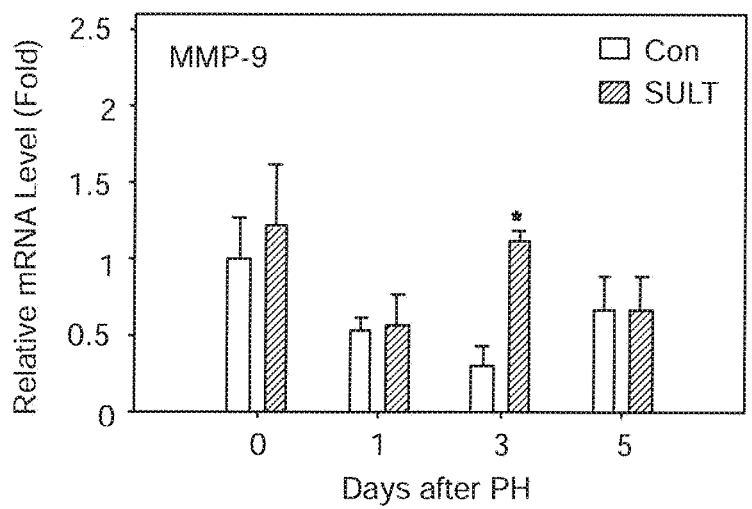

The promotion in hepatocyte proliferative capability by Ad-SULT2B1b infection during liver regeneration was confirmed by RTqPCR. SULT2B1b overexpression led to a significant increase in the expression of proliferative genes involved in the regulation of cell cycle progression, PCNA, CyclinA, FoxM1b, C-myc and CDC25b (FIG. 33A-E). Significant increases in the expression of extracellular matrix remodeling gene MMP-9 was also detected in AdSULT2B1b infected mice, as compared with Ad-Control mice (FIG. 33G). These data confirm that the overexpression of SULT2B1b in the regenerating liver promotes hepatocyte proliferative capability.

Reduction of Hepatic Oxysterol Levels by SULT2B1b Overexpression after PH

In order to investigate whether the down-regulation of the LXR transcriptome is associated with reduction of endogenous oxysterol ligands, we measured the hepatic oxysterol levels at day 0 and 3 after PH. In the Ad-SULT2B1b infected mice, the hepatic amounts of 7-ketocholesterol, 25-hydroxycholesterol, and 6β-hydroxycholesterol were apparently lower compared to those of Ad-Control mice (Table 7). This data reveals a scenario wherein the presence of SULT2B1b there is an apparent reduction of oxysterols coupled with a down-regulation of the LXR system, thus contributing to the significant improvement in proliferative capability in regenerating liver.

TABLE 7

| Oxysterol | 0 days after PH | | 3 days after PH | |
|---|---|---|---|---|
| (ng/g liver) | Control | SULT | Control | SULT |
| 7KC | 1060.1 | 460.8 | 1190.5 | 581.2 |
| 25-HC | 249.5 | 214.7 | 228.6 | 165.3 |
| 6β-HC | 1183.8 | 447.4 | 940.3 | 537.9 |
| 27-HC | 49.04 | — | — | — |

Oxysterols in liver tissue

Discussion

In this report, using PRH and mouse liver with or without PH, we for the first time show that SULT2B1b can promote hepatocyte proliferation. Overexpression of SULT2B1b leads to dramatic increases in the number of PCNA-positive cells in mouse liver with or without PH. Double-immunofluscence provides strong evidence that the increase in PCNA expression is directly related to SULT2B1b overexpression. Furthermore, SULT2B1b overexpression in PP.11 and in mouse liver with or without PH significantly increases expression for a variety of liver proliferative genes PCNA, Cyclin A, FoxM1b, CDC25b, C-myc and CDK2, which are important markers and regulators in proliferation and cell cycle. Conversely, knockdown of SULT2B1b inhibits proliferation in PRH. These results suggest that SULT2B1b is a critical factor in regulating liver proliferation.

These studies also indicate that the effect of SULT2B1b on liver proliferation is also highly associated with the suppression of LXR-driven pathway, as manifested by the decreased expression of LXR and its target genes, SREBP1, ABCAI in the regenerating liver and throughout PRH culture, in both of which can be detected significant increases in the proliferative genes, such as PCNA, CyclinA, CDK2 and FoxM1b.

We detected PCNA expression after SULT2B1b overexpression in PRH in the presence of 25HC or T0901317 and confirmed that overexpression of SULT2B1b in cultured cells impairs LXR response to 25HC but does not alter the receptor response to T090 1317. Simultaneously, PCNA expression is significantly increased in the presence of 25HC, while no significant change of PCNA expression is observed in the presence of T0901317 following overexpression of SULT2B1b. These data indicate that the suppression in LXR response provides a critical step for the action of SULT2B1b on hepatocyte proliferation. SULT2B1b appears to inactivate oxysterols as LXR ligands, therebe inhibiting LXRs signaling pathway, and subsequently activating the expression of cyclin-dependent kinases, promoting cell proliferation.

In this study, SULT2B1b overexpression significantly increased the key cell cycle related genes, CyclinA, CDK2 and FoxM1b in both RPH and mouse liver with or without PH. Furthermore, by comparing the serum cholesterol levels in the mouse with Ad-SULT2B1b or Ad-control infection (Data not shown), we confirmed that the promotional effect of SULT2B1b on liver proliferation is independent of cellular cholesterol levels, because a significant decrease in serum cholesterol levels is detected in the SULT2B1b overexpression mouse group.

In summary, this study provides strong evidence for the first time that SULT2B1b promotes hepatocyte proliferation and liver regeneration via inhibiting LXR signaling pathway in PRH and mouse liver with or without PH. These findings suggest that SULT2B1b plays a crucial role in liver regeneration and suggest novel therapeutic measures for liver transplantation and surgery.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method for promoting liver cell proliferation or liver tissue regeneration in a subject, comprising:
   i) identifying a subject in need of at least one of liver cell proliferation and liver tissue regeneration, and
   ii) elevating a level of 25-hydroxycholesterol-3-sulfate (25HC3S) in said subject by administering to said subject a composition comprising
      25HC3S and
      a physiologically compatible carrier,
   wherein said subject does not have hyperlipidemia, and wherein said elevating promotes proliferation of liver cells or regeneration of liver tissue in said subject.

2. The method of claim 1 wherein the 25HC3S is administered in an amount ranging from 0.1 mg/kg to 100 mg/kg, based on body mass of said subject.

3. The method of claim 1 wherein the 25HC3S is administered in an amount ranging from 1 mg/kg to 10 mg/kg, based on body mass of said subject.

4. The method of claim 1 wherein the administration comprises at least one of oral administration, enteric administration, sublingual administration, transdermal administration, intravenous administration, peritoneal administration, parenteral administration, administration by injection, subcutaneous injection, and intramuscular injection.

5. The method of claim 1 wherein said step of elevating is performed before, during or after liver surgery in said subject.

6. The method of claim 5 wherein the liver surgery comprises liver transplant surgery.

7. The method of claim 1 wherein said subject has at least one of liver injury, and hepatitis.

8. The method of claim 1, wherein said subject has viral hepatitis or autoimmune hepatitis.

9. The method of claim 1, wherein said subject has liver inflammation caused by a virus, a poison, a drug, or a hereditary condition.

10. The method of claim 1, wherein said subject has liver inflammation caused by a drug selected from the group consisting of amiodarone, an antiviral drug, aspirin, a corticosteroid, methotrexate, tamoxifen, and tetracycline.

11. The method of claim 4, wherein said administration comprises oral administration.

* * * * *